US012089901B2

(12) United States Patent
Moctezuma de la Barrera

(10) Patent No.: US 12,089,901 B2
(45) Date of Patent: *Sep. 17, 2024

(54) SURGICAL SYSTEMS AND METHODS FOR FACILITATING AD-HOC INTRAOPERATIVE PLANNING OF SURGICAL PROCEDURES

(71) Applicant: Stryker Corporation, Kalamazoo, MI (US)

(72) Inventor: José Luis Moctezuma de la Barrera, Freiburg (DE)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/218,159

(22) Filed: Jul. 5, 2023

(65) Prior Publication Data
US 2023/0355311 A1 Nov. 9, 2023

Related U.S. Application Data

(63) Continuation of application No. 17/328,512, filed on May 24, 2021, now Pat. No. 11,730,544, which is a
(Continued)

(51) Int. Cl.
*A61B 34/10* (2016.01)
*A61B 34/00* (2016.01)
(Continued)

(52) U.S. Cl.
CPC ............. *A61B 34/10* (2016.02); *A61B 34/20* (2016.02); *A61B 34/25* (2016.02); *A61B 34/30* (2016.02);
(Continued)

(58) Field of Classification Search
CPC ......... A61B 34/10; A61B 34/20; A61B 34/25; A61B 34/30; A61B 2034/101;
(Continued)

(56) References Cited

U.S. PATENT DOCUMENTS 7,206,627 B2 4/2007 Abovitz et al.
7,491,198 B2 2/2009 Kockro
(Continued)

OTHER PUBLICATIONS

International Search Report for Application No. PCT/IB2018/052596 dated Jul. 2, 2018, 4 pages.

*Primary Examiner* — Zhipeng Wang
(74) *Attorney, Agent, or Firm* — Howard & Howard Attorneys PLLC

(57) ABSTRACT

A surgical system, method and CAD program are provided. The surgical system includes a digitization device including a pointer tip to contact a target site and actuatable control input(s). A surgical tool can manipulate the target site. A navigation system tracks a state of the digitization device. Controller(s) receive the tracked state of the digitization device and display, within a virtual reference frame, a virtual representation of the pointer tip. In response to actuation of the control input(s), the controller(s) register virtual reference points within the virtual reference frame based on the pose of the virtual representation of the pointer tip and enable arrangement of one or more geometrical design objects within the virtual reference frame relative to the registered virtual reference points to generate a virtual boundary that defines a region of the target site to be avoided by the surgical tool.

20 Claims, 62 Drawing Sheets

Related U.S. Application Data continuation of application No. 15/952,810, filed on Apr. 13, 2018, now Pat. No. 11,071,590.

(60) Provisional application No. 62/502,414, filed on May 5, 2017, provisional application No. 62/485,779, filed on Apr. 14, 2017.

(51) Int. Cl.
| | |
|---|---|
| *A61B 34/20* | (2016.01) |
| *A61B 34/30* | (2016.01) |
| *G06F 3/0484* | (2022.01) |
| *G06T 19/00* | (2011.01) |
| *A61B 17/00* | (2006.01) |
| *A61B 90/00* | (2016.01) |
| *A61B 90/50* | (2016.01) |

(52) U.S. Cl.
CPC .......... *G06F 3/0484* (2013.01); *G06T 19/006* (2013.01); *A61B 2017/00216* (2013.01); *A61B 2034/101* (2016.02); *A61B 2034/102* (2016.02); *A61B 2034/105* (2016.02); *A61B 2034/107* (2016.02); *A61B 2034/108* (2016.02); *A61B 2034/2048* (2016.02); *A61B 2034/2051* (2016.02); *A61B 2034/2055* (2016.02); *A61B 2034/2063* (2016.02); *A61B 2034/2068* (2016.02); *A61B 2034/2074* (2016.02); *A61B 2034/252* (2016.02); *A61B 2090/365* (2016.02); *A61B 2090/372* (2016.02); *A61B 2090/3983* (2016.02); *A61B 2090/502* (2016.02); *A61M 2205/507* (2013.01); *G06T 2210/41* (2013.01)

(58) Field of Classification Search
CPC ........ A61B 2034/107; A61B 2034/108; A61B 2034/2051; G06F 3/0484
See application file for complete search history.

(56) References Cited

U.S. PATENT DOCUMENTS

| | | | |
|---|---|---|---|
| 7,643,862 | B2 | 1/2010 | Schoenefeld |
| 7,725,162 | B2 | 5/2010 | Malackowski et al. |
| 7,864,173 | B2 | 1/2011 | Handley et al. |
| 7,885,701 | B2 | 2/2011 | DiSilvestro et al. |
| 8,165,659 | B2 | 4/2012 | Sheffer et al. |
| 8,675,939 | B2 | 3/2014 | Moctezuma de la Barrera |
| 8,911,499 | B2 | 12/2014 | Quaid et al. |
| 9,008,757 | B2 | 4/2015 | Wu |
| 9,119,655 | B2 | 9/2015 | Bowling et al. |
| 9,226,796 | B2 | 1/2016 | Bowling et al. |
| 11,071,590 | B2 | 7/2021 | Moctezuma De la Barrera |
| 2004/0152970 | A1* | 8/2004 | Hunter .................. A61B 34/20 600/424 |
| 2008/0287803 | A1* | 11/2008 | Li .......................... A61B 5/064 382/128 |
| 2008/0306490 | A1* | 12/2008 | Lakin ..................... A61B 90/36 606/130 |
| 2008/0319491 | A1* | 12/2008 | Schoenefeld ...... A61B 17/1703 606/86 R |
| 2009/0089081 | A1* | 4/2009 | Haddad ................. G16H 20/40 705/2 |
| 2012/0030429 | A1 | 2/2012 | Synge |
| 2013/0060278 | A1 | 3/2013 | Bozung et al. |
| 2013/0211792 | A1* | 8/2013 | Kang ..................... A61B 34/30 703/1 |
| 2014/0276949 | A1 | 9/2014 | Staunton et al. |
| 2016/0128654 | A1* | 5/2016 | Wollowick ............ G16H 20/40 600/424 |
| 2016/0175054 | A1* | 6/2016 | Kang ..................... G09B 23/30 382/131 |
| 2016/0206376 | A1 | 7/2016 | Haider et al. |
| 2016/0225192 | A1* | 8/2016 | Jones ..................... G06F 3/011 |
| 2017/0112628 | A1* | 4/2017 | Dressler .................. A61F 2/34 |
| 2017/0360510 | A1* | 12/2017 | Bischoff ............... A61B 34/25 |
| 2018/0261009 | A1* | 9/2018 | Tepper .................. A61B 34/10 |
| 2018/0333207 | A1 | 11/2018 | Moctezuma De la Barrera |
| 2021/0275253 | A1 | 9/2021 | Moctezuma de la Barrera |

* cited by examiner

SURGICAL SYSTEMS AND METHODS FOR FACILITATING AD-HOC INTRAOPERATIVE PLANNING OF SURGICAL PROCEDURES

CROSS-REFERENCE TO RELATED APPLICATIONS

The subject application is a continuation of U.S. patent application Ser. No. 17/328,512, filed May 24, 2021, which is a continuation of U.S. patent application Ser. No. 15/952,810, filed Apr. 13, 2018, now U.S. Pat. No. 11,071,590, which claims priority to and all the benefits of U.S. Provisional Patent App. No. 62/485,779 filed on Apr. 14, 2017, and U.S. Provisional Patent App. No. 62/502,414 filed on May 5, 2017, the entire contents of each of the aforementioned applications being hereby incorporated by reference.

TECHNICAL FIELD

The present disclosure relates, generally, to surgical systems and, more specifically, to surgical systems and methods for facilitating ad-hoc intraoperative planning of surgical procedures.

BACKGROUND

The workflow associated with many conventional surgical procedures generally comprises three phases: diagnosis, planning, and execution. With the exception of time-sensitive emergency surgical interventions (e.g., treating traumatic injuries), the diagnosis and planning phases tend to be performed preoperatively and are followed by intraoperative execution. During the planning stage, a surgeon generally identifies or otherwise formulates discrete surgical steps to be performed during execution (often in a predetermined, ideal sequence). It will be appreciated that the planning phase can be highly subjective, and typically involves the surgeon taking a number of different factors into consideration, including without limitation: the type of surgical procedure to be executed; the types of tools, instrumentation, and prostheses which are available; the surgeon's preferences, training, and experience; the patient's condition, anatomy, and medical history; and the amount of time available before execution is to occur.

In many surgical procedures, the diagnosis and planning phases both frequently involve the use of preoperatively-acquired imaging (e.g., via X-ray, CT-scan, MRI, and the like). By way of illustrative example, a physician could diagnose a patient's condition (e.g., osteoarthritis) with an X-ray image acquired at a target site (e.g., the patient's hip joint), and an appropriate surgical procedure to be executed (e.g., total hip arthroplasty) could then be planned by a surgeon based on MRI scans of the patient's anatomy at the target site. Conventionally, the surgeon will formulate certain steps of the surgical plan based on measurements taken from one or more 2D images preoperatively-acquired at the target site.

By way of illustrative example, preoperative planning one or more types of orthopedic surgical interventions may involve surgical steps defined by the surgeon "tracing" or "marking up" an X-ray image of the patient's bone. Here, planning surgical steps may include drawing points at specific anatomical landmarks, drawing lines between or with respect to anatomical landmarks, taking measurements (e.g., distances and angles) between various lines and points that have been drawn, creating additional points and lines based on those measurements, and the like. Formulating these types of preoperative planning steps allows the surgeon to subsequently execute the surgical procedure in a patient-specific manner, whereby lines "traced" on the X-ray may represent or otherwise correspond to surgical steps to be made during execution (e.g., cutting bone in a way that corresponds to a line traced over the X-ray).

Advantageously, the surgical steps formulated with preoperative planning are executed as intended during the surgical procedure. However, it will be appreciated that postoperative results may not match a preoperative surgical plan for various reasons (e.g., human error during planning, unexpected complications during execution, variations in the patient's anatomy, and the like).

Execution of the surgical plan generally involves the surgeon utilizing one or more different types of surgical tools (e.g., saws, drills, milling devices, and the like) to facilitate approaching, manipulating, or otherwise effecting treatment of the target site. By way of illustration, surgical tools are commonly used in orthopedic surgical procedures which involve the correction, stabilization, resection, or replacement of one or more parts of the patient's anatomy, such as to help improve patient mobility, reduce pain, mitigate the risk of subsequent injury or damage, and the like.

In certain surgical procedures, a navigation system (or, "tracking system") may also be utilized during execution of the surgical plan in order to assist surgeons in, guiding, positioning, and/or moving surgical tools, instrumentation, prostheses, hardware, and the like relative to the target site with enhanced accuracy and precision. To this end, the navigation system generally tracks states of the surgical tool and also tracks states of one or more patient trackers attached to the patient's anatomy relative to the target site, both of which may move during the surgical procedure. Navigation systems are used in connection with both handheld surgical tools and surgical tools which are coupled to robotic manipulators. In some applications, the navigation system may also be configured to relate portions of the patient's anatomy to 3D renderings preoperatively-acquired at the target site in order to define virtual boundaries used to constrain the surgical tool to desired areas.

While the use of navigation systems, navigated surgical tools, and/or computer-aided preoperative planning affords opportunities for executing surgical procedures with enhanced accuracy and precision, it will be appreciated that the success of a surgical procedure depends on both precise preoperative planning and accurate reproduction of the plan during execution. In order for navigation systems and/or navigated surgical tools to work as intended, significant reliance is generally placed on preoperative planning and/or predefined workflows for executing certain types of surgical procedures, which may make it difficult for the surgeon to deviate from the preoperative plan during execution. Furthermore, it will be appreciated that certain surgical procedures are less suitable for the use of computer-aided preoperative planning, navigation systems, and/or navigated surgical tools, such as where the target site is difficult to approach, involves complex tissue geometry, involves a revision of a previous procedure, or involves an emergency surgical intervention. As such, many types of surgical procedures are routinely carried "manually" without the benefits afforded by computer-aided planning, navigation systems, and/or navigated surgical tools.

Additionally, conventional techniques do not afford the surgeon the ability to intraoperatively plan surgical steps "on the fly" using computer-aided technology. The resources (e.g., software) used for preoperative planning are no longer available, cannot be practically incorporated, or otherwise are incapable of providing any meaningful output during surgery. This limits the surgeon's ability to make ad-hoc adjustments or customized plans in the operating room.

Computer-aided preoperative planning also restricts the workflow by which the surgeon is able to plan a surgical step. For example, planning programs may limit how an implant is shaped, how/where the implant can be defined relative to the anatomical model, and so on. Thus, conventional planning approaches fail to provide the untethered creative freedom to enable surgeons to plan the surgery as they see fit.

Moreover, computer-aided preoperative planning requires a significant amount of resources and time from the surgeon, and others. For these reasons, many surgeons maintain a manual approach to surgery that does not involve the complexity of computer-aided preoperative planning. The state of the art provides no "middle ground" alternative for such surgeons.

Accordingly, there remains a need in the art to address at least the aforementioned issues.

SUMMARY

According to a first aspect, a surgical system is provided, comprising: a digitization device comprising a pointer tip configured to contact a target site and one or more control inputs that are configured to be actuated; a surgical tool configured to manipulate the target site; a navigation system configured to track a state of the digitization device; and one or more controllers configured to: receive the tracked state of the digitization device from the navigation system; display, within a virtual reference frame, a virtual representation of the pointer tip having a pose of the pointer tip derived from the tracked state of the digitization device; in response to actuation of the one or more control inputs of the digitization device, register virtual reference points within the virtual reference frame at locations based on the pose of the virtual representation of the pointer tip; and in response to actuation of the one or more control inputs of the digitization device, enable arrangement of one or more geometrical design objects within the virtual reference frame relative to the registered virtual reference points to generate a virtual boundary that defines a region of the target site to be avoided by the surgical tool.

According to a second aspect, a method is provided of operating a surgical system, the surgical system including a digitization device comprising a pointer tip configured to contact a target site and one or more control inputs, a surgical tool configured to manipulate the target site; a navigation system configured to track a state of the digitization device, and a one or more controllers, the method comprising the one or more controllers performing the following: receiving the tracked state of the digitization device from the navigation system; displaying, within a virtual reference frame, a virtual representation of the pointer tip having a pose of the pointer tip derived from the tracked state of the digitization device; in response to actuation of the one or more control inputs of the digitization device, registering virtual reference points within the virtual reference frame at locations based on the pose of the virtual representation of the pointer tip; and in response to actuation of the one or more control inputs of the digitization device, enabling arrangement of one or more geometrical design objects within the virtual reference frame relative to the registered virtual reference points for generating a virtual boundary that defines a region of the target site to be avoided by the surgical tool.

According to a third aspect, a non-transitory computer-readable medium is provided having stored thereon instructions, which when executed by one or more processors, are configured to execute a computer-aided design (CAD) program configured to be utilized with a surgical system, the surgical system including a digitization device comprising a pointer tip configured to contact a target site and one or more control inputs that are configured to be actuated, and a navigation system configured to track a state of the digitization device, the CAD program, when executed, is configured to: receive the tracked state of the digitization device from the navigation system; display, within a virtual reference frame, a virtual representation of the pointer tip having a pose of the pointer tip derived from the tracked state of the digitization device; in response to actuation of the one or more control inputs of the digitization device, register virtual reference points within the virtual reference frame at locations based on the pose of the virtual representation of the pointer tip; and in response to actuation of the one or more control inputs of the digitization device, enable arrangement of one or more geometrical design objects within the virtual reference frame relative to the registered virtual reference points to generate a virtual boundary that defines a region of the target site to be avoided by a surgical tool.

Other features and advantages of the present disclosure will be readily appreciated, as the same becomes better understood, after reading the subsequent description taken in conjunction with the accompanying drawings.

DETAILED DESCRIPTION

Figure 1:
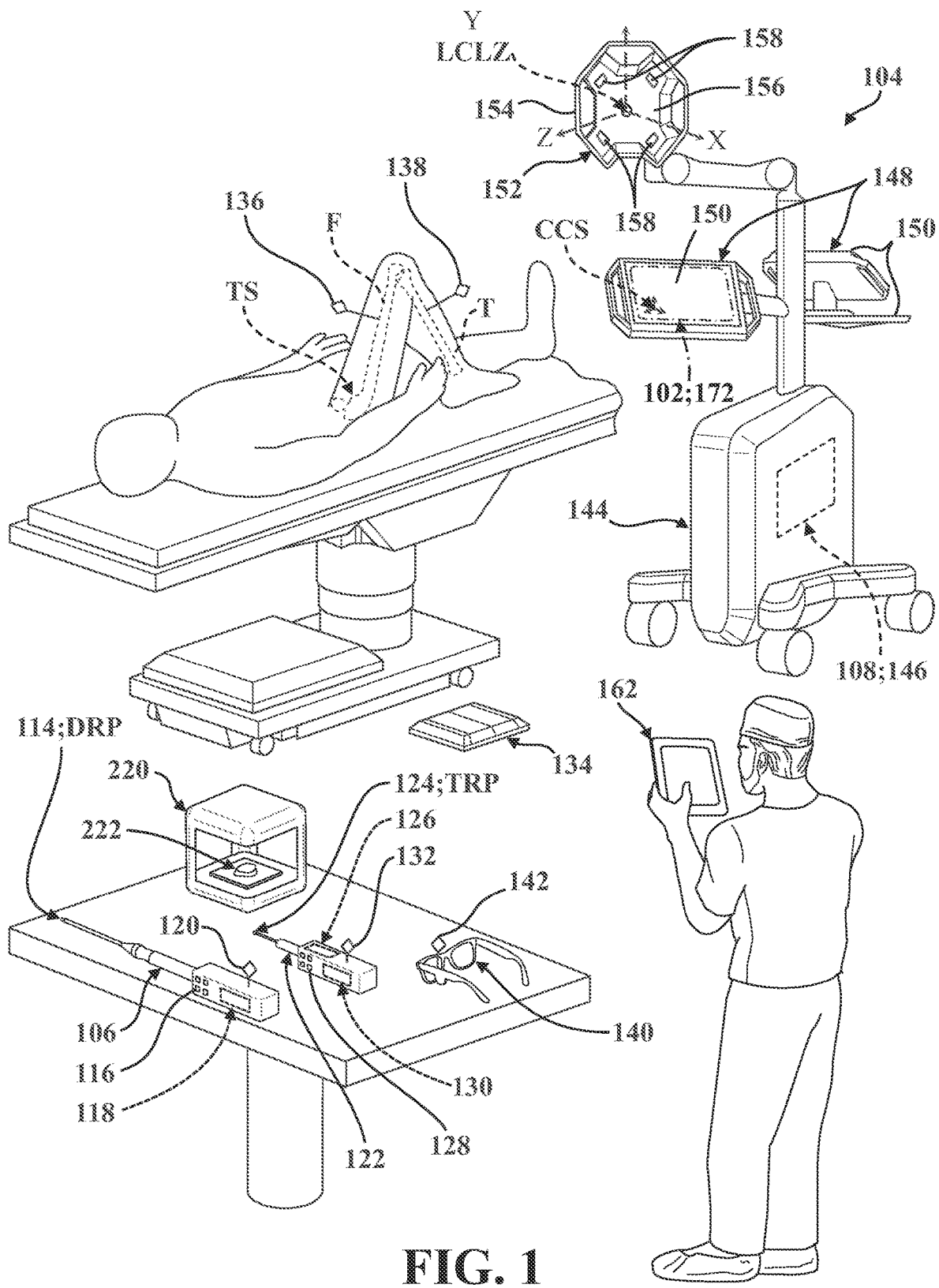
FIG. 1 is a perspective view of a surgical system for facilitating ad-hoc intraoperative planning of a surgical step to be performed at a target site, the surgical system shown comprising a navigation system, a digitization device, a surgical tool, a head-mountable display (HMD) unit, a patient tracker attached to a patient's anatomy, a control input, and a computing device according to one embodiment of the present disclosure.

With reference now to the drawings, wherein like numerals indicate like parts throughout the several views, embodiments of a surgical system 100 and computer-implemented techniques and methods associated with the surgical system 100, including a computer-aided design (CAD) program 102, are shown throughout (see FIG. 1). As is described in greater detail below, the various embodiments of the present disclosure enable a user (e.g., a surgeon) to facilitate ad-hoc intraoperative planning of a surgical step to be performed at a target site TS of a patient's anatomy that is the subject of a surgical procedure.

In FIG. 1, an operating room is shown with a patient undergoing an example surgical procedure performed using one embodiment of the surgical system 100 and the CAD program 102 of the present disclosure. In this illustrative example, the target site TS includes portions of the patient's femur (F) and tibia (T). However, it will be appreciated that the target site TS could comprise any suitable portion of the patient's anatomy for a given surgical procedure, including other bones and various other types of tissue. Moreover, it will be appreciated that the surgical system 100 and the CAD program 102 described herein may be used in connection with facilitating ad-hoc intraoperative planning of surgical steps for a variety of different types of surgical procedures.

As used herein, the term "intraoperative" means occurring, being carried out, or existing during the execution of a surgical procedure (e.g., inside an operating room) and, in contrast, the term "preoperative" means occurring, being carried out, or existing before execution of the surgical procedure (e.g., outside of the operating room). Furthermore, as used herein, the term "ad-hoc" means that one or more steps of the surgical procedure are planned intraoperatively or "on-the-fly" during execution of the surgical procedure (e.g., inside the operating room).

In some embodiments, ad-hoc intraoperative planning may involve formulating improvised surgical steps which deviate from a preoperatively-formulated surgical plan, or may involve formulating improvised surgical steps without reliance on a preoperatively-formulated surgical plan. Thus, as is described in greater detail below, the surgeon can plan one or more surgical steps intraoperatively using the surgical system 100 and CAD program 102 of the present disclosure without necessarily relying on preoperatively-acquired patient-specific imaging of the target site TS (e.g., a 2D image acquired via X-ray imaging, or a 3D rendering/model generated via MRI imaging segmentation). However, certain aspects and embodiments of the present disclosure could also be used to intraoperatively validate, verify, confirm, or otherwise compliment (or accommodate deviating from) a preoperatively-formulated surgical plan which may or may not rely on patient-specific preoperatively-acquired imaging of the target site TS.

Figure 2:
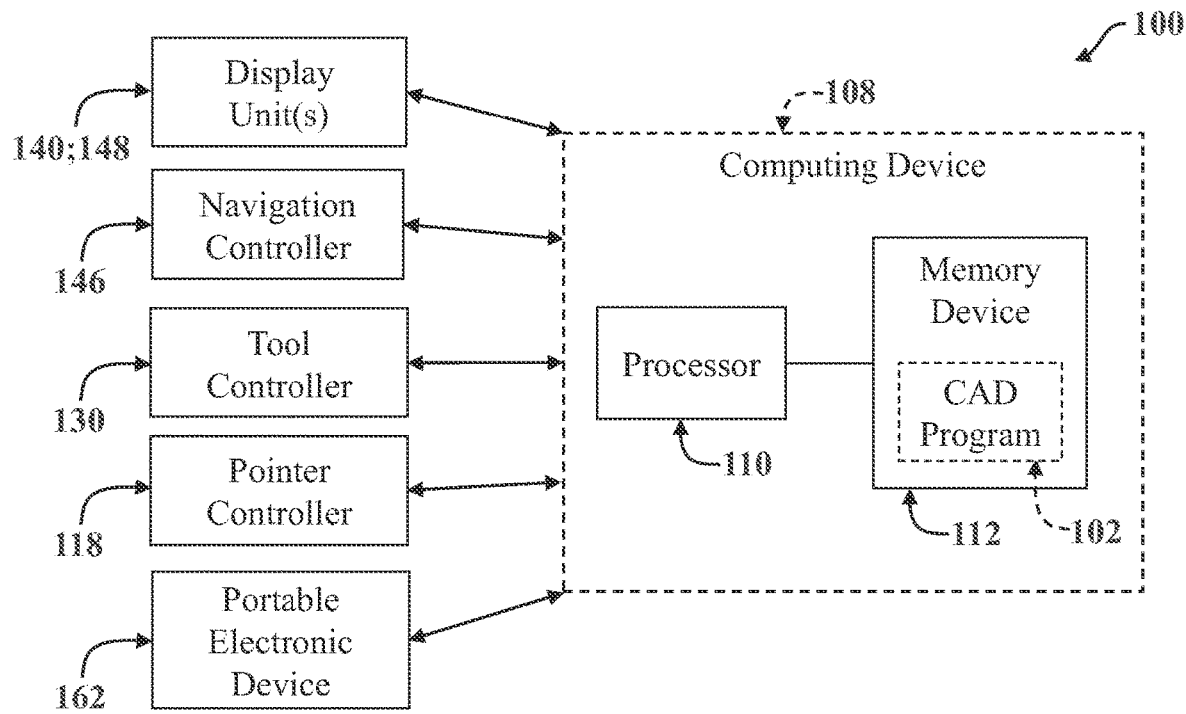
FIG. 2 is a block diagram illustrating general communication between the computing device and other components of the surgical system of FIG. 1, the computing device shown having a memory device with a computer-aided design (CAD) program stored thereon according to one embodiment of the present disclosure.
Figure 3:
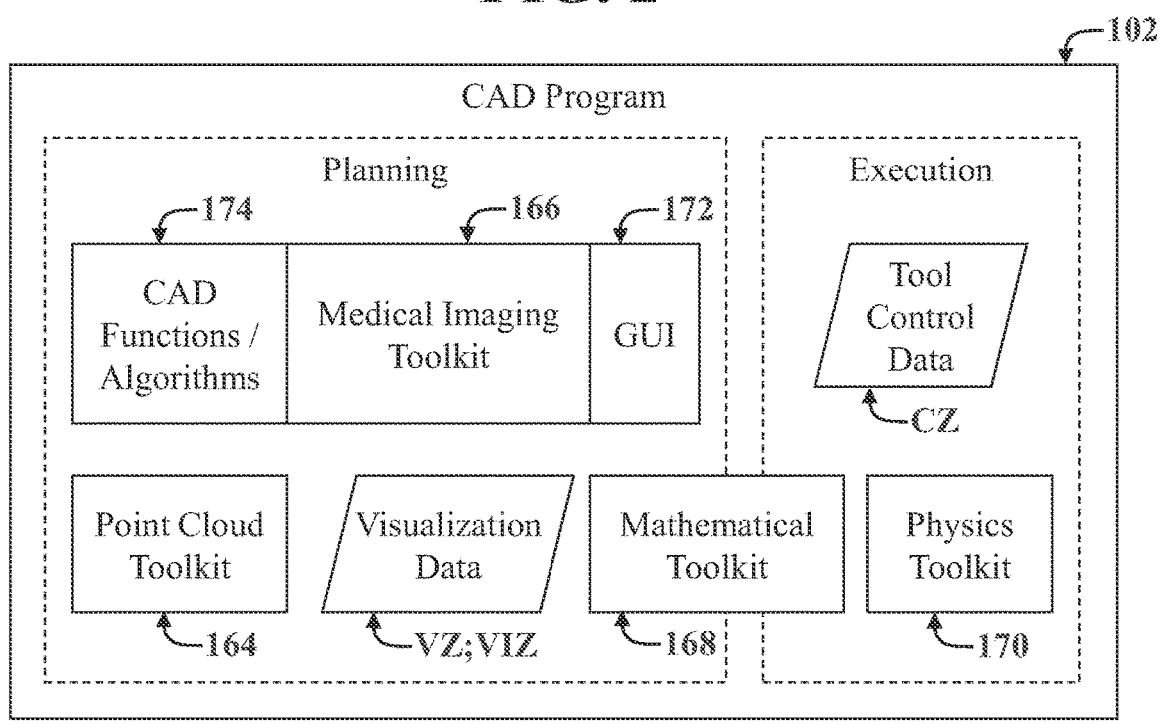
FIG. 3 is a block diagram illustrating an example software architecture of the CAD program of FIG. 2 according to one embodiment of the present disclosure.
Figure 4:
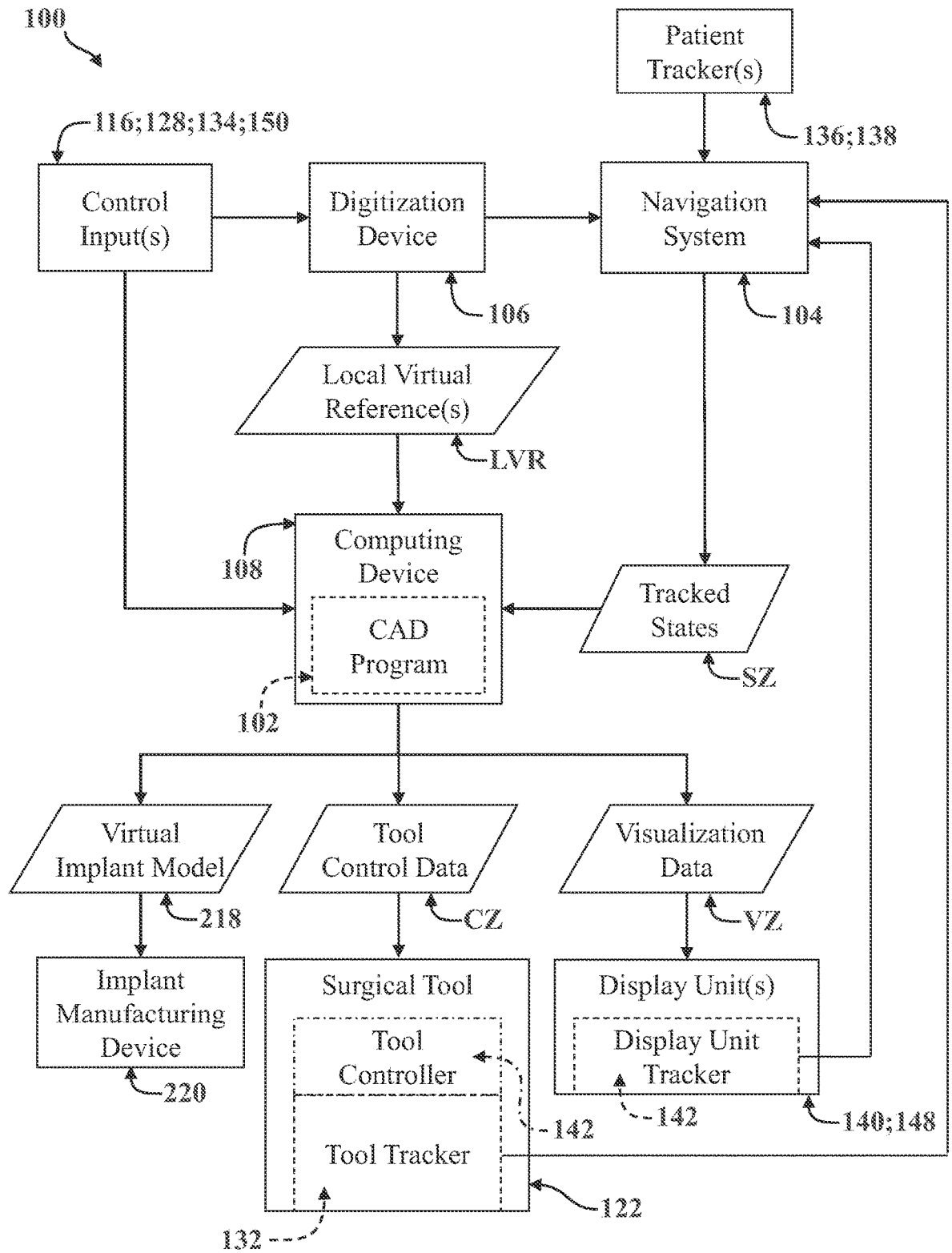
FIG. 4 is a schematic diagram illustrating example interactions between the navigation system, the digitization device, the surgical tool, the HMD unit, the patient tracker, the control input, and the CAD program of the computing device of FIG. 1.

Referring now to FIGS. 1-19F, in order to facilitate ad-hoc intraoperative planning of the surgical step, the surgical system 100 generally comprises a navigation system 104 (see FIGS. 1-2, 4, and 18-19D), a digitization device 106 (see FIGS. 1 and 19A-19D), and a computing device 108 (see FIGS. 2 and 4). The navigation system 104 is configured to, among other things, track states of the digitization device 106 which, in turn, is configured to facilitate intraoperatively establishing one or more local virtual references LVR relative to the target site TS (see FIGS. 19A-19F). The computing device 108 is coupled to or is otherwise disposed in communication with the navigation system 104, and comprises one or more processors 110 and a non-transitory storage medium, such as a memory device 112, which the CAD program 102 is stored on (see FIG. 2).

When executed by the one or more processors 110 of the computing device 108, the CAD program 102 is configured to generate a virtual reference frame VRF (see FIGS. 9A-17 and 19A-19F), to register local virtual references LVR within the virtual reference frame VRF, and to enable arrangement of different geometrical design objects GDO (see FIG. 6; see also FIGS. 5, 7-17, and 19A-19F) within the virtual reference frame VRF relative to one or more registered local virtual references LVR to intraoperatively plan the surgical step. The configuration of and interaction between the CAD program 102 and the components of the surgical system 100 introduced above will be described in greater detail below.

Referring now to FIG. 1, the digitization device 106 of the surgical system 100 is movable relative to the target site TS and is configured for hand-held operation by the surgeon, or another user of the surgical system 100, to intraoperatively establish one or more local virtual references LVR relative to the target site TS which, noted above, can be registered by the CAD program 102 and used to facilitate planning the surgical step, as described in greater detail below.

The digitization device 106 illustrated throughout the drawings is realized as a "straight pointer" and generally comprises a pointer tip 114, one or more pointer control inputs 116, a pointer controller 118, and a pointer tracker 120 (depicted schematically in FIG. 1). The pointer tip 114 is configured to engage against portions of the patient's anatomy at or about the target site TS (e.g., by touching against bone). The pointer control input 116 is arranged for actuation by the surgeon to, among other things, facilitate establishing the local virtual references LVR and, in some embodiments, facilitate operating the CAD program 102. It will be appreciated that the pointer control input 116 of the digitization device 106 could be configured in a number of different ways sufficient to be actuated by the surgeon (e.g., with buttons, triggers, switches, knobs, levers, touchscreens, and the like).

In the illustrated embodiment, the pointer control input 116 communicates with the pointer controller 118 which, in turn, communicates with the computing device 108, the navigation system 104, and/or other components of the surgical system 100, such as via physical electrical connections (e.g., a tethered wire harness) and/or via one or more types of wireless communication (e.g., with a WiFi™ network, Bluetooth®, a radio network, and the like). It will be appreciated that the pointer controller 118 may be configured in a number of different ways and could comprise and/or support various types of electrical components (e.g., sensors, processors, integrated circuits, transceivers, and the like) in some embodiments. In the representative embodiment illustrated herein, the pointer tracker 120 is firmly affixed to the digitization device 106 and enables the navigation system 104 to track states of the digitization device 106, as noted above and as is described in greater detail below. In some embodiments, the digitization device 106 may define a predetermined digitizer reference point DRP which represents a relative position of the pointer tip 114 within a digitizer coordinate system DCS defined by the position and orientation of the pointer tracker 120 relative to the pointer tip 114 (see FIG. 18). Thus, the term "pointer tip 114" and the term "digitizer reference point DRP" may be used interchangeably herein.

In some embodiments, the digitization device 106 could be configured similar to as is shown in U.S. Pat. No. 7,725,162, entitled, "Surgery System," the disclosure of which is hereby incorporated by reference. However, it will be appreciated that the digitization device 106 could be configured in other ways in some embodiments. Moreover, and as will be appreciated from the subsequent description below, the surgical system 100 could comprise additional and/or differently-configured digitization devices 106 in some embodiments, such as to facilitate establishing local virtual references LVR at the target site TS in other ways (e.g., a hand-held ultrasonic scanner which may not directly contact portions of the target site TS). Other configurations are contemplated.

Those having ordinary skill in the art will appreciate that many conventional surgical procedures involve removing or otherwise treating tissue of the patient's anatomy (e.g., resecting, cutting, milling, coagulating, lesioning, and the like). In some surgical procedures, portions of the patient's anatomy are removed and replaced by one or more prosthetic implants (e.g., hip and knee joint implants). Various prosthetic implants are shown in U.S. Patent Application Publication No. 2012/0030429, entitled, "Prosthetic Implant and Method of Implantation," the disclosure of which is hereby incorporated by reference.

In order to facilitate removing or otherwise treating tissue of the patient's anatomy, the surgical system 100 may comprises one or more types of surgical tools 122 in some embodiments. The surgical tool 122 can be used manually by the surgeon during execution of the surgical procedure, or, in some embodiments, the surgical system 100 may allow the surgeon to navigate the surgical tool 122 with respect to geometrical design objects GDO arranged within the virtual reference frame VRF and/or control the surgical tool 122 to facilitate guided execution of one or more intraoperatively-planned surgical steps, as is described in greater detail below.

With continued reference to FIG. 1, the surgical tool 122 is movable relative to the target site TS and is configured to engage, remove, cut, manipulate, or otherwise effect treatment of tissue during the execution of the surgical procedure. To this end, the illustrated embodiment of the surgical tool 122 depicted throughout the drawings is realized as a hand-held rotary instrument comprising an energy applicator 124, an actuator 126, one or more tool control inputs 128, a tool controller 130, a tool tracker 132 (depicted schematically in FIG. 1). The energy applicator 124 is configured to engage tissue at the target site TS during execution of the surgical procedure, and may be of a number of different types, styles, and/or configurations (e.g., a drill bit, a saw blade, a bur, a vibrating tip, and the like). The actuator 126 is coupled to and drives the energy applicator 124 (e.g., by generating rotational torque), and may likewise be of different types, styles, and/or configurations (e.g., an electric motor, an ultrasonic transducer, and the like). The tool control input 128 is arranged for actuation by the surgeon to facilitate driving the energy applicator 124. It will be appreciated that the tool control input 128 could be configured in a number of different ways sufficient to be actuated by the surgeon (e.g., with buttons, triggers, switches, knobs, levers, touchscreens, and the like).

In the illustrated embodiment, the tool control input 128 communicates with the tool controller 130 which, in turn, communicates with the computing device 108, the navigation system 104, and/or other components of the surgical system 100, such as via physical electrical connections (e.g., a tethered wire harness) and/or via one or more types of wireless communication (e.g., with a WiFi™ network, Bluetooth®, a radio network, and the like). It will be appreciated that the tool controller 130 may be configured in a number of different ways and could comprise and/or support various types of electrical components (e.g., sensors, processors, integrated circuits, transceivers, and the like) in some embodiments. Examples of the utilization of tool controllers 130 of this type for execution of surgical procedures can be found in U.S. Pat. No. 9,226,796, entitled "Method for Detecting a Disturbance as an Energy Applicator of a Surgical Instrument Traverses a Cutting Path," the disclosure of which is hereby incorporated by reference.

In the representative embodiment illustrated herein, the tool tracker 132 is firmly affixed to the surgical tool 122 and enables the navigation system 104 to track states of the surgical tool 122, as described in greater detail below. In some embodiments, the surgical tool 122 may define a predetermined tool reference point TRP which represents a relative position of the energy applicator 124 within a tool coordinate system TCS defined by the position and orientation of the tool tracker 132 relative to energy applicator 124 (see FIG. 18).

In addition to driving the actuator 126 based on communication with the tool control input 128 (e.g., such as in response to signals generated by the tool control input 128), the tool controller 130 may also drive the actuator 126 based on communication with other control inputs associated with the surgical system 100, such as a foot pedal control input 134 (see FIG. 1). Furthermore, in some embodiments, and as is described in greater detail below, the tool controller 130 may also drive the actuator 126 based on communication with other components of the surgical system 100 (e.g., the navigation system 104) in order to facilitate operating the actuator 126 in different ways based on the relative position and/or orientation of the surgical tool 122 relative to the target site TS (e.g., to facilitate guided execution of one or more intraoperatively-planned surgical steps).

As noted above, the surgical tool 122 could be of a number of different types and/or configurations to engage tissue at the target site TS during execution of the surgical procedure. In some embodiments, the surgical tool 122 could be configured similar to as is shown in U.S. Patent Application Publication No. 2013/0060278, entitled, "Surgical Instrument Including Housing, a Cutting Accessory that Extends from the Housing and Actuators that Establish the Position of the Cutting Accessory Relative to the Housing", the disclosure of which is hereby incorporated by reference.

While the surgical tool 122 illustrated herein is configured for un-tethered, hand-held operation by the surgeon, as noted above, the surgical tool 122 could also be realized with an end effector attached to a manipulator of a surgical robot configured to move the energy applicator 124 relative to the target site TS by articulating the manipulator (not shown). One example arrangement of a surgical tool 122 realized with a surgical robot end effector manipulator is described in U.S. Pat. No. 9,119,655, entitled, "Surgical Manipulator Capable of Controlling a Surgical Instrument in Multiple Modes," the disclosure of which is hereby incorporated by reference. Another example arrangement of a surgical tool 122 realized with a surgical robot end effector manipulator is described in U.S. Patent Application Publication No. 2014/0276949, filed on Mar. 15, 2014, entitled, "End Effector of a Surgical Robotic Manipulator," the disclosure of which is hereby incorporated by reference.

Referring now to FIGS. 1 and 18-19A, as noted above, the surgical system 100 employs the navigation system 104 (sometimes referred to as a "tracking system") to, among other things, track states of the digitization device 106 and the surgical tool 122. More specifically, the navigation system 104 is configured to track states of the pointer tracker 120 and the tool tracker 132. Furthermore, in some embodiments, the navigation system 104 is also configured to track states of a first patient tracker 136, and/or a second patient tracker 138, respectively attached to different portions of the patient's anatomy relative to the target site TS. In the embodiment depicted in FIG. 1, the first patient tracker 136 is firmly affixed to the femur F of the patient's anatomy, and the second patient tracker 138 is firmly affixed to the tibia T of the patient's anatomy. In some embodiments, the first patient tracker 136 (and/or the second patient tracker 138) may define a patient coordinate system PCS (see FIG. 18).

In some embodiments, the surgical system 100 may also comprise a head-mountable display (HMD) unit 140. As is described in greater detail below, the HMD unit 140 is configured to render a visualization of certain aspects the CAD program 102 such that the visualization is visible to the surgeon overlaid onto the target site TS with augmented reality and/or mixed reality (see FIGS. 19F, 40B, and 46B). Here too, the navigation system 104 is configured to track states of the HMD unit 140. To this end, the HMD unit 140 comprises a display tracker 142 which is firmly affixed to the HMD unit 140. In some embodiments, the display tracker 142 may define a display coordinate system HCS (see FIG. 18).

As is depicted in FIG. 1, the illustrated navigation system 104 includes a cart assembly 144 that houses a navigation controller 146 which is disposed in communication with one or more display units 148, one or more control inputs 150, and a localizer 152, each of which are described in greater detail below. One example of the type of navigation system 104 described herein is shown in U.S. Pat. No. 9,008,757, filed on Sep. 24, 2013, entitled, "Navigation System Including Optical and Non-Optical Sensors," hereby incorporated by reference.

The navigation controller 146 may be of a number of different styles, types, or configurations, and may also be disposed in communication with other components of the surgical system 100, such as the digitization device 106 (e.g., the pointer control input 116 and/or the pointer controller 118), the surgical tool 122 (e.g., the tool control input 128 and/or the tool controller 130), the foot pedal control input 134, the computing device 108, and the and the like. In some embodiments, the navigation controller 146 may comprise the computing device 108. Here too, communication between the navigation controller 146 and the various other components of the surgical system 100 described herein may occur in a number of different ways, including by various types of wired and/or wireless communication.

The display units 148 of the navigation system 104 may be configured to display a navigation interface in operative communication with the navigation controller 146 (navigation interface not shown) to the surgeon or another user. It will be appreciated that the one or more display units 148 could be configured in a number of different ways without departing from the scope of the present disclosure.

In some embodiments, one or more of the display units 148 are configured to display aspects of the CAD program 102 to the surgeon. For example, in some embodiments, the CAD program 102 is configured to render a visualization VIZ of the virtual reference frame VRF which may be displayed by one or more of the display units 148 of the navigation system 104 (sec FIGS. 9A-17, 19A-40A, 41-46A, and 47-49), and/or by the HMD unit 140 in some embodiments (see FIGS. 19F, 40B, and 46B).

Furthermore, and as is described in greater detail below, the CAD program 102 may be further configured to render, within the visualization VIZ of the virtual reference frame VRF: a virtual representation of the digitization device 106 (hereinafter, "virtual digitization device 106V") having a position and/or orientation derived from the tracked states SZ of the digitization device 106 (see FIGS. 19A-19D, 20A-40A, and 41-45); a virtual representation of the surgical tool 122 (hereinafter, "virtual surgical tool 122V") having a position and/or orientation derived from the tracked states SZ of the surgical tool 122 (see FIGS. 46A and 47-49); a virtual representation of the first patient tracker 136 (hereinafter, "virtual first patient tracker 136V") having a position and/or orientation derived from the tracked states SZ of the first patient tracker 136 (see FIGS. 19A-40A, 41-46A, and 47-49); and/or a virtual representation of the second patient tracker 138 (hereinafter, "virtual second patient tracker 138V") having a position and/or orientation derived from the tracked states SZ of the second patient tracker 138 (see FIGS. 20A-26B).

Furthermore, in some embodiments, the CAD program 102 may be configured to render, within the visualization VIZ of the virtual reference frame VRF: a virtual representation of the digitizer coordinate system DCS (hereinafter, "virtual digitizer coordinate system DCSV") associated with the virtual digitization device 106V; a virtual representation of the patient coordinate system PCS (hereinafter, "virtual patient coordinate system PCSV") associated with the virtual first patient tracker 136V; and/or a virtual representation of the tool coordinate system TCS (hereinafter, "virtual tool coordinate system TCSV") associated with the virtual first patient tracker 136V (virtual tool coordinate system TCSV not shown).

Further still, in some embodiments, the CAD program may be configured to render, within the visualization VIZ of the virtual reference frame VRF: a virtual representation of the digitizer reference point DRP (hereinafter, "virtual digitizer reference point DRPV") having a position known relative to the virtual digitizer coordinate system DCSV within the virtual reference frame VRF; and/or a virtual representation of the tool reference point TRP (hereinafter, "virtual tool reference point TRPV") having a position known relative to the virtual tool coordinate system TCSV within the virtual reference frame VRF.

The control inputs 150 of the navigation system 104 are generally configured to facilitate operating the navigation interface (not shown) of the navigation system 104 and, in some embodiments, are also configured to facilitate operating the CAD program 102. To this end, the control inputs 150 depicted in FIG. 1 comprise interactive touchscreens coupled to the display units 148. However, the control inputs 150 may include any one or more of a keyboard, a mouse, a microphone (e.g., for voice-activation), a gesture-based control device, and the like. In embodiments where the digitization device 106 is configured to facilitate operating the CAD program 102, it may also serve as one of the control inputs 150 of the navigation system 104. For example, the digitization device 106 may be serve as a control input 150 based on tracked states SZ of the digitization device 106, based on actuation of the pointer control input 116, and/or based on signals generated by the pointer controller 118 (e.g., from sensors of various types, including inertial sensors, accelerometers, gyroscopes, and the like). Other configurations are contemplated.

Referring again to FIGS. 1 and 18-19A, as noted above, the navigation system 104 is configured to track states of the pointer tracker 120, the tool tracker 132, the first patient tracker 136, the second patient tracker 138, the display unit tracker 142, and/or other trackers utilized during the surgical procedure. More specifically, the localizer 152 is configured to sense, track, or otherwise monitor the position and/or orientation (the "pose") of the respective trackers at respective coordinates within a localizer coordinate system LCLZ based, for example, on the relative pose of the digitizer coordinate system DCS, the tool coordinate system TCS, the patient coordinate system PCS, and/or the display coordinate system HCS within the localizer coordinate system LCLZ (see FIG. 18).

The localizer 152 monitors the trackers 120, 132, 136, 138, 142 to determine a state of each of the trackers 120, 132, 136, 138, 142 which corresponds to the state of the object respectively attached thereto. The navigation controller 146 gathers data about the tracked states SZ of each tracker 120, 132, 136, 138, 142 monitored by the localizer 152 within the localizer coordinate system LCLZ. The navigation controller 146 communicates the tracked states SZ of one or more of the trackers 120, 132, 136, 138, 142 to the computing device 108 implementing the CAD program 102 (shown in FIG. 2), which can be used to facilitate ad-hoc intraoperative planning of surgical steps as noted above and as is described in greater detail below.

As used herein, the term "tracked state SZ" includes, but is not limited to, data which represents or defines the position and/or orientation of a tracked object, and/or equivalents or derivatives of the position and/or orientation. For example, a tracked state SZ may be a pose of the tracked object, and may include linear data, angular velocity data, and the like. Other configurations are contemplated.

In the illustrated embodiment, the localizer 152 is an optical localizer and includes a camera unit 154. The camera unit 154 has an outer casing 156 that houses one or more optical sensors 158. Here, the optical sensors 158 are configured to sense movement of the various trackers 120, 132, 136, 138, 142. To this end, any one or more of the trackers 120, 132, 136, 138, 142 may include active markers 160 (see FIG. 18). The active markers 160 may include light emitting diodes (LEDs). Alternatively, the trackers 120, 132, 136, 138, 142 may have passive markers, such as reflectors which reflect light emitted from the camera unit 154 or another predetermined light source. Other suitable markers not specifically described herein may be utilized.

Although one embodiment of the navigation system 104 illustrated throughout the drawings, the navigation system 104 may have any other suitable configuration for tracking the HMD unit 140, the surgical tool 122, the digitization device 106, and/or trackers attached to portions of the patient's anatomy at the target site TS. In some embodiments, the navigation system 104 and/or the localizer 152 are ultrasound-based. For example, the navigation system 104 may comprise an ultrasound imaging device coupled to the navigation controller 146 and configured to facilitate acquiring ultrasound images (e.g., of the HMD unit 140, the surgical tool 122, the digitization device 106, the trackers attached at the target site TS, and the like) such that tracked states SZ are communicated to (or interpreted by) the navigation controller 146 based on the ultrasound images. The ultrasound images may be 2D, 3D, or a combination thereof. The navigation controller 146 may process ultrasound images in near real-time to determine the tracked states SZ. The ultrasound imaging device may have any suitable configuration and may be different than the camera unit 154 as shown in FIG. 1.

In some embodiments, the navigation system 104 and/or the localizer 152 are radio frequency (RF) based. For example, the navigation system 104 may comprise an RF transceiver coupled to the navigation controller 146. The HMD unit 140, the surgical tool 122, the digitization device 106, and the trackers attached to portions of the patient's anatomy at the target site TS may comprise RF emitters or transponders attached thereto. The RF emitters or transponders may be passive, or may be actively energized. The RF transceiver transmits an RF tracking signal, and the RF emitters respond with RF signals such that tracked states SZ are communicated to (or interpreted by) the navigation controller 146. The RF signals may be of any suitable frequency. The RF transceiver may be positioned at any suitable location to track the objects using RF signals effectively. Furthermore, it will be appreciated that embodiments of RF-based navigation systems may have structural configurations that are different than the navigation system 104 illustrated throughout the drawings.

In some embodiments, the navigation system 104 and/or localizer 152 are electromagnetically (EM) based. For example, the navigation system 104 may comprise an EM transceiver coupled to the navigation controller 146. The HMD unit 140, the surgical tool 122, the digitization device 106, and the trackers attached to portions of the patient's anatomy at the target site TS may comprise EM components attached thereto (e.g., various types of magnetic trackers, electromagnetic trackers, inductive trackers, and the like) which may be passive, or may be actively energized. The EM transceiver generates an EM field, and the EM components respond with EM signals such that tracked states SZ are communicated to (or interpreted by) the navigation controller 146. The navigation controller 146 may analyze the received EM signals to associate relative states thereto. Here too, it will be appreciated that embodiments of EM-based navigation systems may have structural configurations that are different than the navigation system 104 illustrated throughout the drawings.

Those having ordinary skill in the art will appreciate that the navigation system 104 and/or localizer 152 may have any other suitable components or structure not specifically recited herein. Furthermore, any of the techniques, methods, and/or components described above with respect to the camera-based navigation system 104 shown throughout the drawings may be implemented or provided for any of the other embodiments of the navigation system 104 described herein. For example, the navigation system 104 may utilize solely inertial tracking or any combination of tracking techniques.

Figure 18:
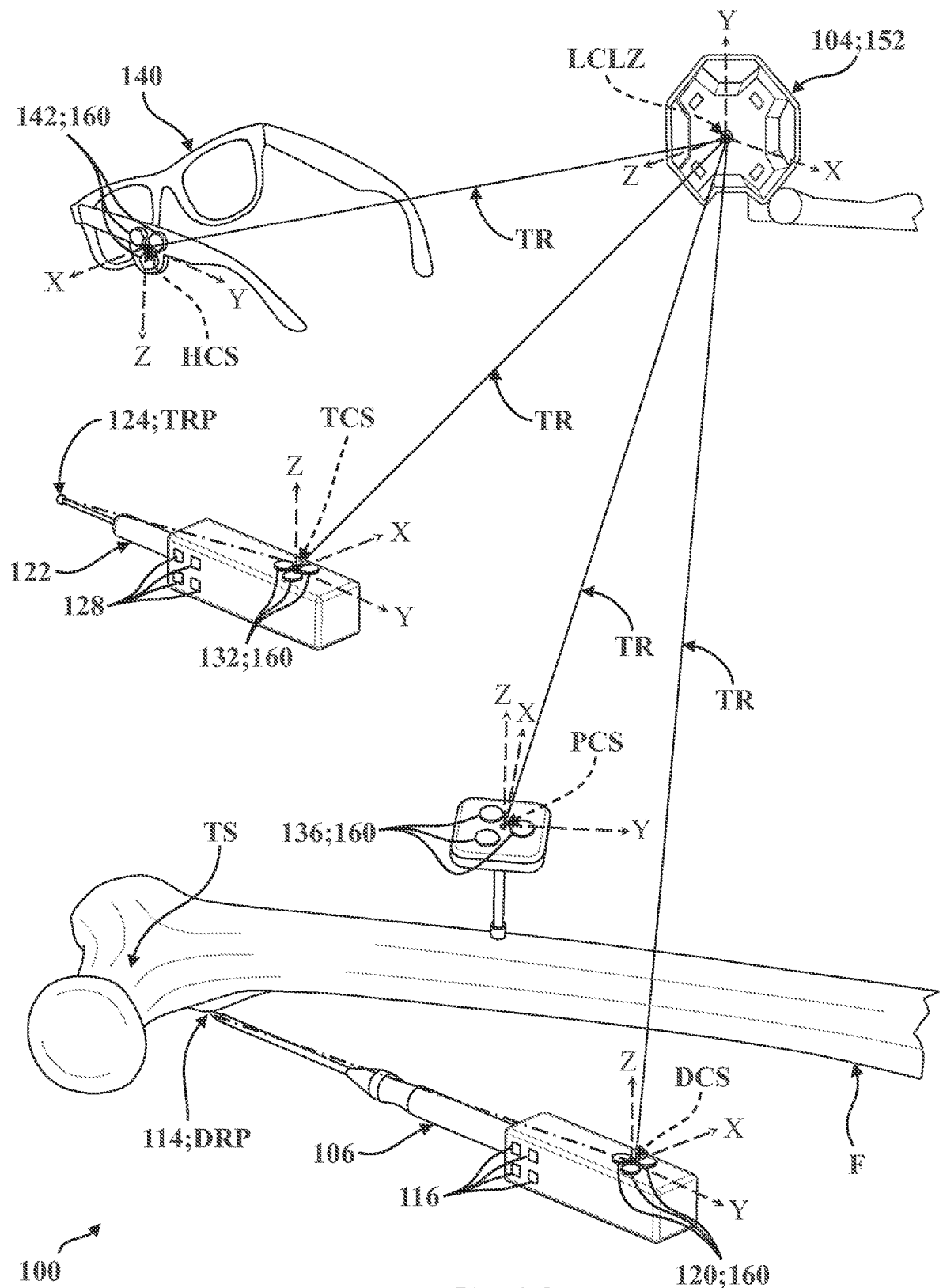
FIG. 18 is an enlarged partial perspective view of components of the surgical system of FIG. 1, illustrating transforms between a localizer of the navigation system and trackers of the digitization device, the surgical tool, the HMD unit, and the patient tracker shown attached to the patient's femur.

Referring now to FIG. 18, as noted above, the localizer 152 of the navigation system 104 is able to track states of each of the trackers 120, 132, 136, 138, 142 within the localizer coordinate system LCLZ. Thus, the navigation controller 146 is able to simultaneously monitor, within the localizer coordinate system LCLZ, changes in the position and/or orientation of: the digitizer coordinate system DCS (or the position of the digitizer reference point DRP relative thereto); the tool coordinate system TCS (or the position of the tool reference point TRP relative thereto); the patient coordinate system PCS; and/or the display coordinate system HCS. Here, data associated with the pose of one or more of the trackers 120, 132, 136, 138, 142 within the localizer coordinate system LCLZ may be translated (e.g., with the navigation controller 146, with the computing device 108, and the like) into an arbitrary CAD coordinate system CCS within the virtual reference frame VRF of the CAD program 102, and/or vice-versa, using any suitable transformation techniques. Thus, in some embodiments, each registered local virtual reference LVR has X, Y,Z coordinates within the CAD coordinate system CCS, which may be stored in a database, table, list, and the like (e.g., on the memory device 112). One example of the translation or transformation of data between coordinate systems is described in U.S. Pat. No. 8,675,939, entitled "Registration of Anatomical Data Sets", the disclosure of which is hereby incorporated by reference in its entirety.

Figure 19A:
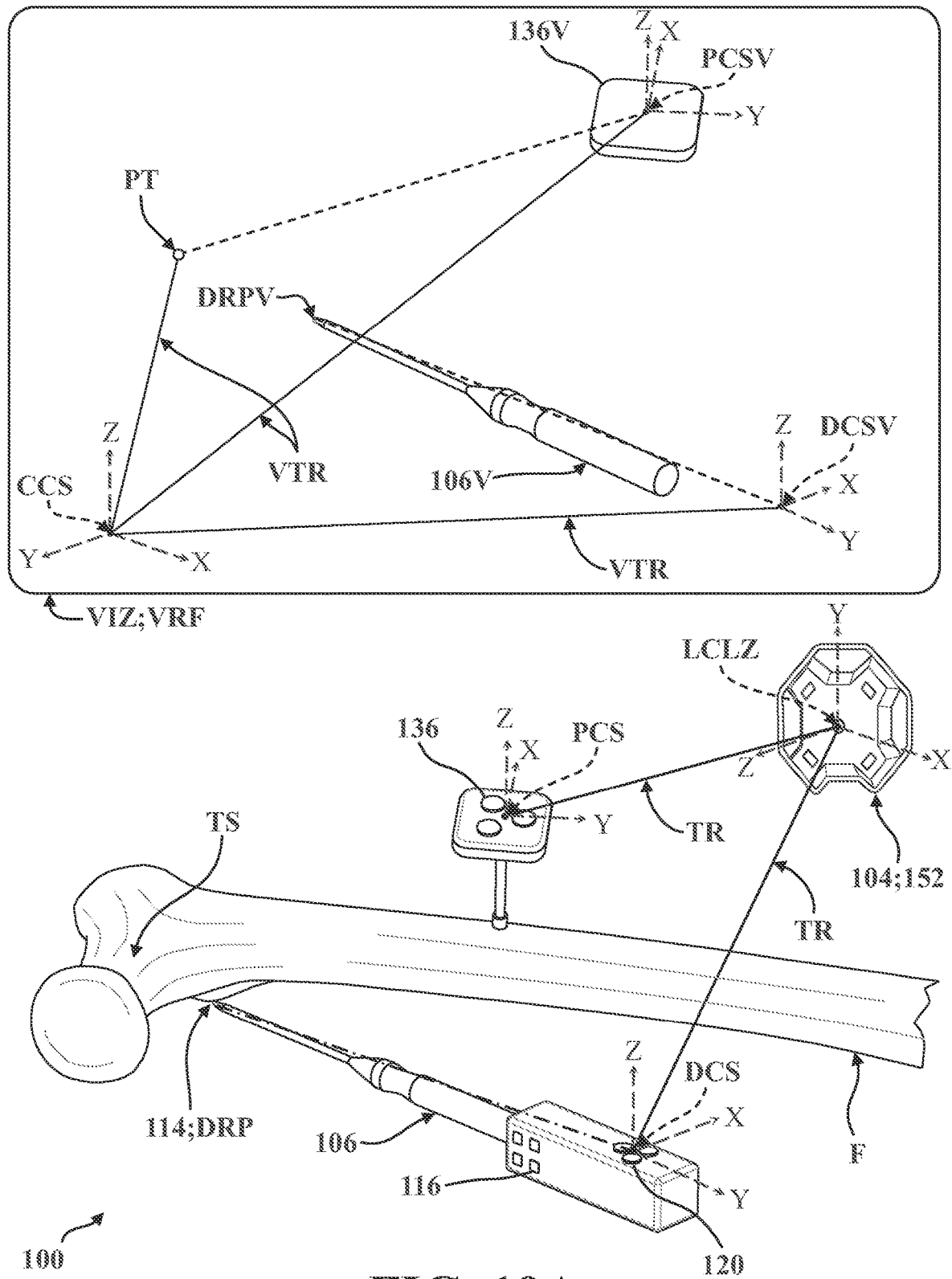
FIG. 19A is a partial perspective view of the localizer, the digitization device, the patient tracker, and the femur of FIG. 18 shown adjacent to a visualization of a virtual reference frame rendered with the CAD program of FIG. 2, the visualization illustrating transforms between a CAD coordinate system and virtual representations of the patient tracker and the digitization device rendered within the visualization based on tracked states of the digitization device and the patient tracker, and further shown illustrating transforms between the CAD coordinate system and a registered local virtual reference previously-established as a point representing the saddle point landmark of the femur.

To illustrate the concept of translating between the localizer coordinate system LCLZ and the CAD coordinate system CCS, FIG. 19A shows the localizer 152, the first patient tracker 136 fixed to the femur F adjacent the target site TS, and the digitization device 106 arranged with the pointer tip 114 at the trochanter minor of the femur F. Here, transforms TR are shown generically between the localizer coordinate system LCLZ and the digitizer coordinate system DCS, and between the localizer coordinate system LCLZ and the patient coordinate system PCS.

FIG. 19A also shows the corresponding visualization VIZ of the virtual reference frame VRF rendered by the CAD program 102 on one of the display units 148. The visualization VIZ depicted in FIG. 19A shows the CAD coordinate system CCS, the virtual digitization device 106V, and the virtual first patient tracker 136V. Moreover, the visualization VIZ depicted in FIG. 19A also shows the virtual digitizer coordinate system DCSV associated with the virtual digitization device 106V, and the virtual patient coordinate system PCSV associated with the virtual first patient tracker 136V. Here, virtual transforms VTR are shown generically (represented with solid lines) between the CAD coordinate system CCS and the virtual digitizer coordinate system DCSV, and between the CAD coordinate system CCS and the virtual patient coordinate system PCSV. Thus, by tracking states of the trackers 120, 132, 136, 138, 142 within the localizer coordinate system LCLZ, transforms TR with respect to the localizer coordinate system LCLZ can be translated into related virtual transforms VTR with respect to the CAD coordinate system CCS, and vice-versa.

Furthermore, because the position of the pointer tip 114 (which defines the digitizer reference point DRP) is known relative to the pointer tracker 120 (which defines the digitizer coordinate system DCS), and because the pointer tracker 120 is tracked by the navigation system 104 within the localizer coordinate system LCLZ, the navigation controller 146 (and/or the computing device 108) can translate coordinates of the digitizer reference point DRP from the localizer coordinate system LCLZ into corresponding coordinates of a local virtual reference LVR within the CAD coordinate system CCS, thereby facilitating registration of local virtual references LVR within the virtual reference frame VRF.

Put differently, in order to register a local virtual references LVR within the virtual reference frame VRF of the CAD program 102, the surgeon can activate the pointer control input 116 of the digitization device 106 to establish a coordinate point associated with the position of the pointer tip 114 within the localizer coordinate system LCLZ (e.g., at a portion of the patient's anatomy at the target site TS). Here, activation of the pointer control input 116 facilitates determining coordinates of the digitizer reference point DRP within the localizer coordinate system LCLZ, and those coordinates can be translated to the CAD coordinate system CCS and registered as a local virtual reference LVR within the virtual reference frame VRF of the CAD program 102.

With continued reference to FIGS. 1 and 18-19A, it will be appreciated that the CAD coordinate system CCS may be arbitrary and may not necessarily correspond to the localizer coordinate system LCLZ in certain embodiments. By way of illustrative example, two registered local virtual references LVR within the virtual reference frame VRF may be positioned arbitrarily with respect to the CAD coordinate system CCS, but may be positioned relative to one another within the CAD coordinate system CCS in a way which corresponds to the respective positions that the digitizer reference point DRP was at within the localizer coordinate system LCLZ when the local virtual references LVR were established.

Furthermore, different registered local virtual references LVR can be associated with (or transformed dynamically relative to) other coordinate systems within the virtual reference frame VRF in some embodiments. By way of illustrative example, different local virtual references LVR (and/or geometrical design objects GDO arranged relative thereto) may be associated with respectively different parts of the patient's anatomy relative to the target site TS (e.g., some with the tibia T and some with the femur F) such that relative movement between the different parts of the patient's anatomy results in corresponding relative movement between the different local virtual references LVR (and/or geometrical design objects GDO arranged relative thereto). Here, it will be appreciated that relative movement between any of the trackers 120, 132, 136, 138, 142 with respect to the localizer coordinate system LCLZ may be rendered, represented, or otherwise observed within the virtual reference frame VRF as corresponding relative movement with respect to the CAD coordinate system CCS.

Figure 6:
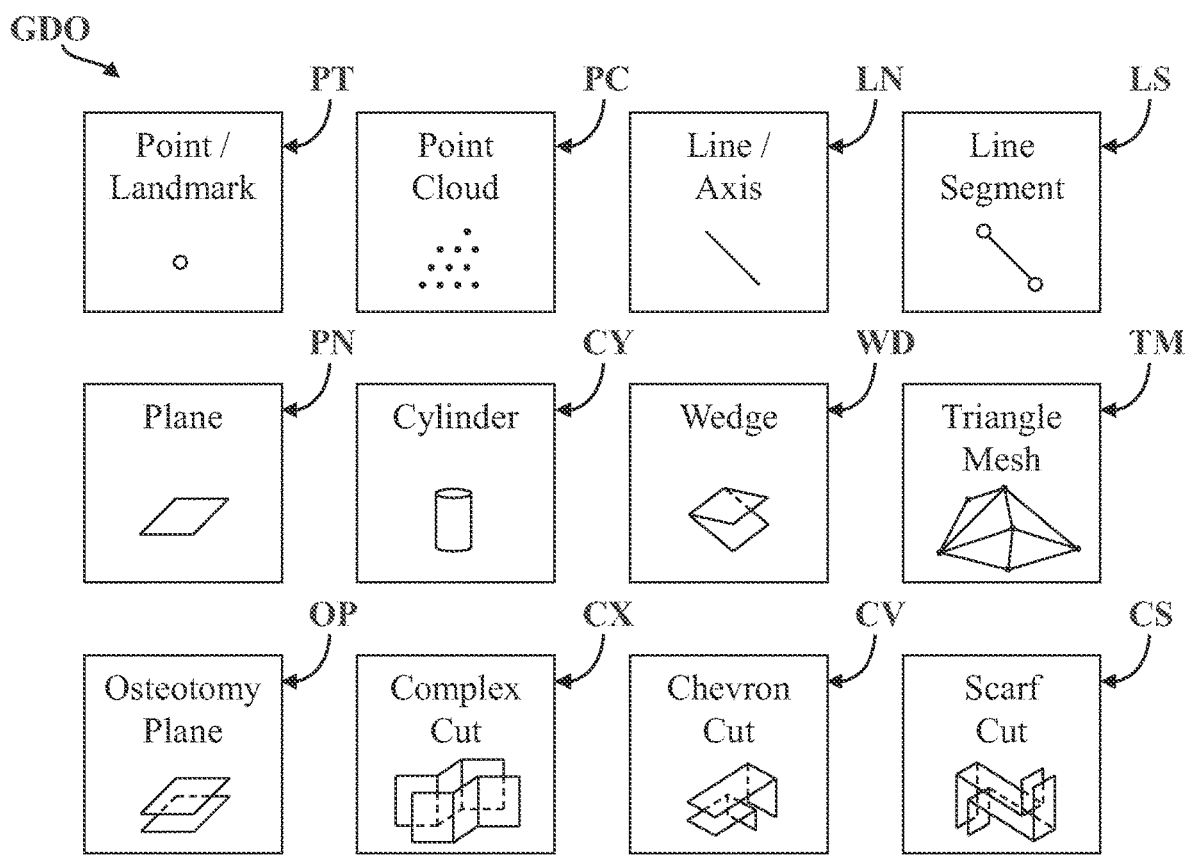
FIG. 6 depicts different types of geometrical design objects which can be arranged within a virtual reference frame of the CAD program of FIG. 2.

Referring now to FIG. 6, various different example geometrical design objects GDO which can be arranged within the virtual reference frame VRF with the CAD program 102 are shown. The illustrated geometrical design objects GDO include a point PT (or "landmark"), a point cloud PC, a line LN (or "axis"), a line segment LS, a plane PN, a cylinder CY, a wedge WD, a triangle mesh TM, an osteotomy plane OP, a complex cut CX, a chevron cut CV, and a scarf cut CS. As will be appreciated from the subsequent description below, each of the geometrical design objects GDO introduced above can be arranged within the virtual reference frame VRF in a number of different ways, and in connection with ad-hoc intraoperative planning a number of different types of surgical steps.

As is explained in greater detail below, the CAD program 102 is configured to facilitate arranging the various geometrical design objects GDO within the virtual reference frame VRF based on geometric relationships with respect to one or more registered local virtual references LVR, and/or one or more calculated virtual references CVR derived from one or more registered local virtual references LVR. Each type of geometrical design object GDO must be "defined," "constrained," or "fixed" by a minimum (and sometimes maximum) number of registered local virtual references LVR and/or calculated virtual references CVR.

For the purposes of clarity and consistency, in order to illustrate the concept of "defining" geometrical design objects GDO, the term "virtual reference(s)" will occasionally be used herein to refer to either registered local virtual references LVR or calculated virtual references CVR. Here, a "virtual reference" may be considered as a set of X, Y, Z coordinates within the virtual reference frame VRF.

Points PT are the most primitive type of geometrical design object GDO and are defined with (and are synonymous to) a single virtual reference. Thus, whenever a registered local virtual reference LVR is established using the digitization device 106, and/or whenever a calculated virtual reference CVR is established (e.g., derived from one or more registered local virtual references LVR), a point PT may be created and serve as a geometrical design object GDO arranged within the virtual reference frame VRF. In the embodiments illustrated throughout the drawings and described herein, the term "registered local virtual reference LVR" is generally used to described a points PT which has been established using the digitization device 106. Furthermore, as used herein, the term "landmark" generally refers to a specific portion of the patient's anatomy at or adjacent to the target site TS which is associated with a specific point PT.

Lines LN and line segments LS are each defined with two virtual references. As illustrated herein, line segments LS comprise a length extending between a pair of points PT, whereas lines LN may have an infinite length (and may also be referred to as "axes").

In general terms, planes PN are defined with three virtual references. However, and as is described in greater detail below, the CAD program 102 of the present disclosure utilizes planes PN as two-dimensional polygons that have three or more sides symmetrically arranged at a span length SL about an object index OI. The object index OI of planes PN (and certain other geometrical design objects GDO) is analogous to a coordinate system within the virtual reference frame VRF (see, for example, FIGS. 9A-17). As will be appreciated from the subsequent description below, this configuration affords the ability to quickly define additional geometrical design objects GDO from planes PN, such as using a corner of the plane PN as a point PT (or as a calculated virtual reference CVR), using an edge of the plane PN as a line segment LS (or as two calculated virtual references CVR), and the like.

As is described in greater detail below, in some embodiments, the CAD program 102 is configured to enable construction of compound objects from one or more geometrical design objects GDO arranged within the virtual reference frame VRF. For example, and with continued reference to FIG. 6, point clouds PC are comprised of multiple points PT, each of which may be defined by a single virtual reference. Cylinders CY are volumes which, in general terms, are defined based on the specific geometric properties of the volume (e.g., selecting a diameter with the CAD program 102) relative to multiple virtual references. Wedges WD may be represented by two square-shaped planes PN which share a common edge and may open symmetrically or asymmetrically, or may be constructed as compound objects such as from two planes PN of different shapes. Triangle meshes TM are compound objects realized as surfaces defined by multiple points PN, such as from a point cloud PC. Osteotomy planes OP are compound objects and are defined by a pair of parallel planes PN spaced from each other at a cut distance. Complex cuts CX, chevron cuts CV, and scarf cuts CS are each compound objects and are generally defined by parallel sets of multiple planes PN which share common edges.

It will be appreciated that the geometrical design objects GDO described herein and illustrated throughout the drawings are non-limiting, and other different geometrical design objects GDO may be utilized in certain embodiments. By way of non-limiting example, geometrical design objects GDO may be realized as assemblies of one or more previously-generated geometrical design objects GDO which are utilized in a subsequent surgical procedure (e.g., the CAD program 102 may facilitate saving, importing, exporting, and the like). Other configurations are contemplated.

Referring now to FIG. 2, as noted above, the CAD program 102 is stored on the memory device 112 of the computing device 108 and is executed by the processor 110. The processor 110 may include a microprocessor, a microcontroller, or the like. The memory device 112 is a non-transitory computer-readable storage medium that stores computer-readable and executable instructions embodied in one or more programs or modules. The memory device 112 may include, for example, non-volatile memory such as a hard disk or flash memory, and may also include random access memory (RAM), which can include non-volatile RAM (NVRAM), magnetic RAM (MRAM), ferroelectric RAM (FeRAM), or any other suitable memory.

In some embodiments, the computing device 108 is configured to communicate with one or more of the display units 148, the navigation controller 146, the tool controller 130, and/or the pointer controller 118. As noted above, in some embodiments, the computing device 108 is realized with the navigation controller 146 or is incorporated into the navigation controller 146. In another embodiment, the computing device 108 is a separate computer, device, and the like. In yet another embodiment, the computing device 108 forms part of a portable electronic device 162 (e.g., a tablet computer). Other configurations are contemplated.

Referring now to FIG. 3, an example software architecture of the CAD program 102 is shown with various modules employed to facilitate planning of surgical steps and execution of the surgical procedure, as noted above and as described in greater detail below. These modules include a point cloud toolkit 164, a medical imaging toolkit 166, a mathematical toolkit 168, a physics toolkit 170, a graphical user interface (GUI) 172, and a module for CAD functions and algorithms 174 (hereinafter "algorithm module"). Also shown in FIG. 3 are representations of visualization data VZ which may be available during planning of surgical steps, and tool control data CZ which may be utilized during execution of the surgical procedure, both of which will be described in greater detail below.

The point cloud toolkit 164 is employed in certain embodiments to facilitate mapping point clouds PC to anatomical structures or other geometrical design objects GDO. The point cloud toolkit 164 may include algorithms that enable the CAD program 102 to generate triangle meshes TM or other surfaces, and/or to define a point cloud PC generated using the digitization device 106 relative to an appropriate geometrical design object GDO arranged in the virtual reference frame VRF. Other configurations are contemplated.

The medical imaging toolkit 166 comprises a set of software tools which, among other things: enable the segmentation, registration, and display of portions of the patient's anatomy; enable 3D graphics processing, image processing, and visualization; provide an application framework; facilitate operation of the GUI 172; and facilitate implementation of the algorithm module 174. In one embodiment, the medical imaging toolkit 166 comprises or is based on one or more open-source frameworks known in the art, such as the Medical Imaging Interaction Toolkit (MITK), the Insight Segmentation and Registration Toolkit (ITK), and/or the Visualization Toolkit (VTK). Other configurations are contemplated.

The mathematical toolkit 168 may include a linear algebra library that may be utilized for pattern recognition, signal processing, and the like. In some embodiments, the mathematical toolkit 168 may facilitate arranging or moving geometrical design objects GDO within the virtual reference frame VRF (e.g., rotation, translation, and the like). In one embodiment, the mathematical toolkit 168 comprises or is based on one or more open-source C++ libraries known in the art, such as Armadillo, and/or Boost. Other configurations are contemplated.

The physics toolkit 170 may include a library that helps facilitate simulation of and/or execution of the surgical procedure (e.g., based on collision detection, rigid body dynamics, and the like), such as may be used to define virtual boundaries with geometrical design objects GDO arranged within the virtual reference frame VRF that are used to generate tool control data CZ communicated to and interpreted by the tool controller 130 of the surgical tool 122, as noted above and as is described in greater detail below in connection with FIGS. 27-49. In one embodiment, the physics toolkit 170 comprises or is based on one or more open-source physics engines known in the art, such as Bullet. Other configurations are contemplated.

In one embodiment, the GUI 172, which is described in greater detail below in connection with FIGS. 5, 7, and 20A-26B, comprises or is based on an open-source application framework such as Qt and/or the Qt Modeling Language (QML). Other configurations are contemplated.

Figure 8:
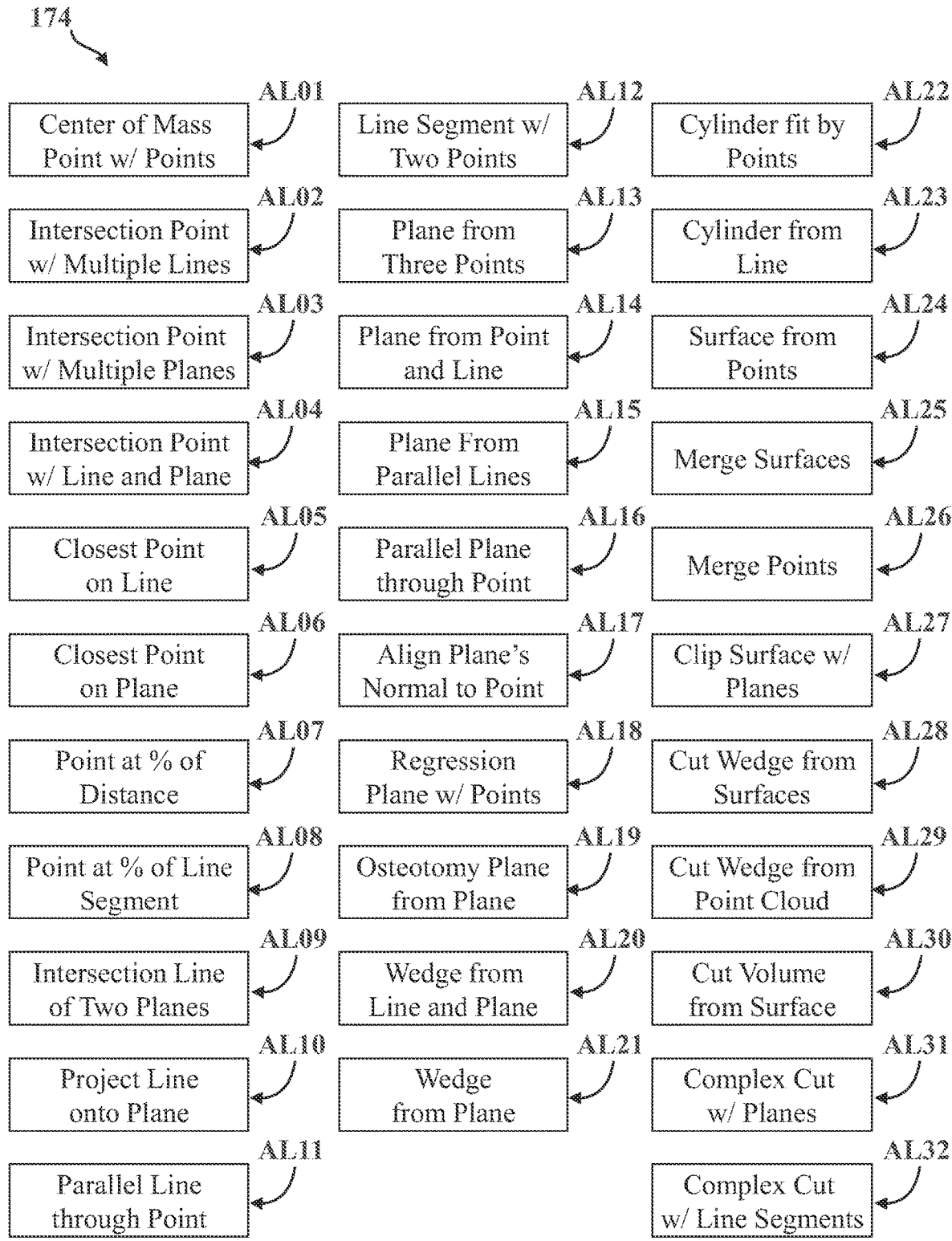
FIG. 8 depicts different algorithms which can be used by the CAD program of FIG. 2 to facilitate arranging geometrical design objects within a virtual reference frame.

Referring now to FIG. 8, various example algorithms of the algorithm module 174 are shown which can be used to facilitate arranging geometrical design objects GDO within the virtual reference frame VRF with the CAD program 102. In some embodiments, the algorithm module 174 comprises or is based on an open-source framework such as the Visualization Toolkit (VTK). Other configurations are contemplated. In the subsequent description of the example algorithms below, the term "pointer tip" will briefly be used herein to refer to the relative position of the digitizer reference point DRP within the virtual reference frame VRF relative to certain geometrical design objects GDO.

A first algorithm AL01 is configured to facilitate arranging a point PT at a center of mass calculated using a plurality of points PT or a point cloud PC.

A second algorithm AL02 is configured to facilitate arranging a point PT at the intersection of a plurality of lines LN and/or line segments LS.

A third algorithm AL03 is configured to facilitate arranging a point PT at the intersection of a plurality of planes PN.

A fourth algorithm AL04 is configured to facilitate arranging a point PT at the intersection of plane PN and a line LN or line segment LS.

A fifth algorithm AL05 is configured to facilitate arranging a point PT along a line LN or a line segment LS based on the closest distance to the pointer tip (e.g., projecting a point PT onto a line LN and moving it along the line LN based on movement of the digitation device 106).

A sixth algorithm AL06 is configured to facilitate arranging a point PT along a plane PN based on the closest distance to the pointer tip (e.g., projecting a point PT onto a plane PN and moving it about the plane PN based on movement of the digitation device 106).

A seventh algorithm AL07 is configured to facilitate arranging a point PT at a percentage of distance between: the pointer tip; and a local virtual reference LVR, or a calculated virtual reference CVR (e.g., positioning a point PT halfway between the pointer tip and a registered local virtual reference LVR).

An eighth algorithm AL08 is configured to facilitate arranging a point PT at a percentage of distance along a line segment LS (e.g., positioning a point PT halfway between two registered local virtual references LVR used to construct or define the line segment LS).

A ninth algorithm AL09 is configured to facilitate arranging a line LN or a line segment LS at the intersection of two planes PN.

A tenth algorithm AL10 is configured to facilitate arranging a line LN projected onto a plane PN (e.g., projecting a line LN onto a plane PN and moving it about the plane PN based on movement of the digitation device 106).

An eleventh algorithm AL11 is configured to facilitate arranging a line LN through a point PT which is parallel to another line LN within the virtual reference frame VRF.

A twelfth algorithm AL12 is configured to facilitate arranging a line segment LS between two points PT.

A thirteenth algorithm AL13 is configured to facilitate arranging a plane PN from three points PT.

A fourteenth algorithm AL14 is configured to facilitate arranging a plane PN from a point PT and a line LN or a line segment LS (e.g., with a normal vector of the plane PN arranged perpendicular to the line LN and with the object index OI of the plane PN positioned at the point PT).

A fifteenth algorithm AL15 is configured to facilitate arranging a plane PN from two parallel lines LN and/or line segments LS (e.g., with the plane PN arranged coincident with both lines LN).

A sixteenth algorithm AL16 is configured to facilitate arranging a plane PN through a point PT which is parallel to another plane PN within the virtual reference frame VRF.

A seventeenth algorithm AL17 is configured to facilitate aligning a plane PN normal to a point PT (e.g., with a normal vector of the plane PN intersecting the point PT).

An eighteenth algorithm AL18 is configured to facilitate arranging a plane PN through a plurality of points PT or a point cloud PC (e.g., by calculating a regression plane through a point cloud PC).

A nineteenth algorithm AL19 is configured to facilitate arranging an osteotomy plane OP from a plane PN (e.g., by creating a plane PN which is parallel to and is spaced from another plane PN within the virtual reference frame VRF at a cut distance).

A twentieth algorithm AL20 is configured to facilitate arranging a wedge WD from a line LN and a plane PN (e.g., by creating a plane PN which is coincident with a line LN within the virtual reference frame VRF and which intersects another plane PN within the virtual reference frame VRF).

A twenty-first algorithm AL21 is configured to facilitate arranging a wedge WD from a plane PN (e.g., by creating a plane PN which shares an edge with another plane PN within the virtual reference frame VRF).

A twenty-second algorithm AL22 is configured to facilitate arranging a cylinder CY from a plurality of points PT or a point cloud PC (e.g., by calculating a line LN through a point cloud PC and arranging a cylinder CY concentrically to the line LN).

A twenty-third algorithm AL23 is configured to facilitate arranging a cylinder CY from a line LN or a line segment LS (e.g., by arranging a cylinder CY concentrically to the line LN or line segment LS).

A twenty-fourth algorithm AL24 is configured to facilitate defining a surface from a plurality of points PT or a point cloud PC (e.g., by creating triangle mesh TM from a point cloud PC).

A twenty-fifth algorithm AL25 is configured to facilitate merging multiple surfaces (e.g., to construct a volume using a triangle mesh TM and one or more planes PN).

A twenty-sixth algorithm AL26 is configured to facilitate merging points PT (e.g., merging two point clouds PC into a single point cloud PC, or merging a point cloud PC with additional points PT).

A twenty-seventh algorithm AL27 is configured to facilitate clipping a surface with one or more planes PN (e.g., removing points PT of a triangle mesh TM above or below a plane PN which intersects the triangle mesh TM).

A twenty-eighth algorithm AL28 is configured to facilitate cutting a wedge WD out from surfaces (e.g., removing points PT of a triangle mesh TM above or below planes PN which share a common edge to form a wedge WD).

A twenty-ninth algorithm AL29 is configured to facilitate cutting a wedge WD out from a point cloud PC (e.g., removing points PT of a point cloud PC above or below planes PN which share a common edge to form a wedge WD).

A thirtieth algorithm AL30 is configured to facilitate cutting a volume from a surface (e.g., removing points PT of a triangle mesh TM relative to a cylinder CY which intersects the triangle mesh TM).

A thirty-first algorithm AL31 is configured to facilitate creating complex cuts CX from planes PN (e.g., creating a set of multiple planes PN which share common edges where the set is parallel to and spaced from another set of multiple planes PN which share common edges).

A thirty-second algorithm AL32 is configured to facilitate creating complex cuts CX from line segments LS (e.g., creating a set of multiple planes PN which share a common edge defined by a line segment LS and creating another set of multiple planes PN which is parallel to and spaced from the first set).

It will be appreciated that the algorithms described above are non-limiting examples of the functionality of the algorithm module 174 of the CAD program 102.

Figure 5:
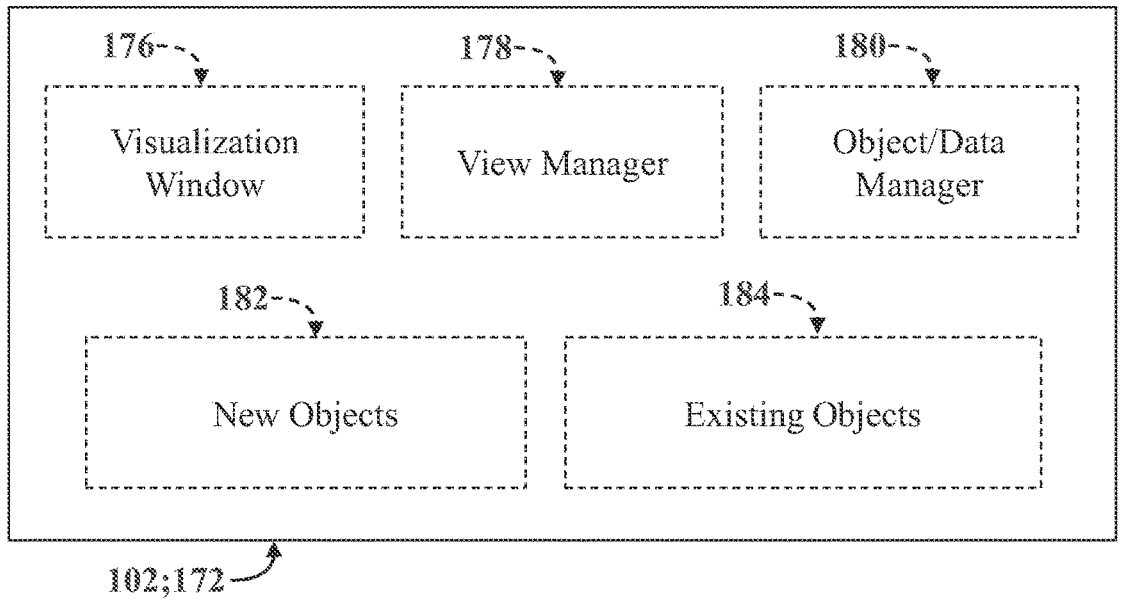
FIG. 5 is a block diagram illustrating aspects of a graphical user interface (GUI) for use in arranging different geometrical design objects within a virtual reference frame with the CAD program of FIG. 2 to plan a surgical step according to one embodiment of the present disclosure.

Referring now to FIG. 5, as noted above, the CAD program 102 comprises the GUI 172 in the illustrated embodiment, which may be presented to the surgeon on the one or more display units 148 and may be navigated using the one or more control inputs 150 and/or the digitization device 106. The GUI 172 generally comprises a visualization window 176, a view manager 178, an object/data manager 180, a new object arrangement section 182, and an existing object arrangement section 184, each of which will be described in greater detail below in connection with FIGS. 20A-26B.

Figure 7:
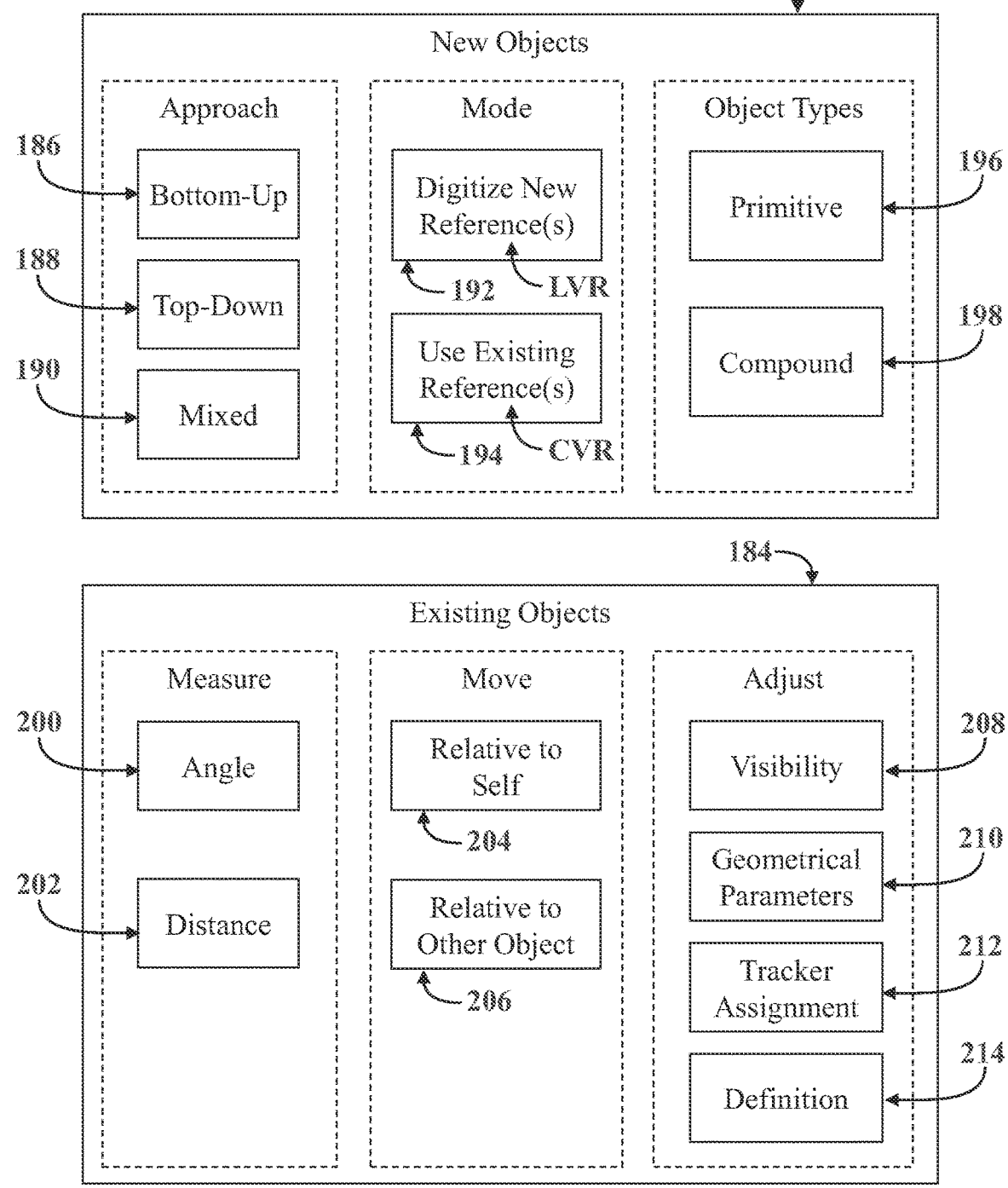
FIG. 7 depicts different aspects of the CAD program of FIG. 2 which can be used to facilitate arranging geometrical design objects within a virtual reference frame.

Referring now to FIG. 7, aspects of the new object arrangement section 182 and the existing object arrangement section 184 are shown. In the new object arrangement section 182, three general approaches that can be utilized in arranging new geometrical design objects GDO in order to facilitate planning the surgical step are represented: a bottom-up approach 186, a top-down approach 188, and a mixed approach 190. These approaches 186, 188, 190 generally described the different workflows which may be utilized for any given surgical procedure. Put differently, the approaches 186, 188, 190 describe different sequences in which new geometrical design objects GDO can generally be created and arranged within the virtual reference frame VRF.

By way of brief, illustrative example, a bottom-up approach 186 may involve the surgeon selecting an option to create new points PT by establishing registered local virtual references LVR, selecting an option to create a new line segment LS using the points PT, and selecting an option to create a new osteotomy plane OP using the line segment LS. Conversely and also by way of brief, illustrative example, a top-down approach 188 may involve the surgeon selecting an option to create a new osteotomy plane OP without having yet established any local virtual references LVR. Here, the GUI 172 could present the surgeon with different ways to arrange the new osteotomy plane OP, such as with an option to create the new osteotomy plane OP from a line segment LS. If this option were selected, the GUI 172 could prompt the surgeon to establish and register the requisite local virtual references LVR needed to define the line segment LS.

A mixed approach 190 is a hybrid of the bottom-up approach 186 and the top-down approach 188, and involves the GUI 172 providing the surgeon with contextual options for creating new geometrical design objects GDO based on the types of different geometrical design objects GDO which have already been arranged within the virtual reference frame VRF and/or the based on the presence of registered local virtual references LVR which have already been established using the digitization device 106.

It will be appreciated that any one of the approaches 186, 188, 190 may be utilized for a particular surgical procedure, and may be defined or implemented in certain embodiments in ways which guide the surgeon through a particular surgical procedure. To this end, specific workflows, macros, and the like could be employed by the CAD program 102 to prompt the surgeon to arrange geometrical design objects GDO sequentially in a predetermined order and/or with a contextual surgical meaning.

For example, the CAD program 102 could employ a macro for intraoperatively planning a femoral neck osteotomy with a bottom-up approach 186 and could sequentially: prompt the surgeon to establish a local virtual reference LVR at a saddle point landmark LM_SP of the femur F, subsequently prompt the surgeon to establish a local virtual reference LVR at a trochanter minor landmark LM_TM of the femur F, and then automatically arrange a line segment LS between the registered local virtual references LVR established at the saddle point landmark LM_SP and the trochanter minor landmark LM_TM, and so on. It will be appreciated that the forgoing example is an illustrative and incomplete description of initial surgical steps which may be associated with performing a femoral neck osteotomy with a bottom-up approach 186 and with contextual surgical meaning (e.g., prompting the surgeon to perform a step with respect to a specific part of the patient's anatomy relative to the target site TS). Additional examples of each type of approach 186, 188, 190 are described below in connection with FIGS. 20A-26B.

With continued reference to FIG. 7, as noted above, aspects of the new object arrangement section 182 and the existing object arrangement section 184 are shown. In the new object arrangement section 182, two general modes that can be utilized in creating new geometrical design objects GDO in order to facilitate planning the surgical step are represented: a digitize new references mode 192, and a use existing references mode 194. These modes 192, 194 represent the different ways in which new geometrical design objects GDO can be created and/or arranged within the virtual reference frame VRF, and may each be utilized with any of the approaches 186, 188, 190 introduced above.

The digitize new references mode 192 is utilized where the geometrical design object GDO is constructed using registered local virtual references LVR which are sequentially-established with the digitization device 106 without reliance on previously-established local virtual references LVR. For example, a line segment LS may be constructed using the digitize new references mode 192 by the surgeon selecting an option to create the line segment LS and (using a top-down approach 188) the CAD program 102 would prompt the surgeon to sequentially establish two new local virtual references LVR (each represented as a point PT) which, once registered, then define the line segment LS.

The use existing references mode 194 is utilized where the geometrical design object GDO is constructed from (or based on) a previously-constructed geometrical design object GDO arranged within the virtual reference frame VRF. Here, one or more local virtual references LVR associated with the previously-constructed geometrical design object GDO are shared with the new geometrical design object GDO. In some embodiments, the new geometrical design object GDO may share one or more local virtual references LVR with one or more previously-constructed geometrical design objects GDO, and the surgeon could use the digitization device 106 to establish and register one or more additional local virtual references LVR to fully define the new geometrical design object GDO. In other embodiments, the new geometrical design object GDO may share one or more local virtual references LVR with one or more previously-constructed geometrical design objects GDO, and the surgeon would then use the CAD program 102 to derive (e.g., using the algorithms module 174) and register one or more calculated virtual references CVR to fully define the new geometrical design object GDO. It will be appreciated that the forgoing examples are illustrative and non-limiting.

With continued reference to FIG. 7, in the new object arrangement section 182, two general types of new geometrical design objects that can be constructed with the CAD program 102 in order to facilitate planning the surgical step are represented: a primitive type object 196, and a compound type object 198. In general, primitive type objects 196 are geometrical design objects GDO which may be used to construct compound type objects 198.

In some embodiments, primitive type objects 196 comprise points, lines, planes, and volumes which are utilized as "construction objects" in order to assemble compound type objects 198. In some embodiments, compound type objects 198 may be used to assemble other compound type objects 198. It will be appreciated that these descriptions are utilized herein for illustrative purposes, and that certain types of geometrical design objects GDO could be realized as either primitive type objects 196 or as compound type objects 198 in certain embodiments.

For example, a wedge WD could be realized as a primitive type object 196 that is selectable for construction using a top-down approach 188 where the CAD program 102 guides the surgeon through either of the modes 192, 194 described above to fully define the wedge WD. Alternatively, a wedge WD could be realized as a compound type object 198 that is constructed using a bottom-up approach 186 where the surgeon fully defines one plane PN and then uses one of its edges to define another plane PN, where both fully-defined planes PN are assembled to define the wedge WD as a compound type object 198. Here too it will be appreciated that the forgoing examples are illustrative and non-limiting.

With continued reference to FIG. 7, as noted above, aspects of the new object arrangement section 182 and the existing object arrangement section 184 are shown. In the existing object arrangement section 184, two general types of measurements that can be utilized in connection with existing geometrical design objects GDO in order to facilitate planning the surgical step are represented: angle measurements 200 and distance measurements 202. Here, the CAD program 102 is configured to facilitate measuring geometric relationships within the virtual reference frame VRF between: geometrical design objects GDO; registered local virtual references LVR; calculated virtual references CVR; and/or other contents of the virtual reference frame VRF (e.g., with respect to different transformations or coordinate systems, virtual representations of tools, trackers, pointers, and the like). In some embodiments, angle measurements 200 and/or distance measurements 202 may be performed using aspects of the mathematical toolkit 168.

In the existing object arrangement section 184, two general options that can be utilized in moving existing geometrical design objects GDO within the virtual reference frame VRF in order to facilitate planning the surgical step are represented: a relative to self option 204, and a relative to other object option 206.

Figure 10A:
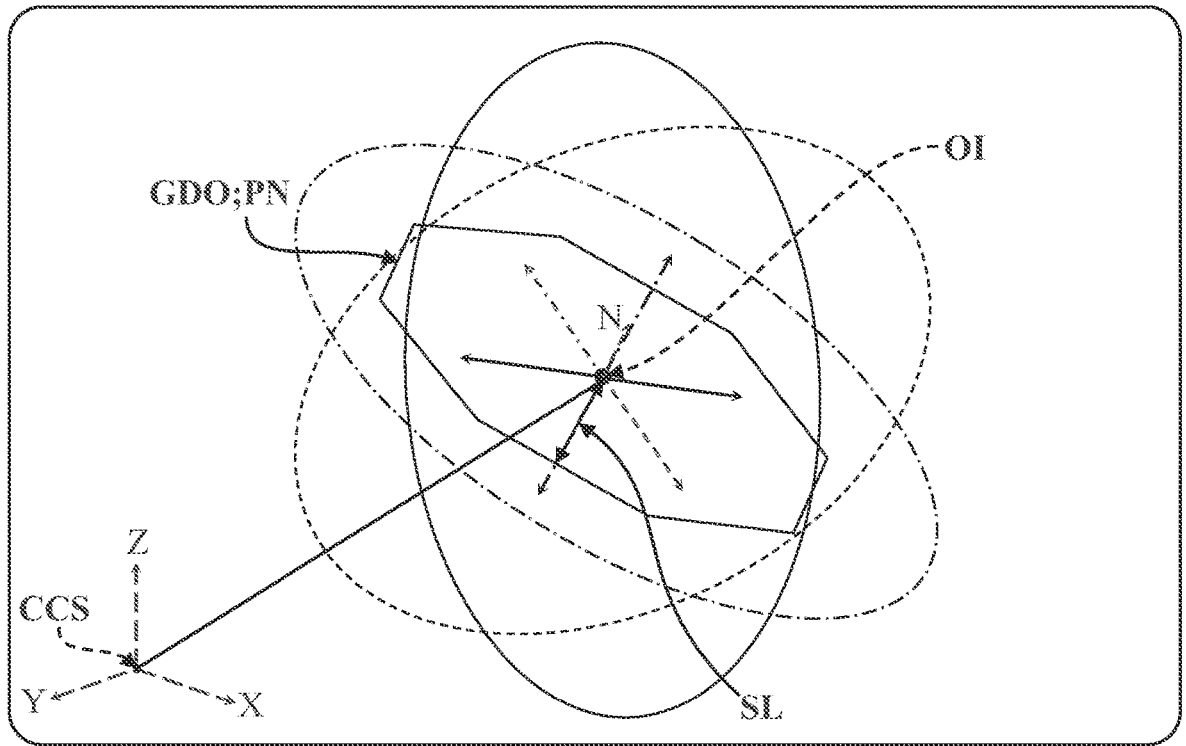
FIG. 10A is another visualization of the virtual reference frame and the geometrical design object of FIG. 9B, shown depicting options for adjusting the pose of the geometrical design object in six degrees of freedom relative to its object index within the virtual reference frame.
Figure 10B:
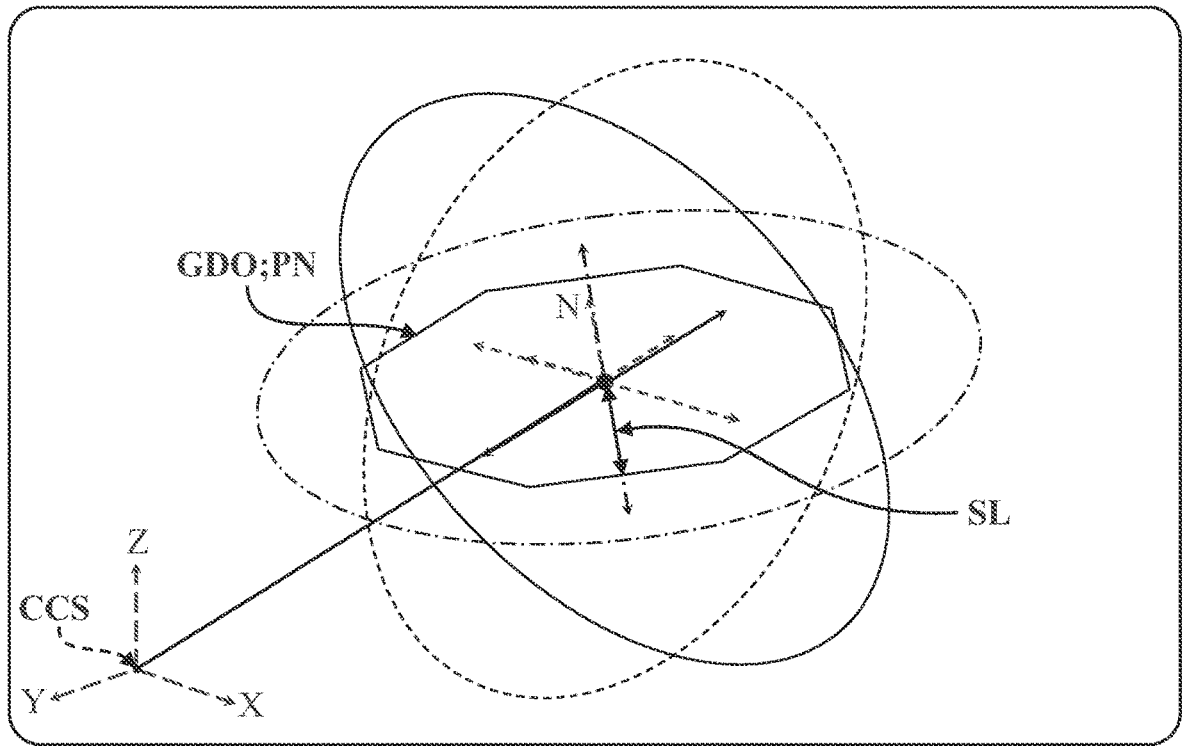
FIG. 10B is another visualization of the virtual reference frame and the geometrical design object of FIG. 10A, shown depicting the geometrical design object in a different pose within the virtual reference frame after having been rotated about its object index.

The relative to self option 204 may be used to adjust the position and/or orientation of an existing geometrical design object GDO within the virtual reference frame VRF based on its current pose. By way of illustrative example, the relative to self option 204 may be used to rotate or translate a geometrical design object GDO about or with respect to its object index OI in one or more degrees of freedom (see FIGS. 10A-10B). In some embodiments, moving a geometrical design object GDO with the relative to self option 204 may create an additional geometrical design object GDO, for example by hiding a pre-movement geometrical design object GDO and utilizing the local virtual references LVR associated with the hidden pre-movement geometrical design object as calculated virtual references CVR for the post-movement geometrical design object GDO. In this illustrative example, the plane PN depicted in FIG. 10A represents a pre-movement geometrical design object GDO, and the plane PN depicted in FIG. 10B represents a post-movement geometrical design object GDO.

The relative to other object option 206 may be used to adjust the position and/or orientation of an existing geometrical design object GDO within the virtual reference frame based geometrical relationships, such as those described above in connection with angle measurements 200 and/or distance measurements 202. Moreover, existing geometrical design objects GDO can be "constrained" or positioned in particular ways relative to other geometrical design objects GDO, registered local virtual references LVR, and/or calculated virtual references CVR. Some of these constraints and/or geometrical relationships could be based on aspects of or carried out using the algorithms module 174 described above in connection with FIG. 8, and/or the mathematical toolkit 168.

Figure 12:
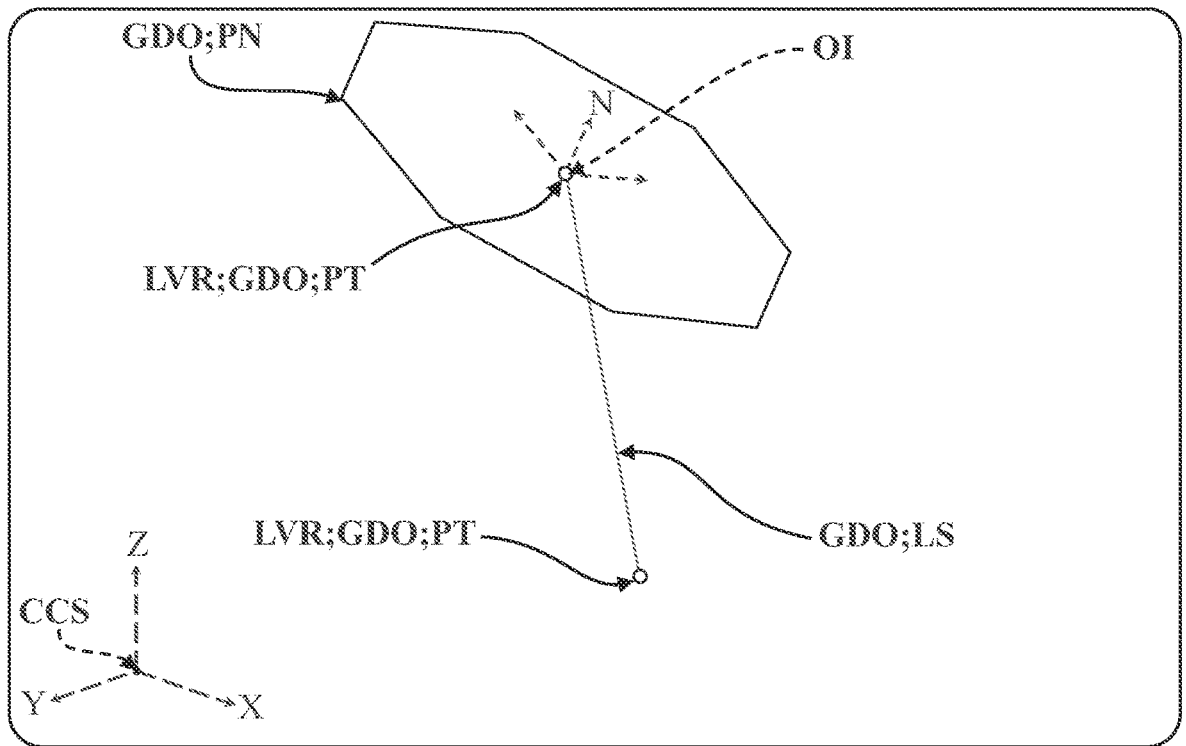
FIG. 12 is a visualization of a virtual reference frame rendered with the CAD program of FIG. 2, shown depicting an example geometrical design object realized as a line segment defined by two registered local virtual references established within the virtual reference frame, and another example geometrical design object realized as an octagonal plane having an object index arranged at one of the registered local virtual references of the line segment.
Figure 13:
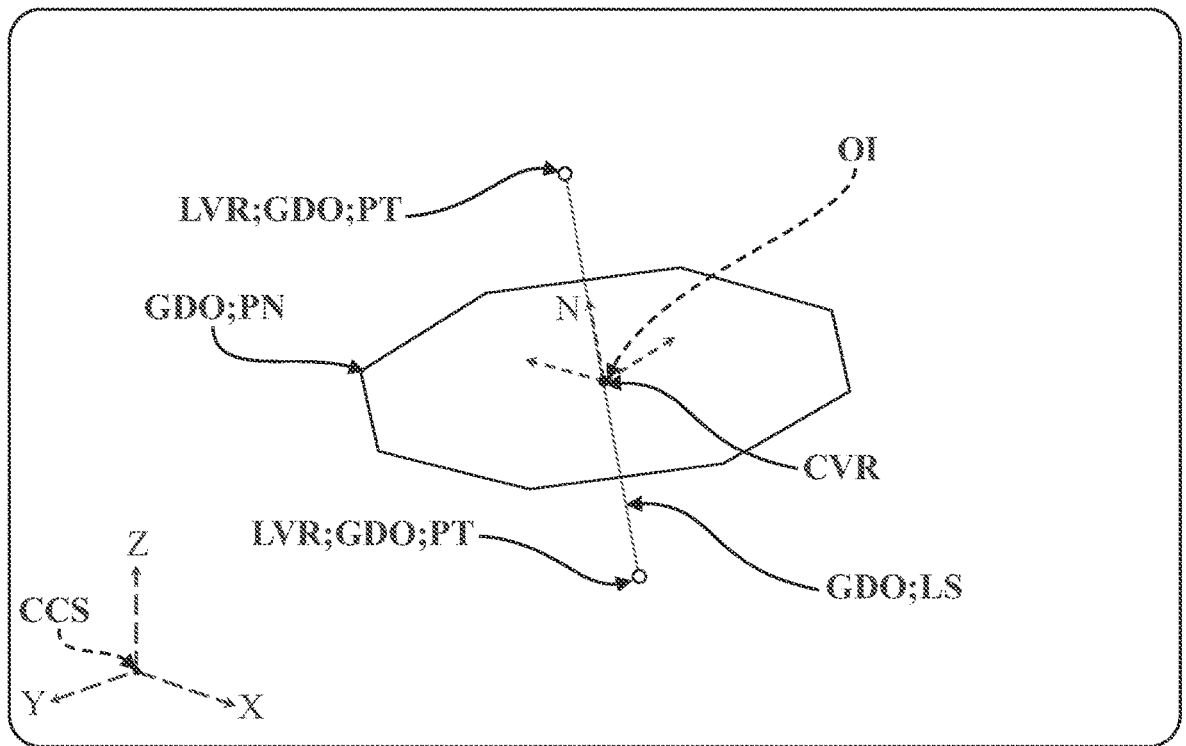
FIG. 13 is another visualization of the virtual reference frame and the geometrical design objects illustrated in FIG. 12, shown depicting the octagonal plane arranged perpendicular to the line segment.

To illustrate examples of constraints, FIG. 12 depicts an octagonal plane PN shown with its object index OI constrained to a point PT of a line segment LS. If desired, the surgeon could rotate the plane PN about its object index OI. By way of further example, FIG. 13 shows the same line segment LS and octagonal plane PN, but with the object index OI of the plane PN positioned midway along the line segment LS and with the object index OI orientated such that the octagonal plane PN (e.g., its normal vector) is perpendicular to the line segment LS. In some embodiments, the arrangement depicted in FIG. 13 may be achieved using the eighth algorithm AL08 to create a calculated virtual reference CVR realized as a point PT midway along the line segment LS, and the seventeenth algorithm AL17 to align the normal vector of the plane PN through the point PT realized with the calculated virtual reference CVR.

Figure 14:
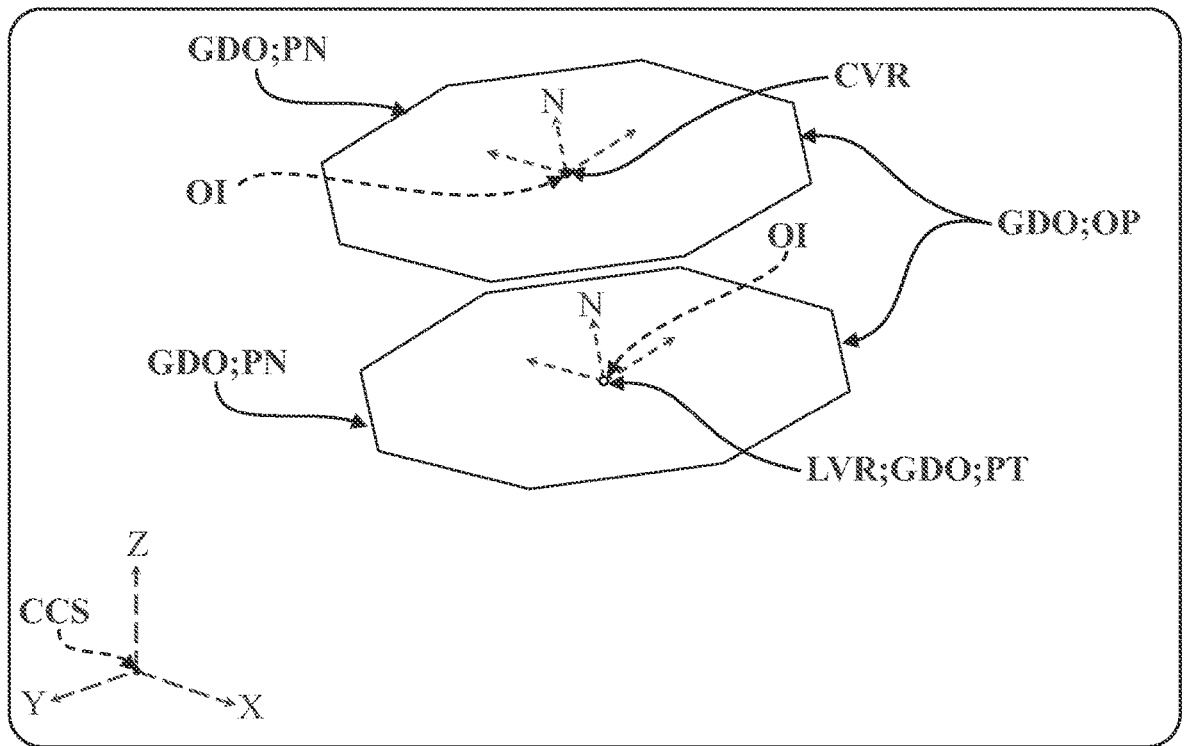
FIG. 14 is a visualization of a virtual reference frame rendered with the CAD program of FIG. 2, shown depicting two example geometrical design objects realized as octagonal planes arranged parallel to each other within the virtual reference frame.

FIG. 14 depicts an example where two octagonal planes PN are arranged parallel to and spaced from each other (e.g., to construct an osteotomy plane OP). In some embodiments, the arrangement depicted in FIG. 14 may be achieved using the nineteenth algorithm AL19 to create one plane PN spaced from and parallel to another plane PN at a cut distance.

Figure 15:
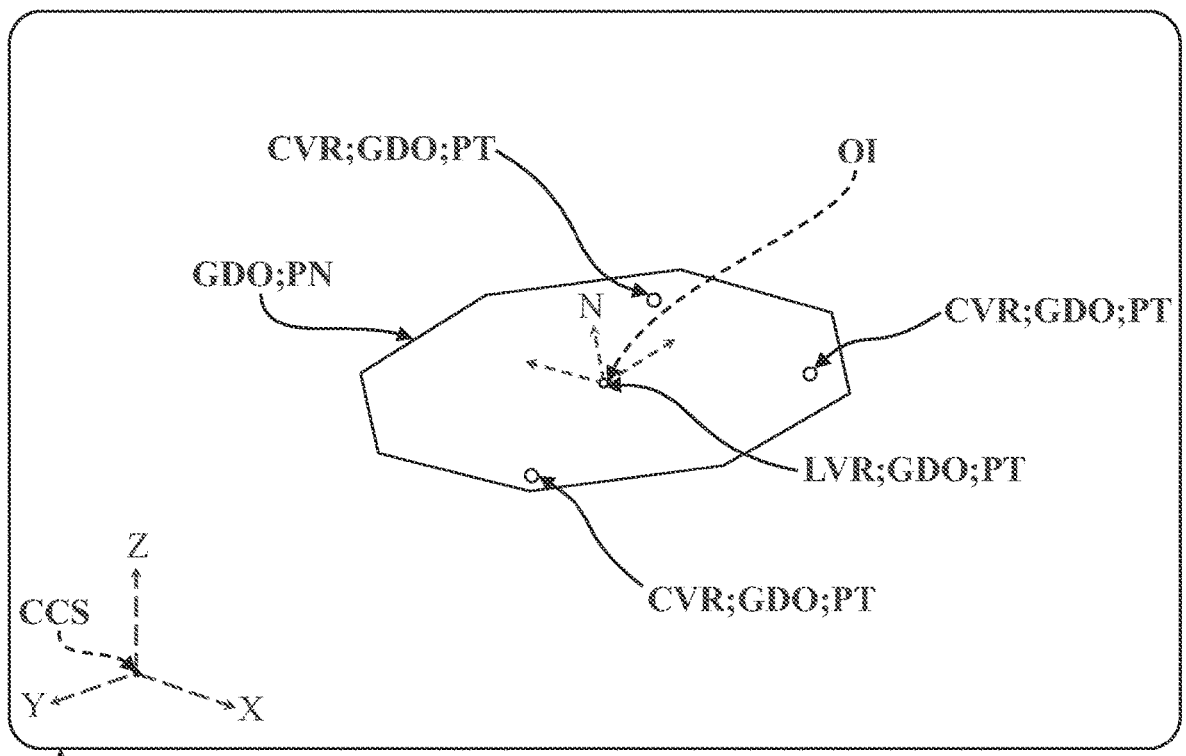
FIG. 15 is a visualization of a virtual reference frame rendered with the CAD program of FIG. 2, shown depicting an example geometrical design object realized as an octagonal plane arranged within the virtual reference frame, and three other example geometrical design objects realized as points arranged as projected onto the octagonal plane.

FIG. 15 depicts an example where three points PT are projected onto an octagonal plane PN. In some embodiments, the arrangement depicted in FIG. 15 may be achieved using the sixth algorithm AL06 to project points PT on the plane PN.

Figure 16:
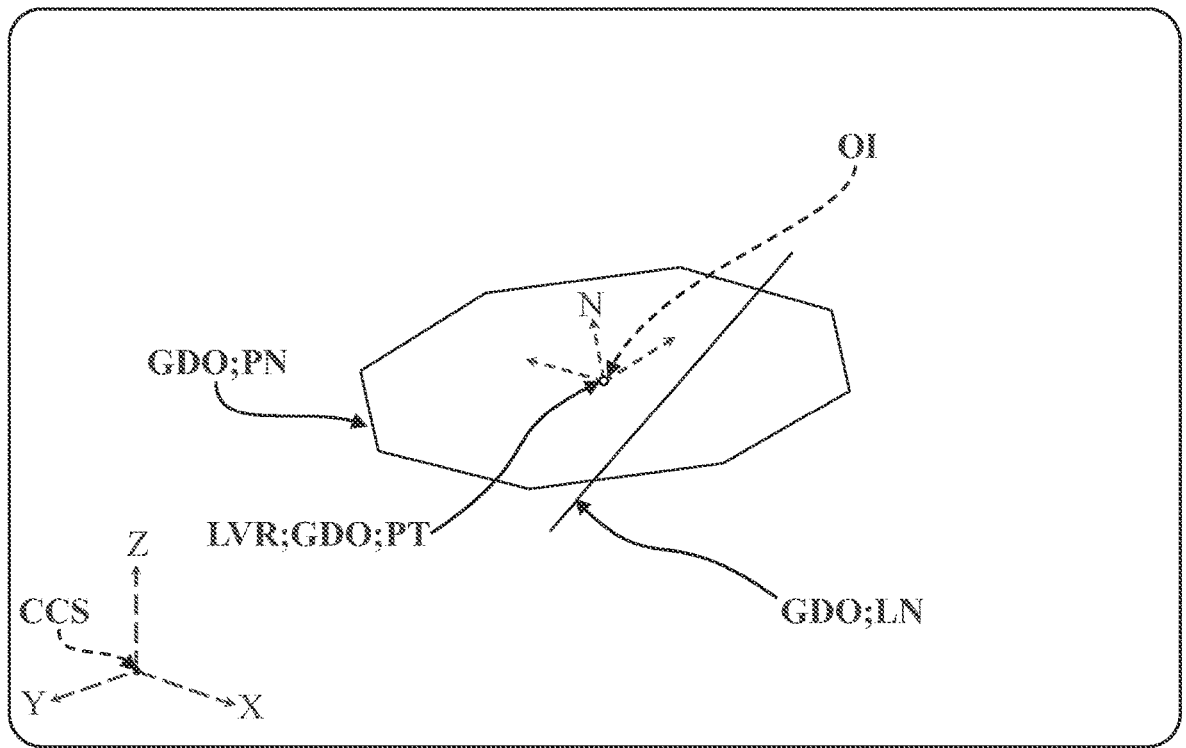
FIG. 16 is a visualization of a virtual reference frame rendered with the CAD program of FIG. 2, shown depicting an example geometrical design object realized as an octagonal plane arranged within the virtual reference frame, and another example geometrical design object realized as a line arranged as passing through the octagonal plane.

FIG. 16 depicts an example where a line LN is shown passing through (or "coincident with") an octagonal plane PN. In some embodiments, the arrangement depicted in FIG. 15 may be achieved using the tenth algorithm AL10 to project the line LN onto the plane PN.

Figure 17:
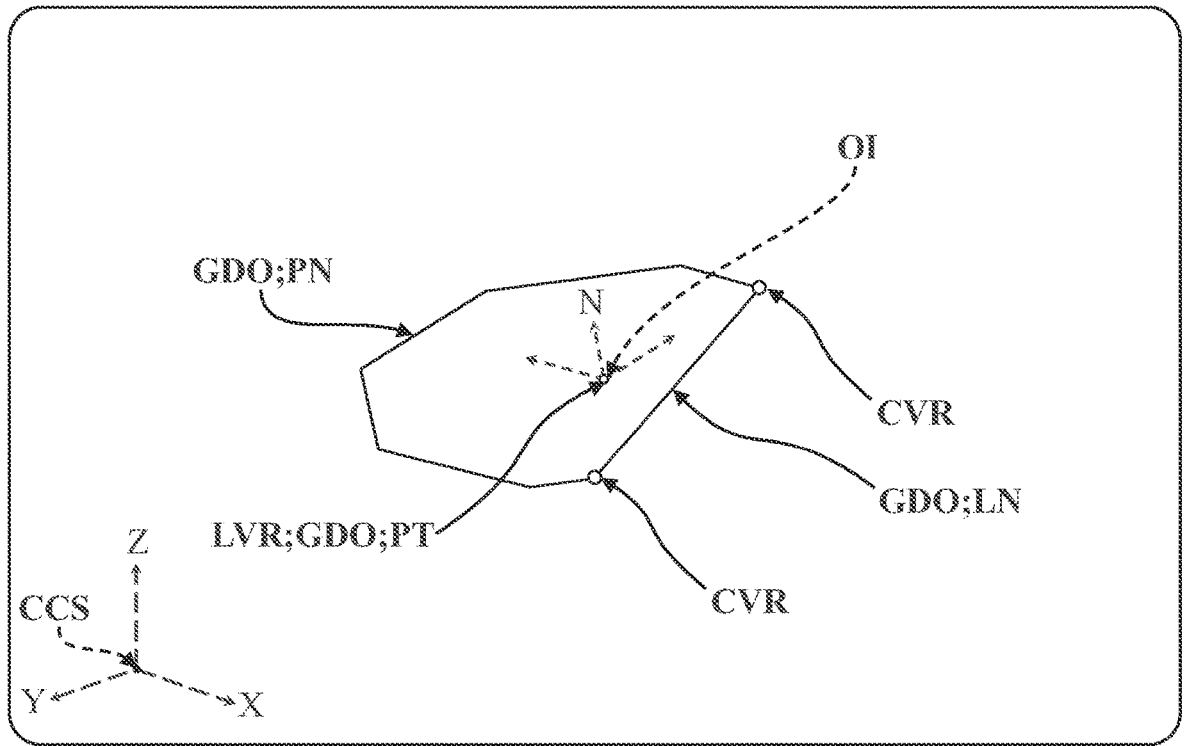
FIG. 17 is another visualization of the virtual reference frame depicted in FIG. 16, depicting a different geometrical design object constructed via cutting the octagonal plane along the line as depicted in FIG. 16.

FIG. 17 depicts a geometrical design objects GDO created by cutting an octagonal plane PN with a line LN as arranged in FIG. 16. Any one of the representative examples described above could be implemented in different ways to facilitate moving, constraining, orientating, positioning, or otherwise arranging existing geometrical design objects GDO using the relative to other object option 206, based such as on aspects of the algorithms module 174 (see FIG. 8) and/or aspects of the mathematical toolkit 168. Other configurations are contemplated.

Referring again to FIG. 7, in the existing object arrangement section 184, four general types of adjustments that can be utilized in connection with existing geometrical design objects GDO in order to facilitate planning the surgical step are represented: visibility adjustment 208, geometrical parameters adjustments 210, tracker assignment adjustments 212, and definition adjustments. As is described in greater detail below in connection with FIGS. 20A-26B, the visibility adjustments 208 can be used to change how geometrical design objects GDO are rendered in the visualization VIZ of the virtual reference frame VRF, such as by changing their color (e.g., to differentiate from other geometrical design objects GDO), applying and/or editing names (e.g., to correspond to portions of the anatomy), hiding or showing them (e.g., hiding one or more primitive type objects 196 used to assemble a compound type object 198), showing dimensions of or associated with the geometrical design object GDO (e.g., using angle measurements 200 and/or distance measurements 202), and the like. In some embodiments, certain features afforded by the visibility adjustments 208 can be accessed using the object/data manager 180, as described in greater detail below.

Figure 9A:
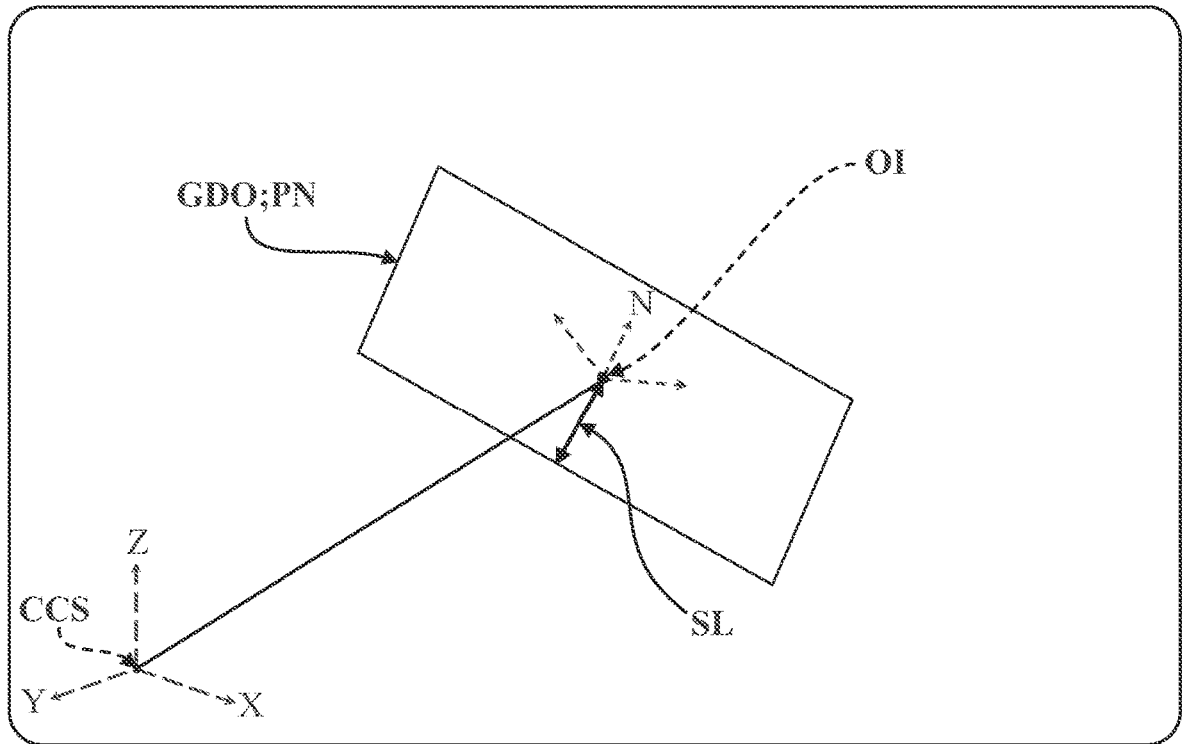
FIG. 9A is a visualization of a virtual reference frame rendered with the CAD program of FIG. 2, shown depicting an example geometrical design object having an object index illustrating a pose within the virtual reference frame, with the geometrical design object realized as a rectangular plane having a span.
Figure 9B:
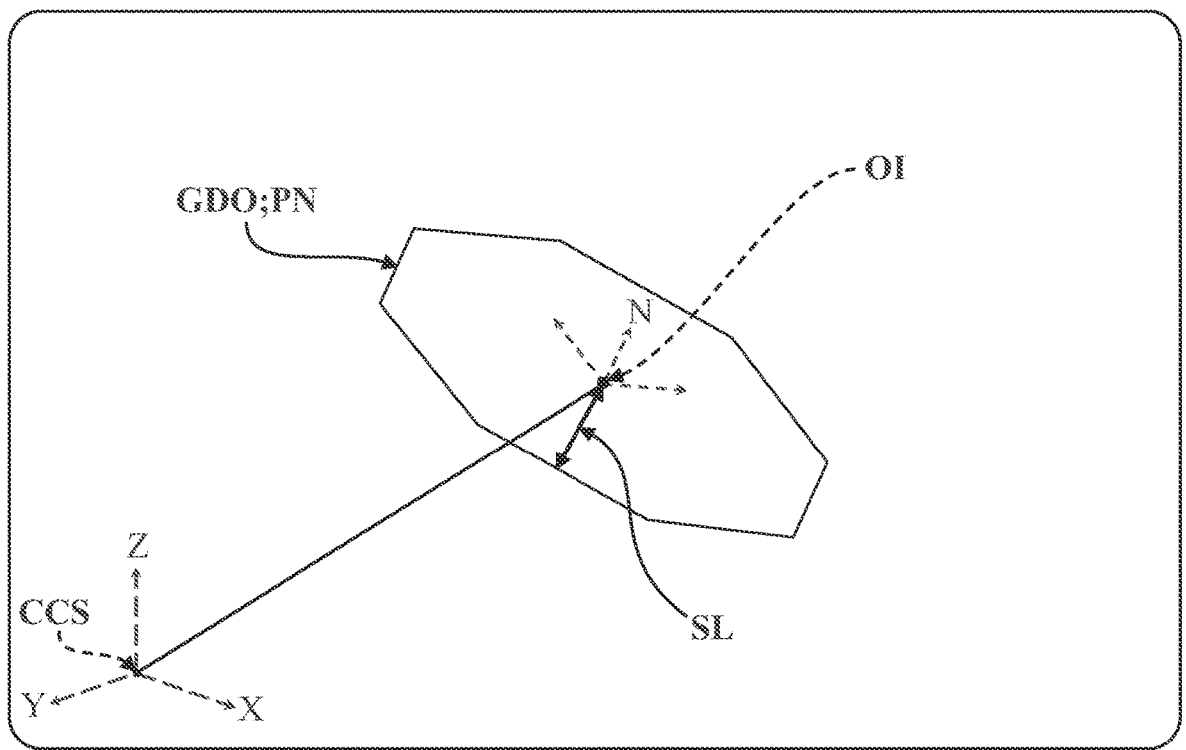
FIG. 9B is another visualization of the virtual reference frame of FIG. 9A, shown depicting the geometrical design object as having been adjusted to an octagonal plane while maintaining the same span and the same pose within the virtual reference frame.
Figure 11A:
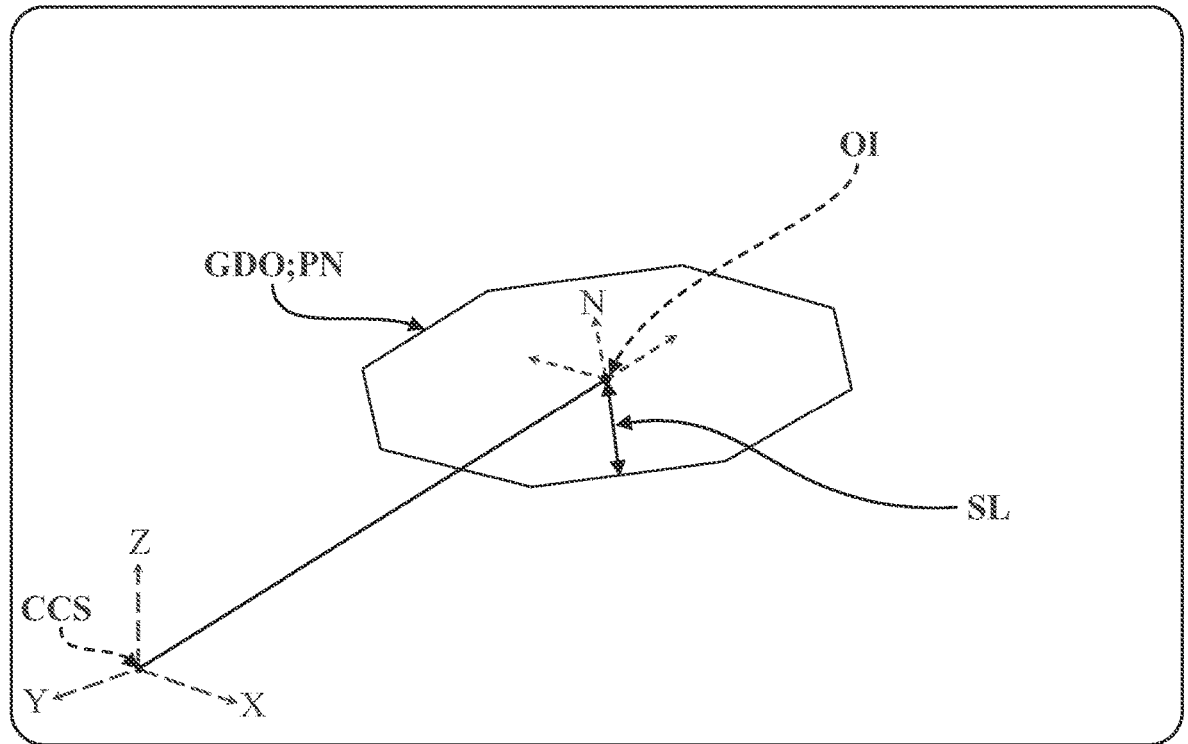
FIG. 11A is another visualization of the virtual reference frame and the geometrical design object of FIG. 10B, shown depicting the geometrical design object with the span shown in FIGS. 9A-10A.
Figure 11B:
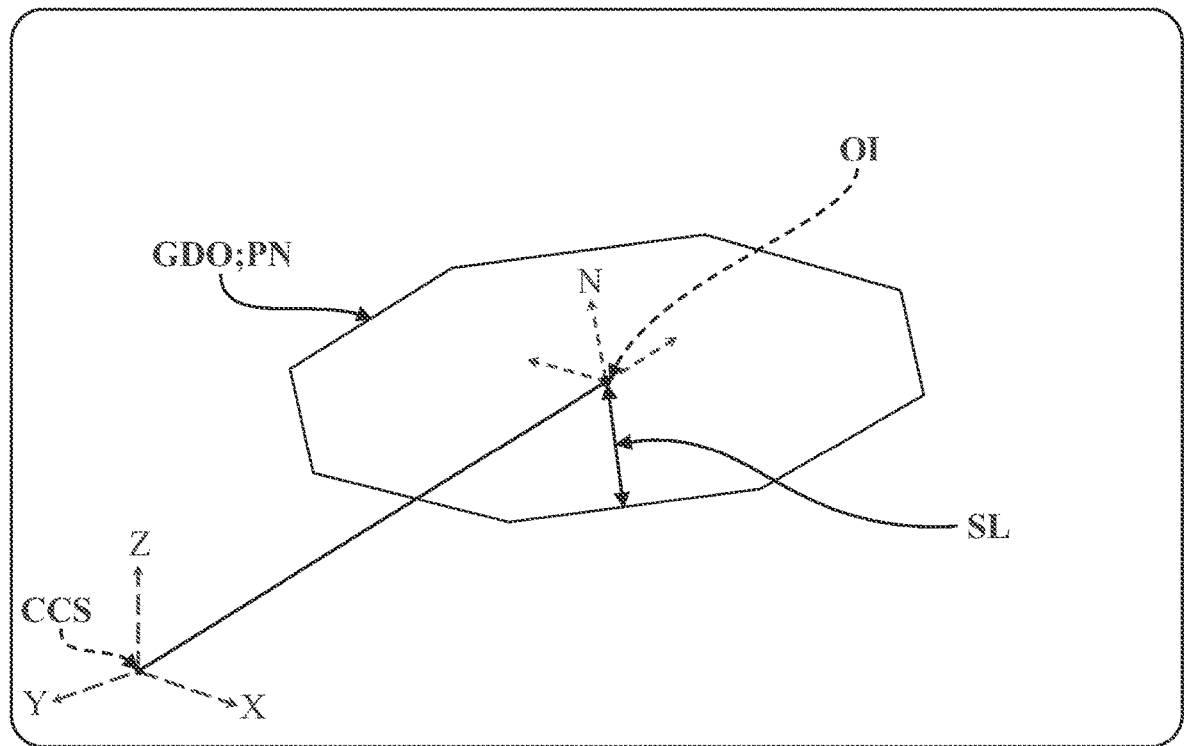
FIG. 11B is another visualization of the virtual reference frame and the geometrical design object of FIG. 11A, shown depicting the geometrical design object in the same pose as illustrated in FIG. 11A but having been adjusted to a larger span.

The geometrical parameters adjustments 210 can be used to facilitate altering various aspects of certain types of geometrical design objects GDO; in particular, altering planes PN which, as noted above, are utilized in the CAD program 102 of the present disclosure as two-dimensional polygons that have three or more sides symmetrically arranged at the span length SL about their object index OI, which is analogous to a coordinate system within the virtual reference frame VRF. The geometrical parameters adjustments 210 can be utilized in certain embodiments to, among other things, adjust the span length SL and the number of sides of planes PN. As is depicted in FIGS. 9A-9B, the number of sides of planes PN can be adjusted without altering the pose of the object index OI within the CAD coordinate system CCS, and without altering the span length SL (four sides shown in FIG. 9A and eight sides shown in FIG. 9B). Furthermore, as is depicted in FIGS. 11A-11B, the span length SL of planes PN can be adjusted without altering the pose of the object index OI within the CAD coordinate system CCS, and without altering the number of sides (smaller span length SL shown in FIG. 11A and larger span length SL shown in FIG. 11B). It will be appreciated that the ability to alter existing geometrical design objects GDO via the geometrical parameters adjustments 210 allows certain local virtual references LVR associated with those geometrical design objects GDO to be maintained even where the shape or orientation is subsequently altered.

The tracker assignment adjustments 212 may be used to fix (or "constrain") geometrical design objects GDO relative to one or more of the trackers 120, 132, 136, 138, 142, in one or more degrees of freedom. As is described in greater detail below, fixing geometrical deign objects GDO, local virtual references LVR, and/or calculated virtual references CVR may advantageously allow arrangement of geometrical design objects GDO within the virtual reference frame VRF in dynamic ways which may be depicted in near-real time with the visualization VIZ of the virtual reference frame VRF. Similarly, and as is described in greater detail below, the CAD program 102 may allow the surgeon to fix certain geometrical design objects GDO relative to the virtual digitizer reference point DRPV during arrangement of new or existing geometrical design objects GDO, such as may be used to orientate the visualization VIZ relative to the target site TS, and or to orientate the target site TS relative to the geometrical design objects GDO, local virtual references LVR, and/or calculated virtual references CVR rendered within the visualization VIZ. Other configuration are contemplated.

In some embodiments, the definition adjustments 214 may be used to define one or more geometrical design objects GDO arranged within the virtual reference frame VRF as virtual boundaries 216 (or "no-fly zones.") which should be avoided by the energy applicator 124 of the surgical tool 122 during the execution of the surgical procedure. To this end, virtual boundaries 216 may be defined with any suitable arrangement, assembly, or combination of geometrical design objects GDO where their local virtual references LVR have been fixed (or "constrained") to one of the patient trackers 136, 138. In some embodiments, virtual boundaries 216 may be defined using an arrangement of geometrical design objects GDO which define a volume or another solid model (e.g., a cylinder CY used to define a drill hole with a diameter and a depth along a trajectory). Put differently, one or more virtual boundaries 216 may be used to define or may otherwise be realized as "milling volumes MV" which represent specific portions of the target site TS to be removed with the surgical tool 122. In other some embodiments, virtual boundaries 216 may comprise an area of a surface and a normal vector associated with the surface (e.g., with a plane PN), or by areas and normal vectors associated with multiple surfaces (e.g., with a wedge WD, a triangle mesh TM, an osteotomy plane OP, a complex cut CX, a chevron cut CV, a scarf cut CS, and the like). To this end, the CAD program 102 may generate tool control data CZ based on geometrical design objects GDO which are defined as virtual boundaries 216 and/or based on a milling volume MV constructed therefrom (e.g., based on surface areas, normal vectors to indicate direction, and the like).

The tool control data CZ may be communicated to and interpreted by the tool controller 130 of the surgical tool 122 (see FIG. 4) for use during execution of the surgical procedure to control movement of and/or operation of the surgical tool 122 relative to the target site TS, such as by preventing the energy applicator 124 from contacting (or approaching too close to) a virtual boundary 216 defined with the CAD program 102, or by slowing or stopping movement of the energy applicator 124 as a virtual boundary 216 is contacted (or approached). Here, because the navigation system 104 is able to track states of each of trackers 120, 132, 136, 138, 142, and because the geometrical design objects GDO and local virtual references LVR used to define the virtual boundaries 216 (or the milling volume MV) and generate the tool control data CZ were established within the virtual reference frame VRF as being fixed to one of the patient trackers 136, 138, then execution of the surgical procedure with the surgical tool 122 can be navigated and/or guided using the navigation system 104 based on tracked states SZ of the tool tracker 132 and one or more of the patient trackers 136, 138.

Referring now to FIGS. 1, 4, and 7, in some embodiments, the definition adjustments 214 (see FIG. 7) of the CAD program 102 may be used to define one or more geometrical design objects GDO arranged within the virtual reference frame VRF as a virtual implant model 218. Put differently, in some embodiments, the CAD program 102 is configured to enable constructing virtual implant models 218 from one or more geometrical design objects GDO arranged within the virtual reference frame VRF. Here, in some embodiments, the surgical system 100 may further comprise an implant manufacturing device 220 coupled to the computing device 108 which is configured to intraoperatively generate an implant 222 (see FIG. 1) based on the virtual implant model 218, such as using one or more additive manufacturing techniques. The implant 222 may be manufactured using one or more materials which are generally inert, are biologically-compatible, which facilitate bone redemonstration, and the like. Other configurations are contemplated.

Referring now to FIGS. 19A-19F, as noted above, CAD program 102 is configured such that the surgeon can modify and/or establish relationships of local virtual references LVR and/or geometrical design objects GDO with different patient trackers 136, 138 using, for example, the tracker assignment adjustments 212 (see FIG. 7). In FIG. 19A, for example, the visualization VIZ of the virtual reference frame VRF depicts a registered local virtual reference LVR previously established at the saddle point landmark LM_SP of the femur F which is spaced from the virtual digitization device 106V. Here, the registered local virtual reference LVR of the saddle point landmark LM_SP is fixed (or "constrained") to the virtual first patient tracker 136V, illustrated by a dash-dash line extending to the virtual patient coordinate system PCSV.

Figure 19B:
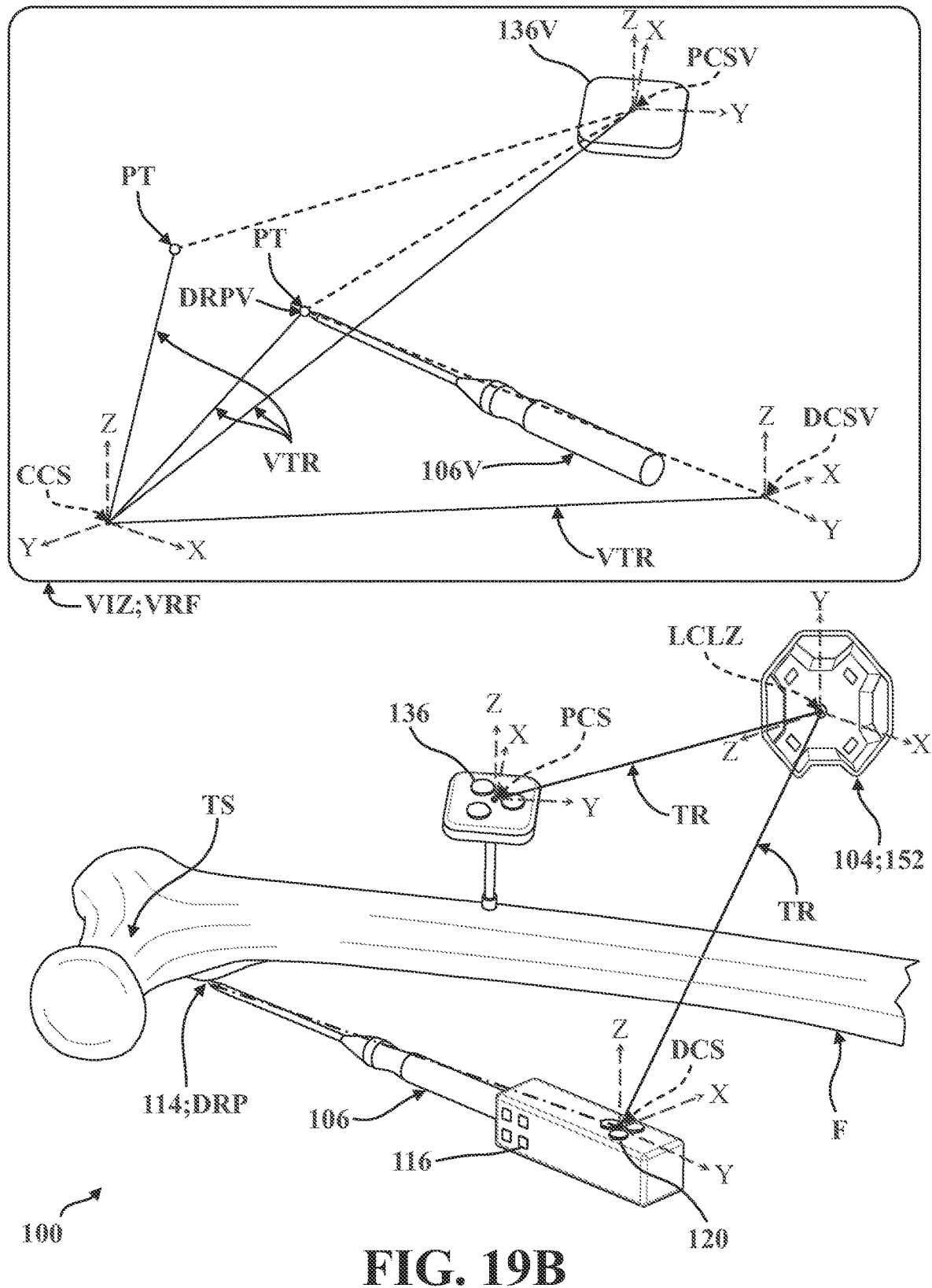
FIG. 19B is another partial perspective view of the components of the surgical system and the visualization of the virtual reference frame of FIG. 19A, shown with the digitization device positioned at the trochanter minor landmark of the femur, and illustrating registration of another local virtual reference within the virtual reference frame established as a point representing the trochanter minor landmark of the femur.
Figure 19C:
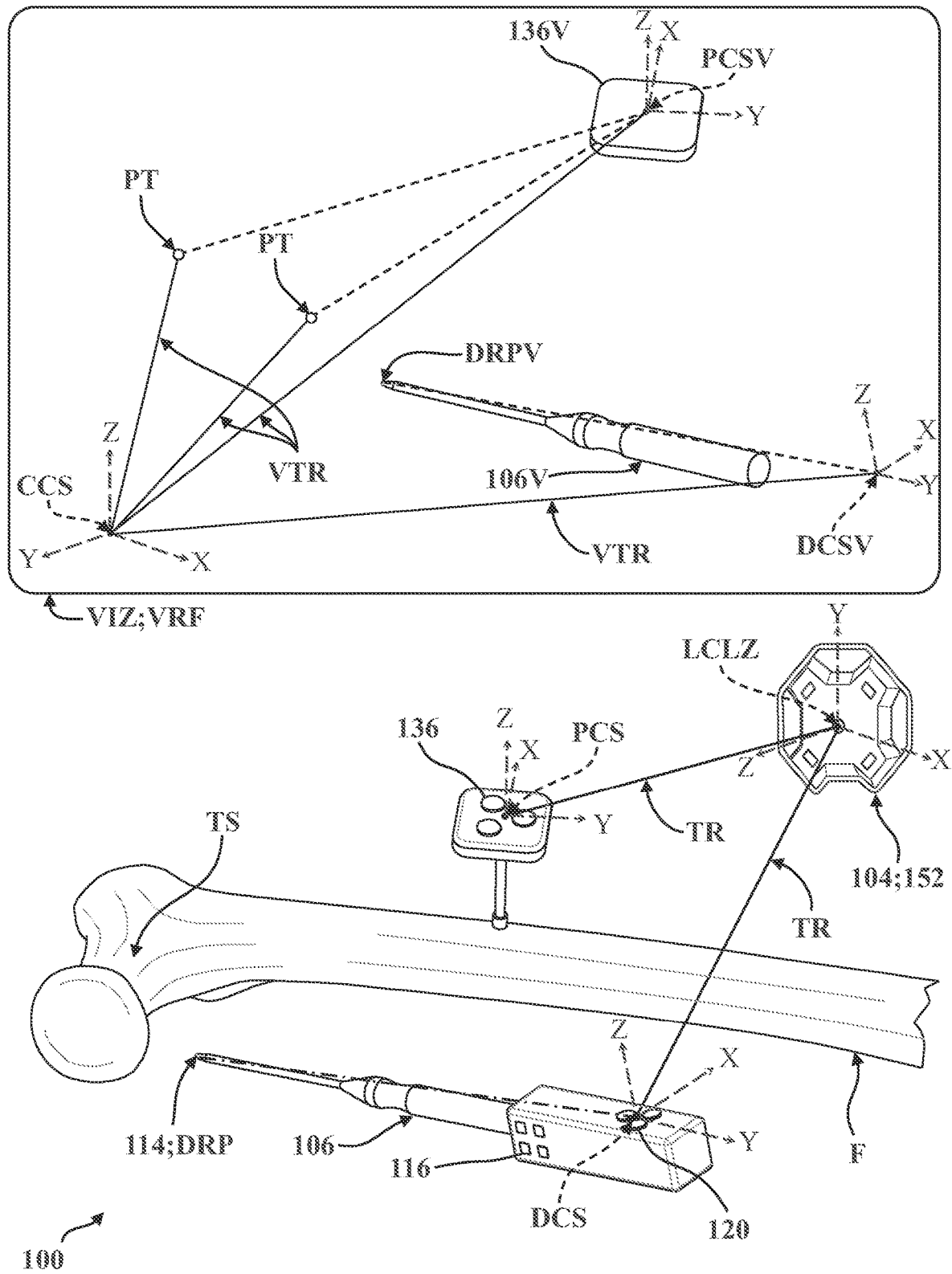
FIG. 19C is another partial perspective view of the components of the surgical system and the visualization of the virtual reference frame of FIG. 19B, shown illustrating movement of the digitization device relative to the femur and also illustrating corresponding movement of the virtual representation of the digitization device relative to the registered local virtual references arranged within the virtual reference frame, the registered local virtual references having been established as points representing the trochanter minor landmark and the saddle point landmark of the femur.

In FIG. 19B, which depicts another registered local virtual reference LVR subsequently established at the trochanter minor landmark LM_TM of the femur F, the registered local virtual reference LVR of the saddle point landmark LM_SP remains fixed to the virtual first patient tracker 136V. Here too in FIG. 19B, the registered local virtual reference LVR of the trochanter minor landmark LM_TM is fixed to the virtual first patient tracker 136V, likewise illustrated by a dash-dash line extending to the virtual patient coordinate system PCSV. Moreover, in FIG. 19B (and also in FIGS. 19A and 19C), a dash-dash line extends between the virtual tool reference point TRPV and the virtual digitizer coordinate system DCSV to demonstrate that the virtual tool reference point TRPV moves concurrently within the virtual reference frame VRF with the virtual digitization device 106V in response to corresponding movement of the digitization device 106. Movement of this type may be observed by sequentially comparing FIG. 19B, which shows the digitizer reference point DRP at the trochanter minor of the femur F, to FIG. 19C, which shows the digitizer reference point DRP moved away from the femur F.

Figure 19D:
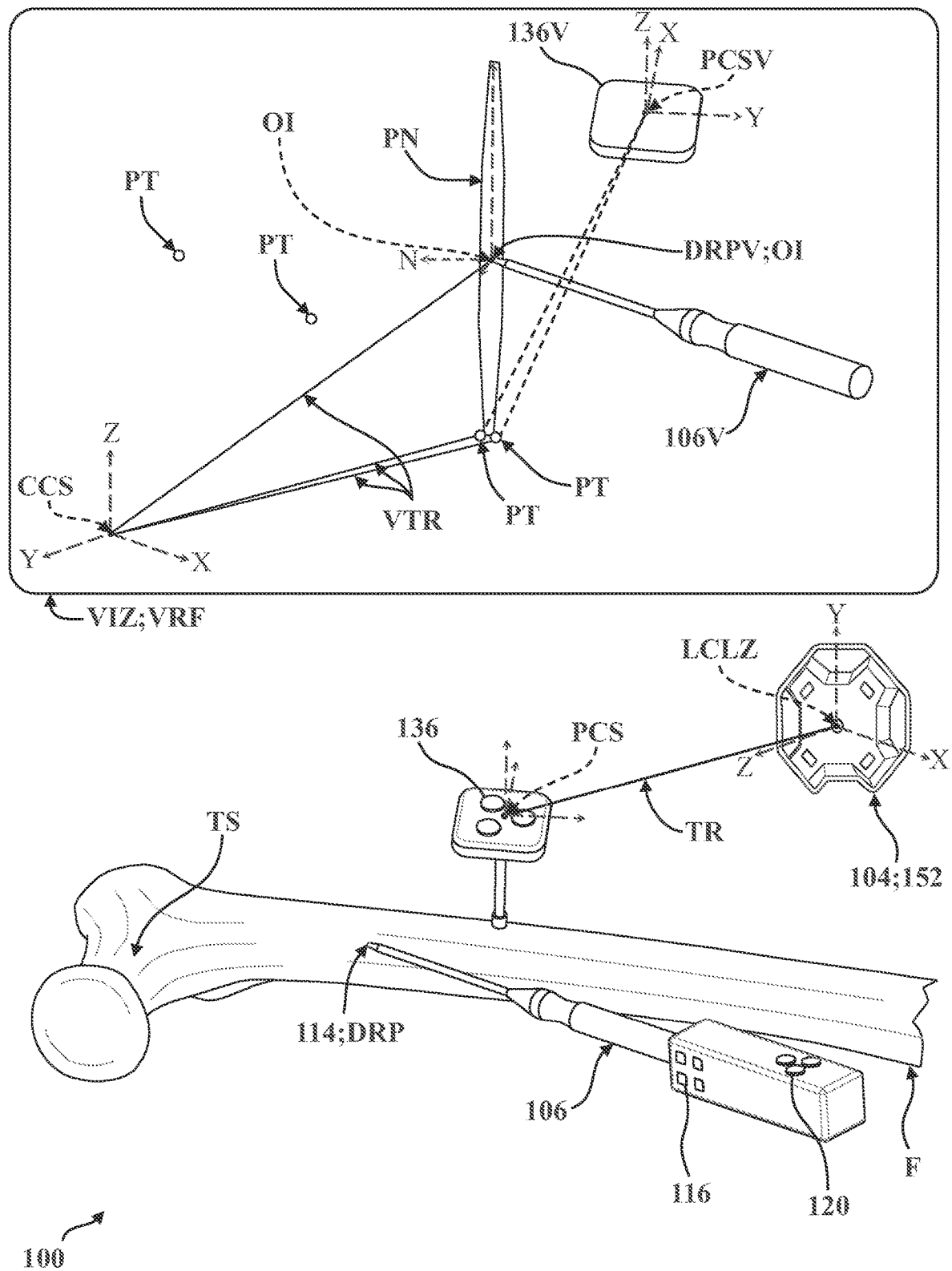
FIG. 19D is another partial perspective view of the components of the surgical system and the visualization of the virtual reference frame of FIG. 19C, shown illustrating transforms of one example geometrical design object realized as a line segment defined by two additional registered local virtual references established within the virtual reference frame, and shown illustrating transforms of another example geometrical design object realized as an octagonal plane arranged with one edge fixed relative to the registered local virtual references of the line segment, the octagonal plane further shown having an object index fixed at another registered local virtual reference established within the virtual reference frame.

In FIG. 19D, the visualization VIZ of the virtual reference frame VRF shows an octagonal plane PN which shares an edge with a line segment LS defined with two established local virtual references LVR which are fixed to the virtual first patient tracker 136V. Here, the object index OI of the octagonal plane PN has just been defined with another local virtual reference LVR established based on the illustrated position of the virtual digitizer reference point DRPV.

Figure 19E:
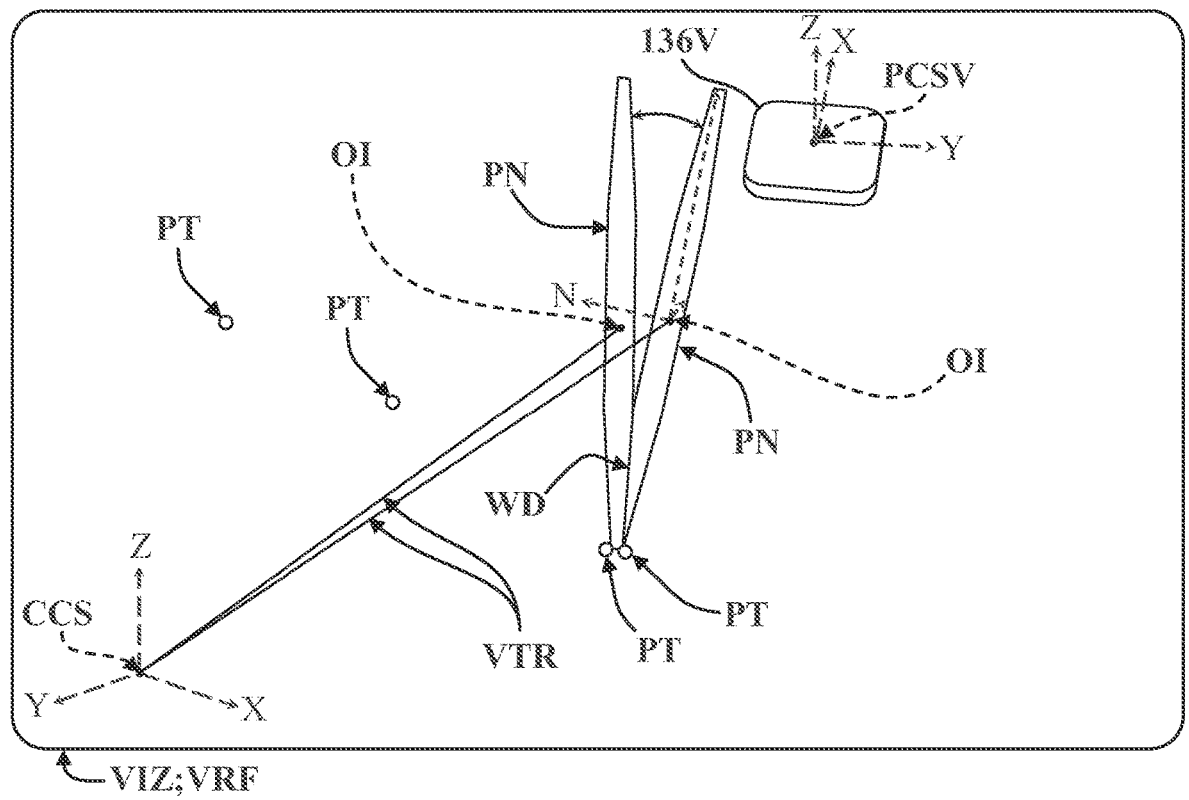
FIG. 19E is another partial perspective view of the components of the surgical system and the visualization of the virtual reference frame of FIG. 19D, shown illustrating transforms of an example compound geometrical design object realized as a wedge constructed with another octagonal plane arranged at a common edge fixed relative to the registered local virtual references of the line segment and having an object index fixed at a calculated virtual reference established by adjusting an angle measured between the octagonal planes.
Figure 19E:
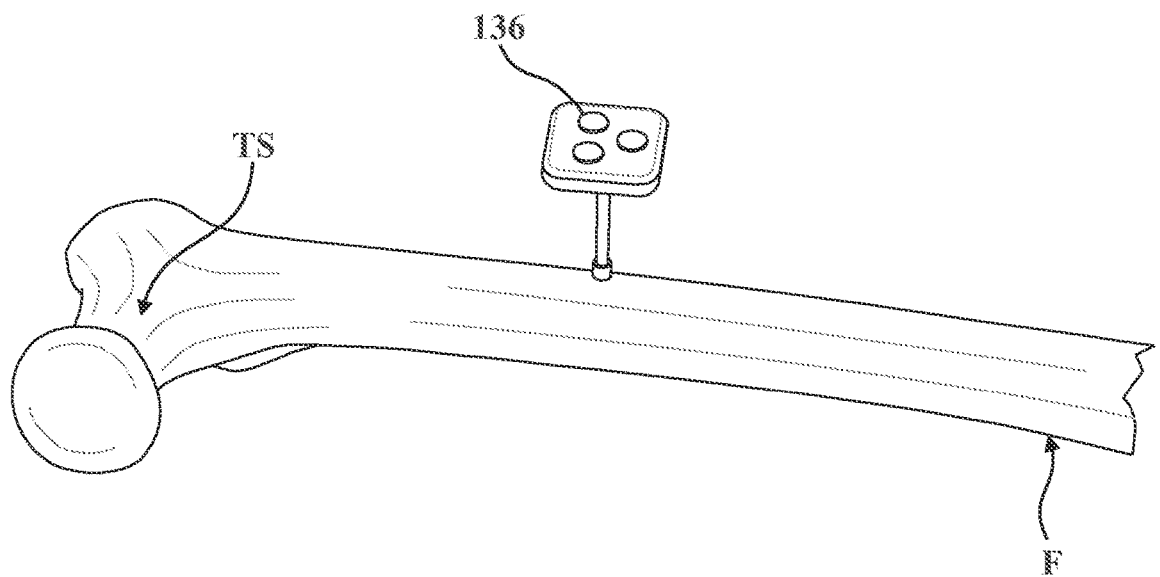

In FIG. 19E, the visualization VIZ of the virtual reference frame VRF shows two octagonal planes PN which share a common edge (along the same line segment LS described above and illustrated in FIG. 19D), and which is spaced from the first octagonal plane PN at an angle measurement 200 to define a wedge WD. In this illustrative example, the wedge WD is fixed to the virtual first patient tracker 136V based on one or more of its local virtual references LVR having been established with the digitization device D relative to the femur F to which the first patient tracker 136 is attached, as noted above.

Figure 19F:
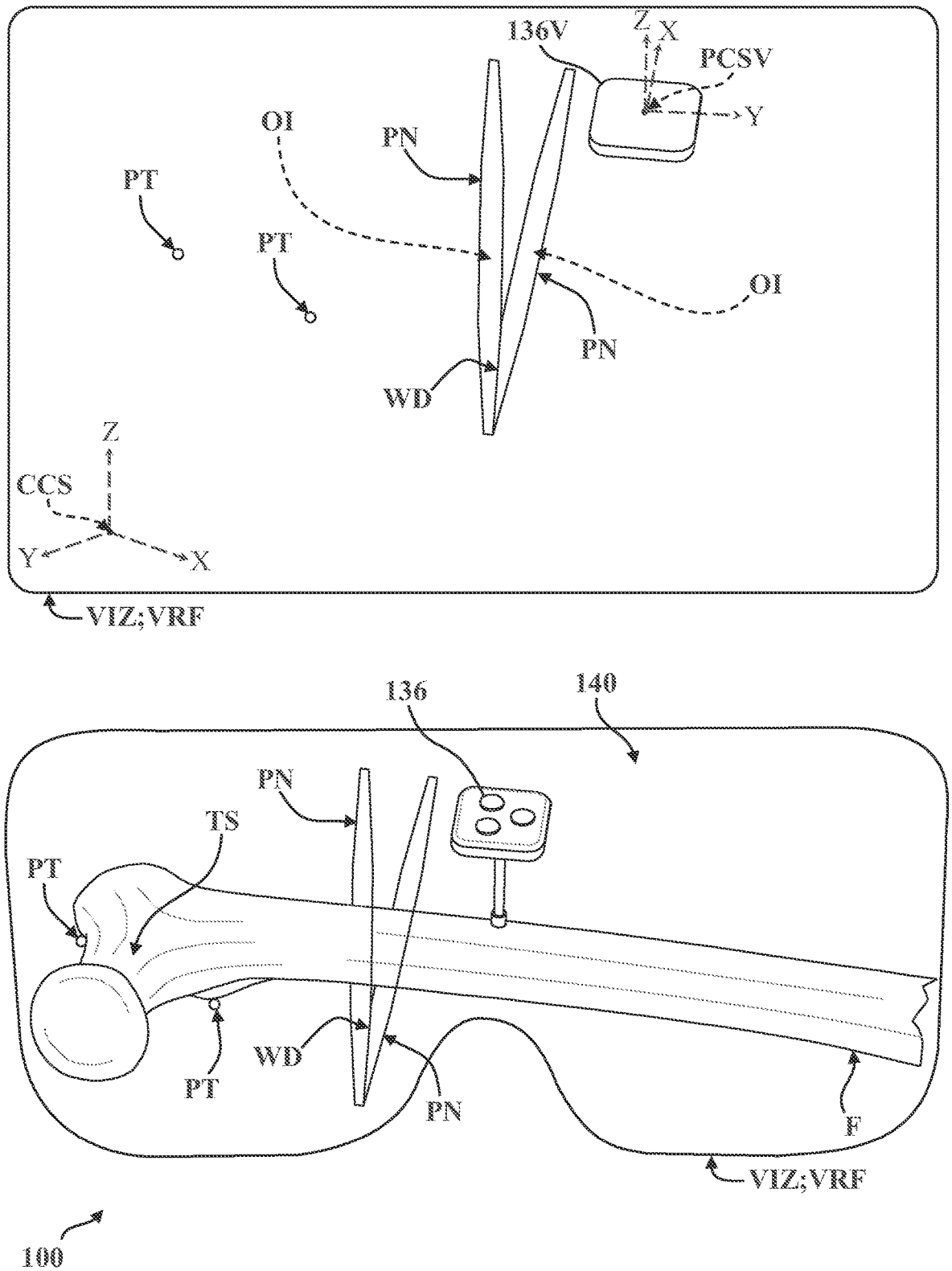
FIG. 19F is a partial perspective view of the components of the surgical system and the visualization of the virtual reference frame of FIG. 19E, shown with the femur and the tracker depicted as being viewed through the HMD unit of FIG. 18 to illustrate the wedge and the points established at the saddle point landmark and the trochanter minor landmark rendered overlaid onto the femur with augmented reality.

In FIG. 19F, the same wedge WD illustrated in FIG. 19E is shown, along with the registered local virtual references LVR of the saddle point landmark LM_SP and the trochanter minor landmark LM_TM, are shown in the visualization VIZ of the virtual reference frame VRF depicted with the display unit 148. However, in FIG. 19F, the femur F of the patient's anatomy at the target site TS, and the first patient tracker 136 attached to the femur F, are depicted as viewed through the HMD unit 140 (see FIGS. 1 and 18) such that the wedge WD and the registered local virtual references LVR of the saddle point landmark LM_SP and the trochanter minor landmark LM_TM, are rendered overlaid onto the femur F with augmented reality (or "mixed reality") according to embodiments of the present disclosure. Here, because the navigation system 104 is able to track states of each of trackers 120, 132, 136, 138, 142 and because the geometrical design objects GDO and local virtual references LVR were established within the virtual reference frame VRF as being fixed to the first patient tracker 136, then the contents of the virtual reference frame VRF can be presented to the surgeon in mixed reality and can dynamically change to compensate for movement of the display unit tracker 142 relative to the localizer 152 as the surgeon observes the target site TS. In some embodiments, the HMD unit 140 may be provided with sensors (e.g., inertial sensors, eye-tracking sensors, and the like) which help facilitate rendering the visualization VIZ overlaid onto the patient's anatomy at the target site TS. Other configurations are contemplated.

Figure 20A:
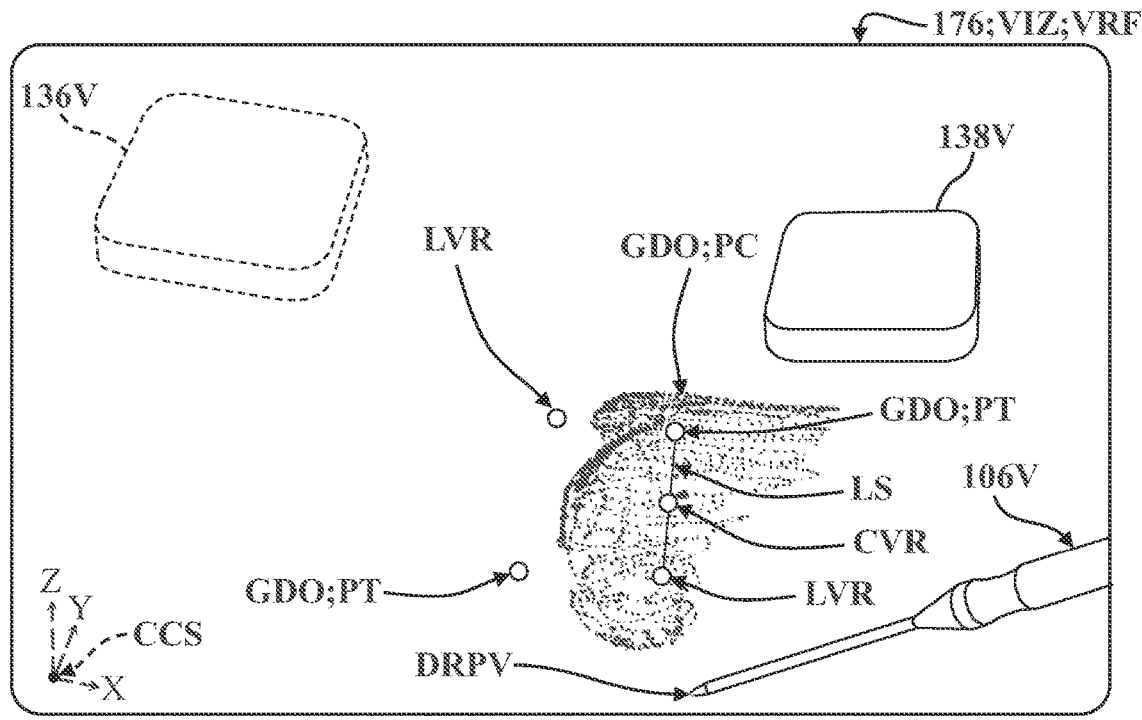
FIG. 20A is a representation of one embodiment of the GUI of FIG. 5, shown depicting a visualization of a virtual reference frame adjacent to functions of the CAD program including options to create new objects, adjust objects, measure, manage objects, and manage views of the visualization, shown with an object manager function selected and listing objects arranged within the virtual reference frame with some of the objects hidden in the visualization.
Figure 20A:
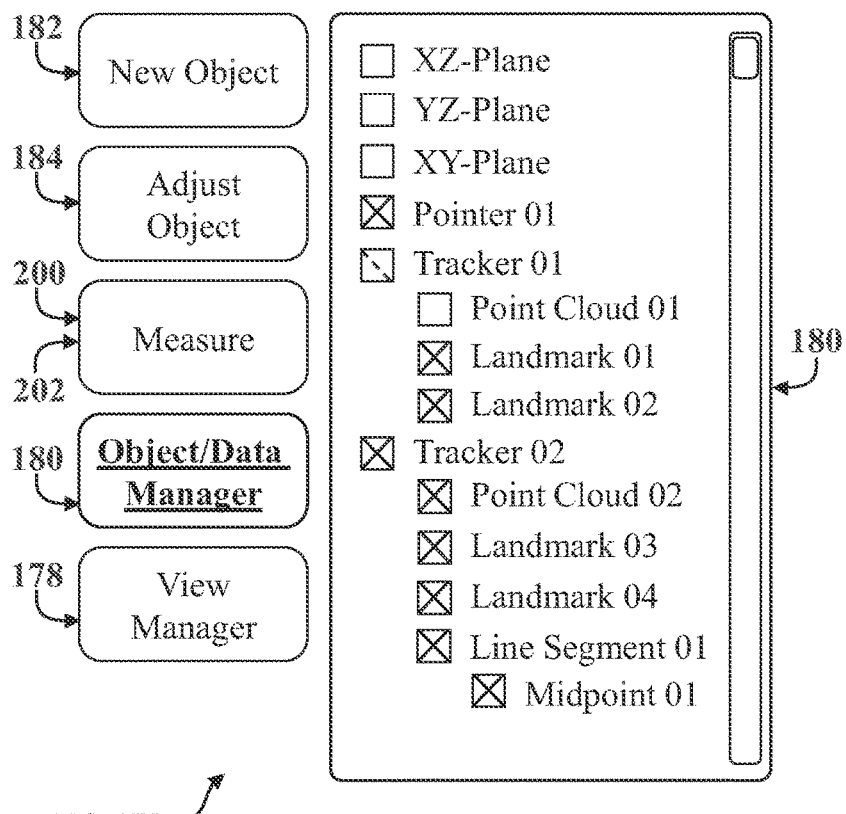
Figure 20B:
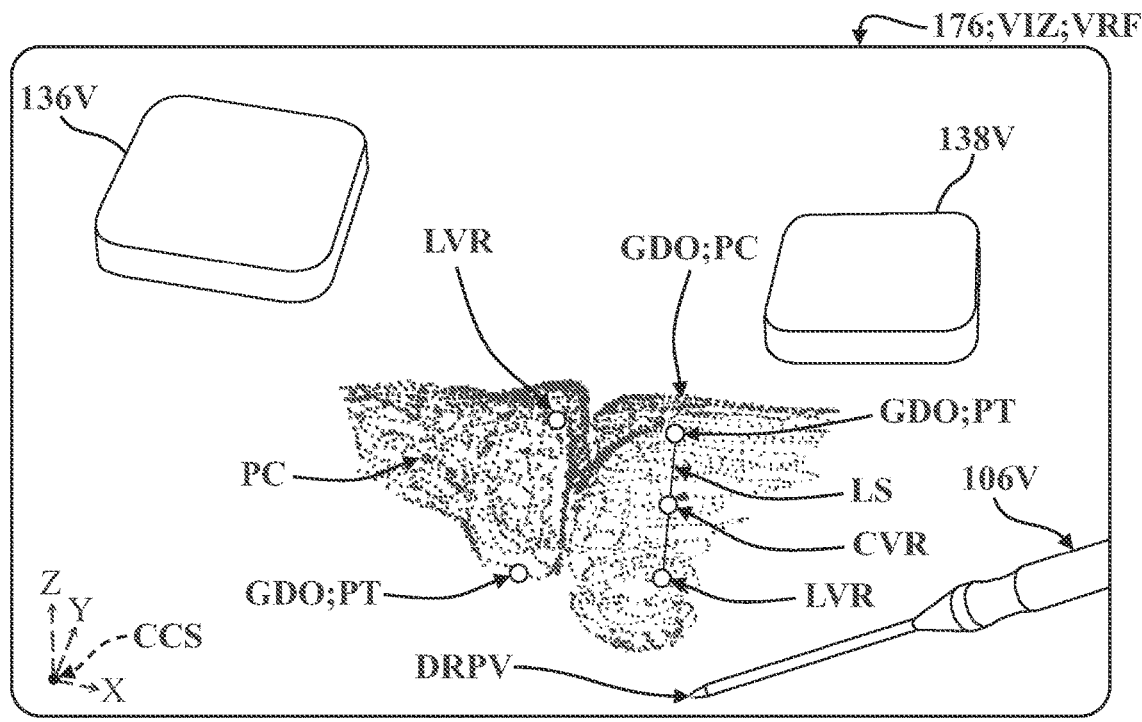
FIG. 20B is another representation of the GUI of FIG. 20A, shown with the object manager function still selected and listing the objects arranged within the virtual reference frame with some of the objects unhidden in the visualization.
Figure 20B:
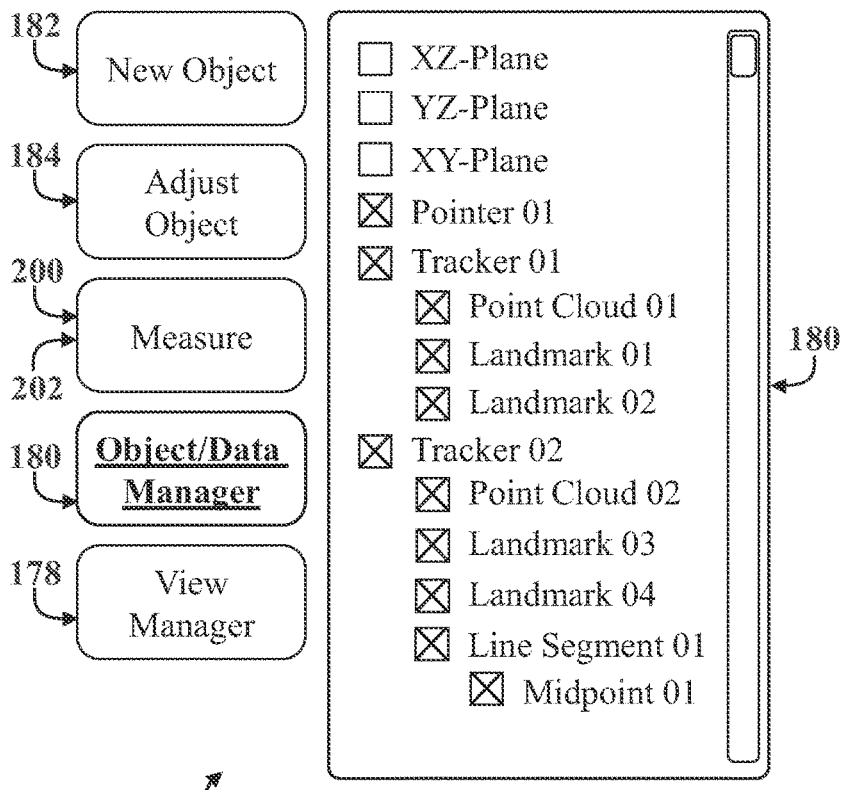

Referring now to FIGS. 20A-20B, a representative embodiment of the GUI 172 of the CAD program 102 is shown. In this embodiment (and also in the embodiments illustrated in FIGS. 21A-26B) the GUI 172 employs the visualization window 176 to render the visualization VIZ of the virtual reference frame VRF to the surgeon. Here too, the CAD program 102 may be configured to render, within the visualization VIZ, the various geometrical design objects GDO arranged within the virtual reference frame VRF, registered local virtual references LVR, calculated virtual references CVR, and virtual representations of various components of the surgical system 100 (e.g., the virtual first patient tracker 136V, the virtual second patient tracker 138V, the virtual digitization device 106V, the virtual surgical tool 122V, one or more coordinate systems, and the like).

FIGS. 20A-20B also depict operation of one embodiment of the object/data manager 180 of the GUI 172 of the CAD program 102. Here, the object/data manager 180 may be used by the surgeon to, among other things, hide or un-hide various geometrical design objects GDO (compare FIG. 20A with FIG. 20B), view relationships associated with tracker assignment adjustments 212 (e.g., which geometrical design objects GDO are fixed to which patient trackers 136, 136), and view relationships associated with compound type objects 198 (e.g., which primitive type objects 196 were used for construction). In addition, in some embodiments, the contents of the object/data manager 180 may be used to facilitate generating contextual options during a mixed approach 190, as is described in greater detail below in connection with FIGS. 23B-23C.

Figure 21A:
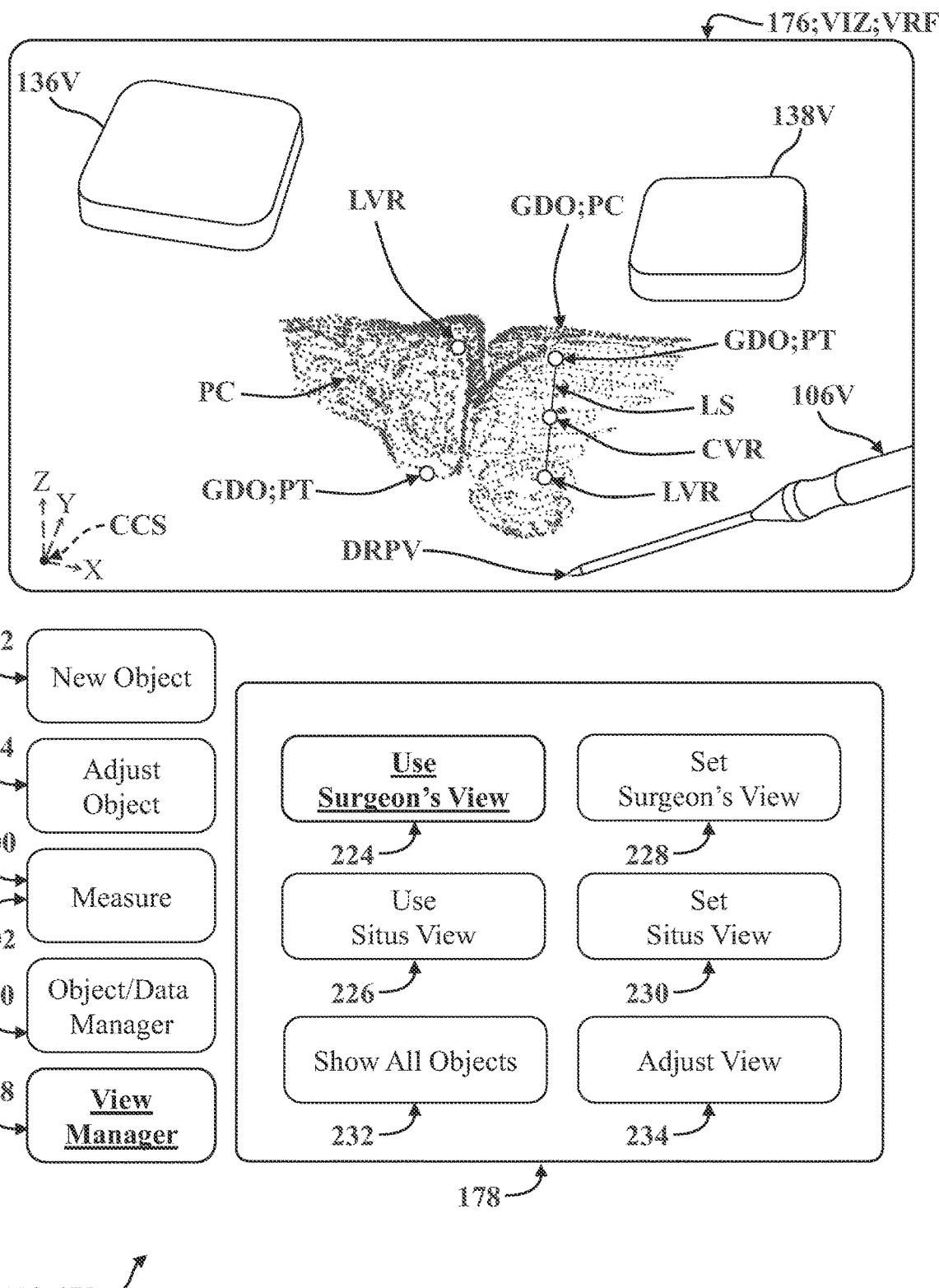
FIG. 21A is another representation of the GUI of FIG. 20A, shown with the view manager function selected and indicating that the visualization is orientated to a surgeon's view.
Figure 21B:
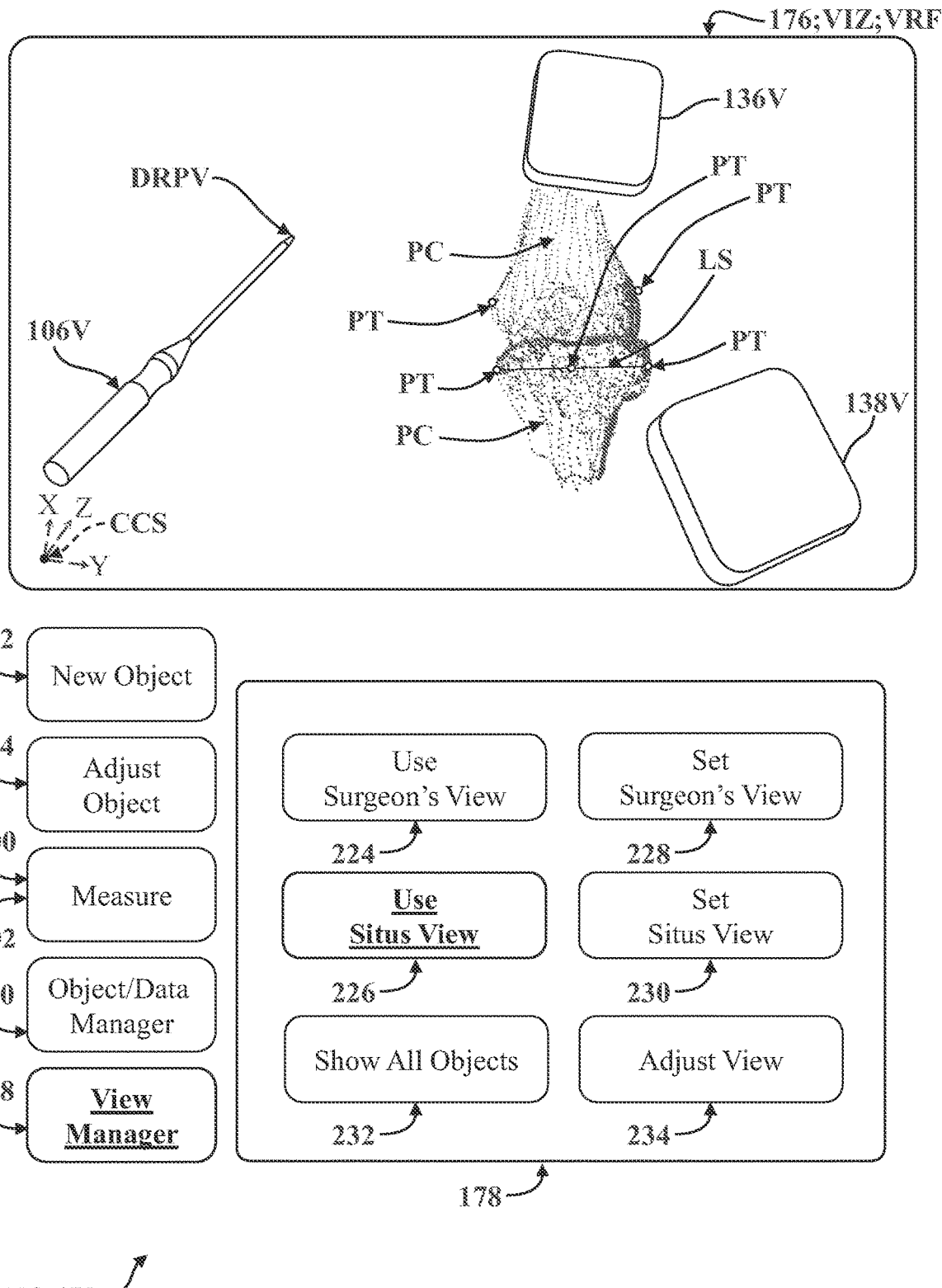
FIG. 21B is another representation of the GUI of FIG. 21A, shown with the view manager function still selected and indicating that the visualization is orientated to a situs view.

FIGS. 21A-21B depict operation of one embodiment of the view manager 178 of the GUI 172 of the CAD program 102. The view manager 178 allows the surgeon to orientate the visualization VIZ depicted by the visualization window 176 in different ways. In the illustrated embodiment, the view manager 178 comprises a use surgeon's view option 224, a use situs view option 226, a set surgeon's view option 228, a set situs view option 230, a show all objects option 232, and an adjust view option 234.

The use surgeon's view option 224 has been selected in FIG. 21A, and the use situs view option 226 has been selected in FIG. 21B. The adjust view option 234 can be selected to change the orientation of the visualization VIZ depicted by the visualization window 176 in different ways, such as by rotating, panning, zooming, and the like (e.g., with gestures, with one or more control inputs 150, and the like). In some embodiments, the CAD program 102 is configured to enable the surgeon to use the adjust view option 234 to orientate the visualization VIZ based on the position and/or orientation of the digitization device 106 (e.g., by simulating a "camera" placed at the pointer tip 114).

If a desired orientation of the visualization VIZ has been established using the adjust view option 234, the surgeon can subsequently use the set surgeon's view option 228 and/or the set situs view option 230 to use the desired orientation later during the procedure, and switch between the use surgeon's view option 224 and the use situs view option 226 in a quick, efficient manner. In some embodiments, the CAD program 102 may be configured to automatically determine one or more orientations initially (e.g., based on tracked states SZ of one or more of the trackers 120, 132, 136, 138, 142), and the surgeon can subsequently modify the automatically determined orientation using the adjust view option 234. Other configurations are contemplated. The show all objects option 232 may be implemented in some embodiments of the CAD program 102 to quickly and efficiently un-hide all of the geometrical design objects GDO, registered local virtual references LVR, calculated virtual references LVR, and/or virtual representations of the various components of the surgical system 100 rendered within the visualization VIZ.

Figure 22A:
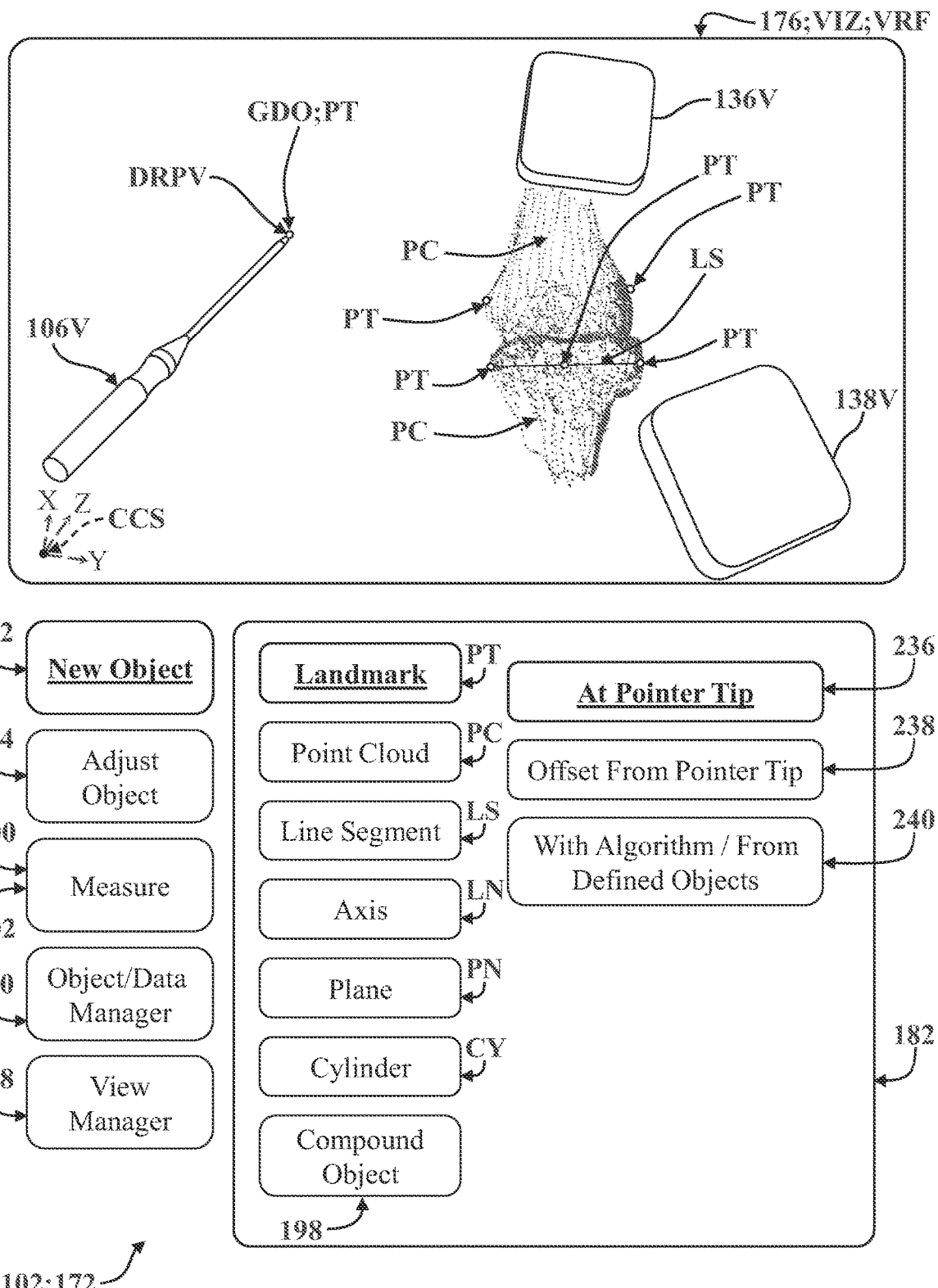
FIG. 22A is another representation of the GUI of FIG. 20A, shown with the new object function selected to create a point at a pointer tip of a virtual representation of the digitization device rendered within the visualization.
Figure 22B:
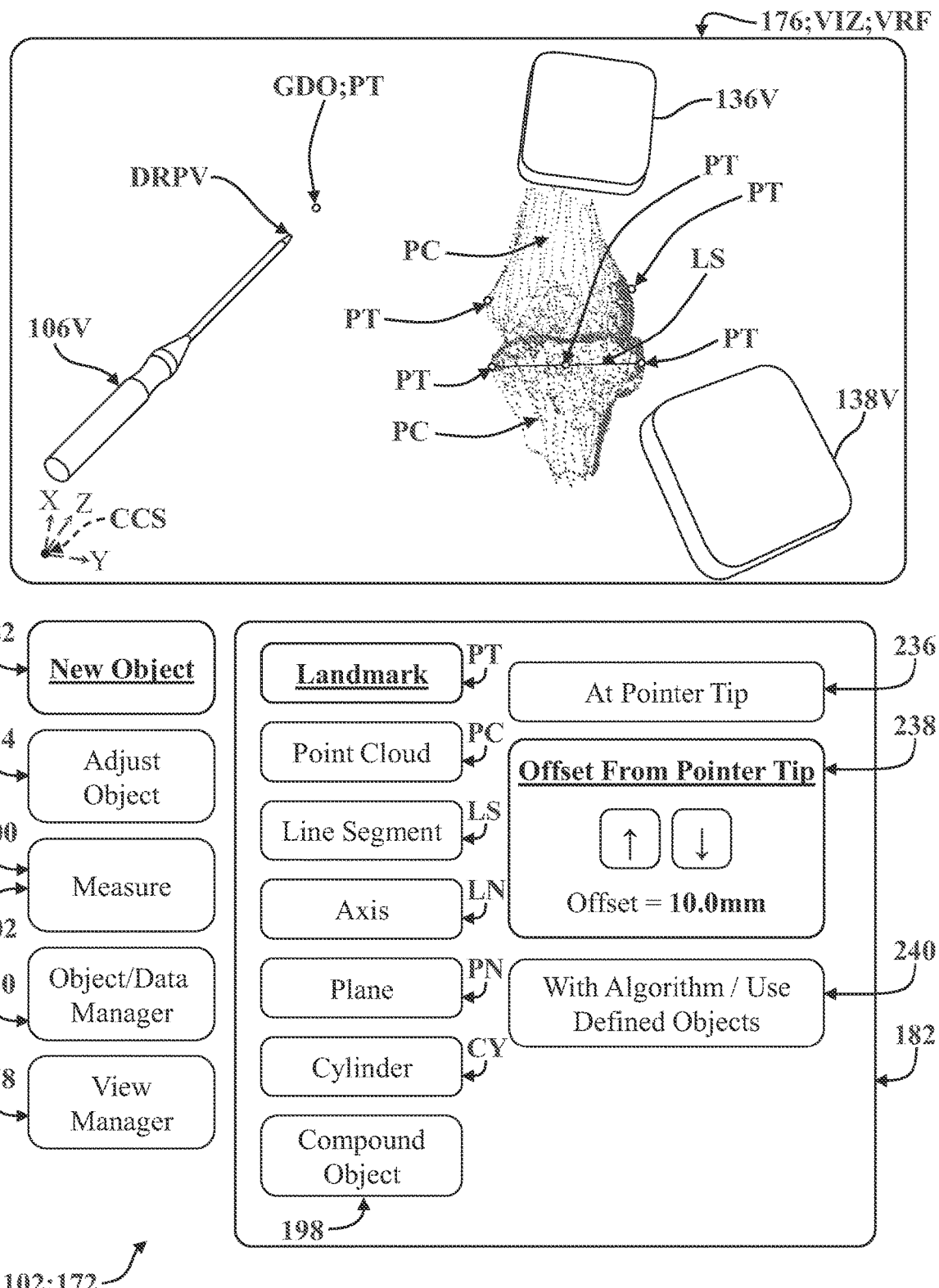
FIG. 22B is another representation of the GUI of FIG. 22A, shown with the new object function selected to create the point offset from the pointer tip of the virtual representation of the digitization device rendered within the visualization.

Referring now to FIGS. 22A-22B, additional aspects of the CAD program 102 are shown in connection with using the new object arrangement section 182 described above. As will be appreciated from the subsequent description below in connection with FIGS. 24A-24C, in some embodiments the CAD program 102 is configured to facilitate fixing (or "constraining") one or more of the different types of geometrical design objects GDO to the position and/or orientation of the virtual digitization device 106V rendered in the visualization VIZ of the virtual reference frame VRF. Put differently, the surgeon can construct new geometrical design objects GDO (or move geometrical design objects GDO arranged within the virtual reference frame VRF) by "snapping" them in predetermined orientations and/or positions relative to the virtual digitizer reference point DRPV.

In some embodiments, this functionality can help the surgeon arrange primitive type objects 196 and/or compound type objects 198 using the top-down approach 188, such as by fixing a selected geometrical design object GDO in up to six degrees of freedom relative to the virtual digitizer reference point DRPV before any local virtual references LVR for the selected geometrical design object GDO have been established or registered within the virtual reference frame VRF. The CAD program 102 could then guide the surgeon through defining the selected geometrical design object GDO by sequentially establishing the requisite local virtual references LVR which are needed to fully define the selected geometrical design object GDO. This concept is illustrated in and described in greater detail below in connection with FIGS. 35-37.

In some embodiments, actuating the tool control input 128 could unfix the selected geometrical design object GDO in one or more degrees of freedom based on subsequent (and sometimes successive) actuation of the tool control input 128. For example, actuating the tool control input 128 a first time could establish a local virtual reference LVR associated with the objet index OI of a plane PN, actuating the tool control input 128 a second time could orientate the object index OI relative to the CAD coordinate system CCS (e.g., by rotating the plane PN about the object index OI), and a actuating the tool control input 128 a third time could adjust the span length SL of the plane PN. It will be appreciated that the forgoing example is illustrative and non-limiting, and other configurations are contemplated by the present disclosure.

Furthermore, in embodiments which utilize the HMD unit 140, a virtual representation of the selected geometrical design object GDO may be rendered overlaid onto the patient's anatomy relative to the target site TS, which affords the surgeon with the ability to position the selected geometrical design object GDO with augmented reality (or mixed reality) by moving the digitization device 106 arbitrarily relative to the target site TS in ways which may or may not be associated with portions of the patient's anatomy (e.g., with the pointer tip 114 positioned in air and not contacting the anatomy). This functionality can also be utilized without the HMD unit 140 while still affording the surgeon with the ability to move the rendered geometrical design object GDO within the visualization VIZ relative to existing geometrical design objects GDO arranged within the virtual reference frame VRF (e.g., relative to point clouds PC; sec FIGS. 24A-24C). Other configurations are contemplated.

With continued reference to FIGS. 22A-22B, the CAD program 102 may be configured to fix geometrical design objects GDO relative to the virtual digitization device 106V (and, when used with the HMD unit 140, relative to the digitization device 106) in different ways. More specifically, and as is described in greater detail below, the surgeon is able to select between using an at pointer tip option 236, an offset from pointer tip option 238, and a with algorithm/from defined objects option 240, each of which are described in greater detail below.

In FIG. 22A, the surgeon has selected the at pointer tip option 236 in order to arrange a new geometrical design object GDO realized as a point PT (landmark). Here, the visualization VIZ shows the point PT arranged at the virtual digitizer reference point DRPV.

In FIG. 22B, the surgeon has selected the offset from pointer tip option 238 to arrange a new geometrical design object GDO realized as a point PT (landmark). Here, the visualization VIZ shows the point PT arranged offset from the virtual digitizer reference point DRPV at a distance that can be adjusted by the surgeon. Thus, in addition to arranging geometrical design objects GDO at locations of the anatomy relative to the target site TS which correspond to physical contact of the pointer tip 114, the CAD program may also be configured to allow geometrical design objects GDO to be arranged based on local virtual references LVR which are "projected" below the surface contacted by the pointer tip 114 (e.g., projected into or through the bone). Other configurations are contemplated.

Figure 23A:
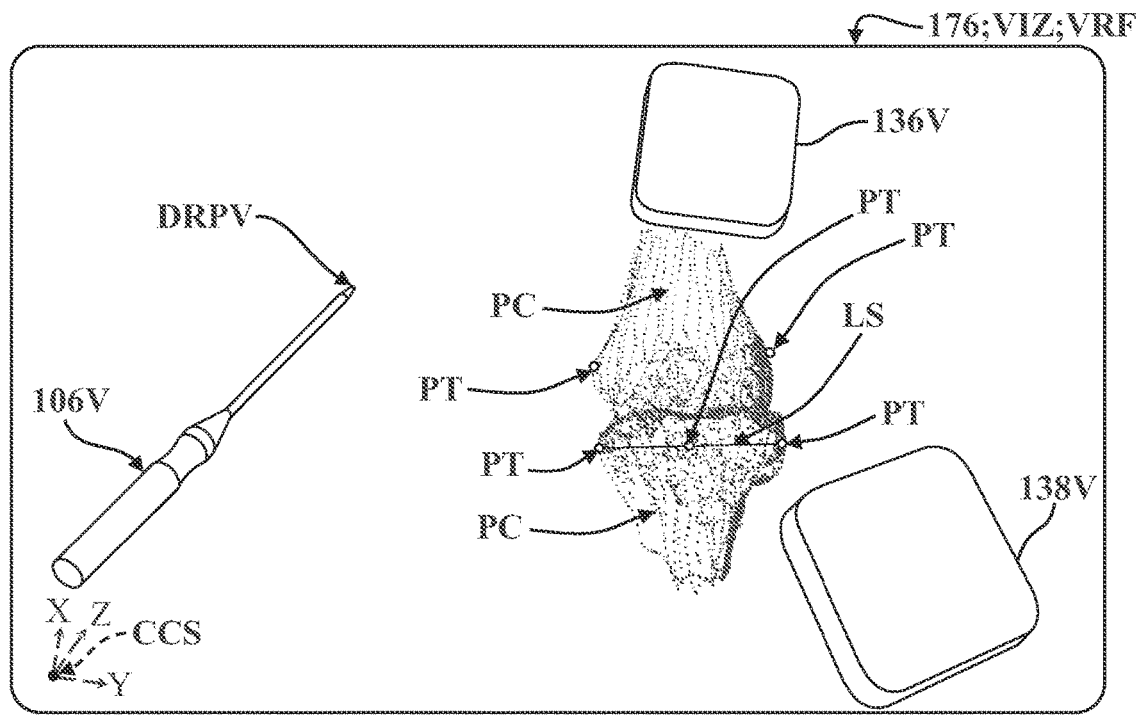
FIG. 23A is another representation of the GUI of FIG. 20A, shown with the new object function selected to create a line segment using defined objects arranged within the virtual reference frame selectable from a list.
Figure 23A:
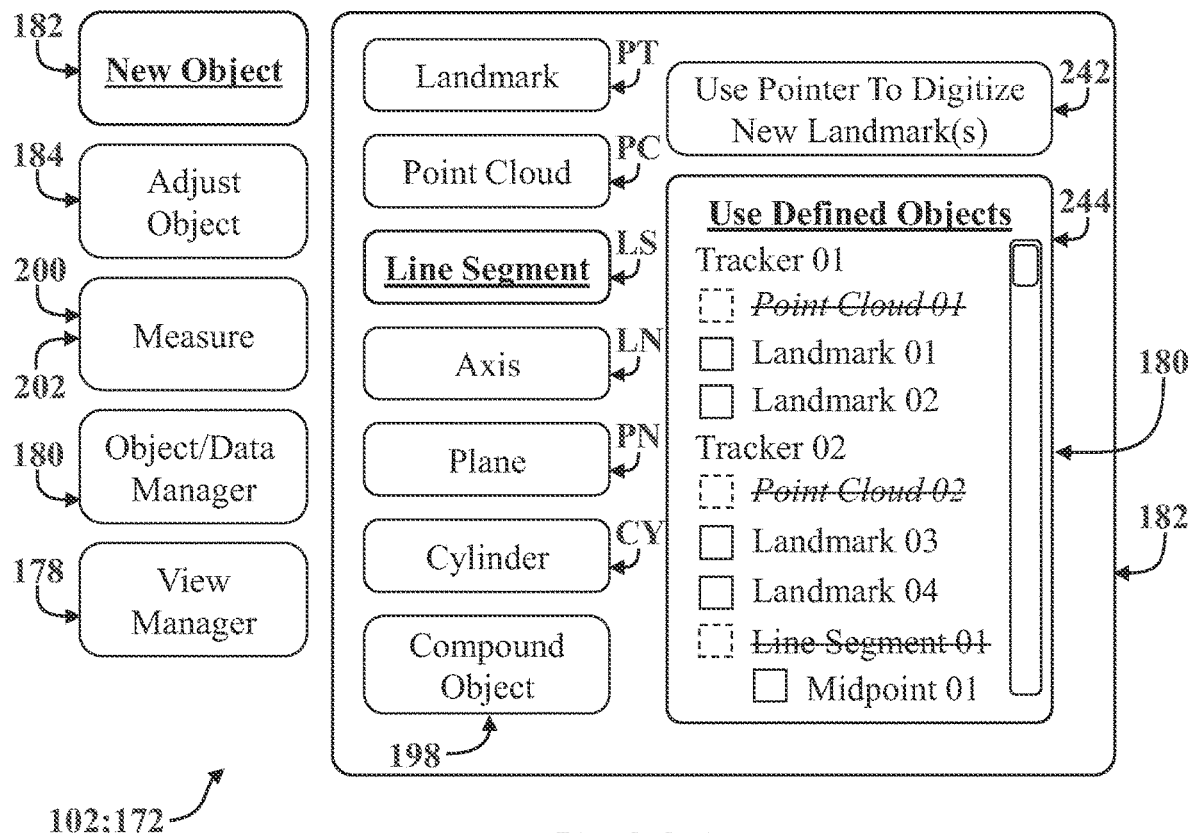

Referring now to FIG. 23A, options for arranging a new geometrical design object GDO realized as a line segment LS are shown. Here, the surgeon is able to select between a use pointer to digitize new landmark(s) option 242 or a use defined object option 244. Here, the use pointer to digitize new landmark(s) option 242 may correspond to the at pointer tip option 238 and/or the offset from pointer tip option 238 described above, and generally represents one embodiment of the bottom-up approach 186 described above. On the other hand, the use defined objects option 244 may correspond to the with algorithm/form defined objects option 240 described above, and generally represents one embodiment of the top-down approach 188 described above.

In FIG. 23A, the use defined objects option 244 has been selected (e.g., with the top-down approach 188), and a representation of the object/data manager 180 is shown. Here, the surgeon is able to construct the new line segment LS using only some of the geometrical design objects GDO (or the local virtual references LVR and/or calculated virtual references CVR associated therewith). This is illustrated by some of the existing geometrical design objects GDO being unavailable for the surgeon to select (or "greyed out"), which may be determined by the CAD program 102 contextually based on, among other things, the type of surgical step being planned, the type of surgical procedure to be executed, the types of different geometrical design objects GDO which have already been arranged within the virtual reference frame VRF, and the like. Other configurations are contemplated.

Figure 23B:
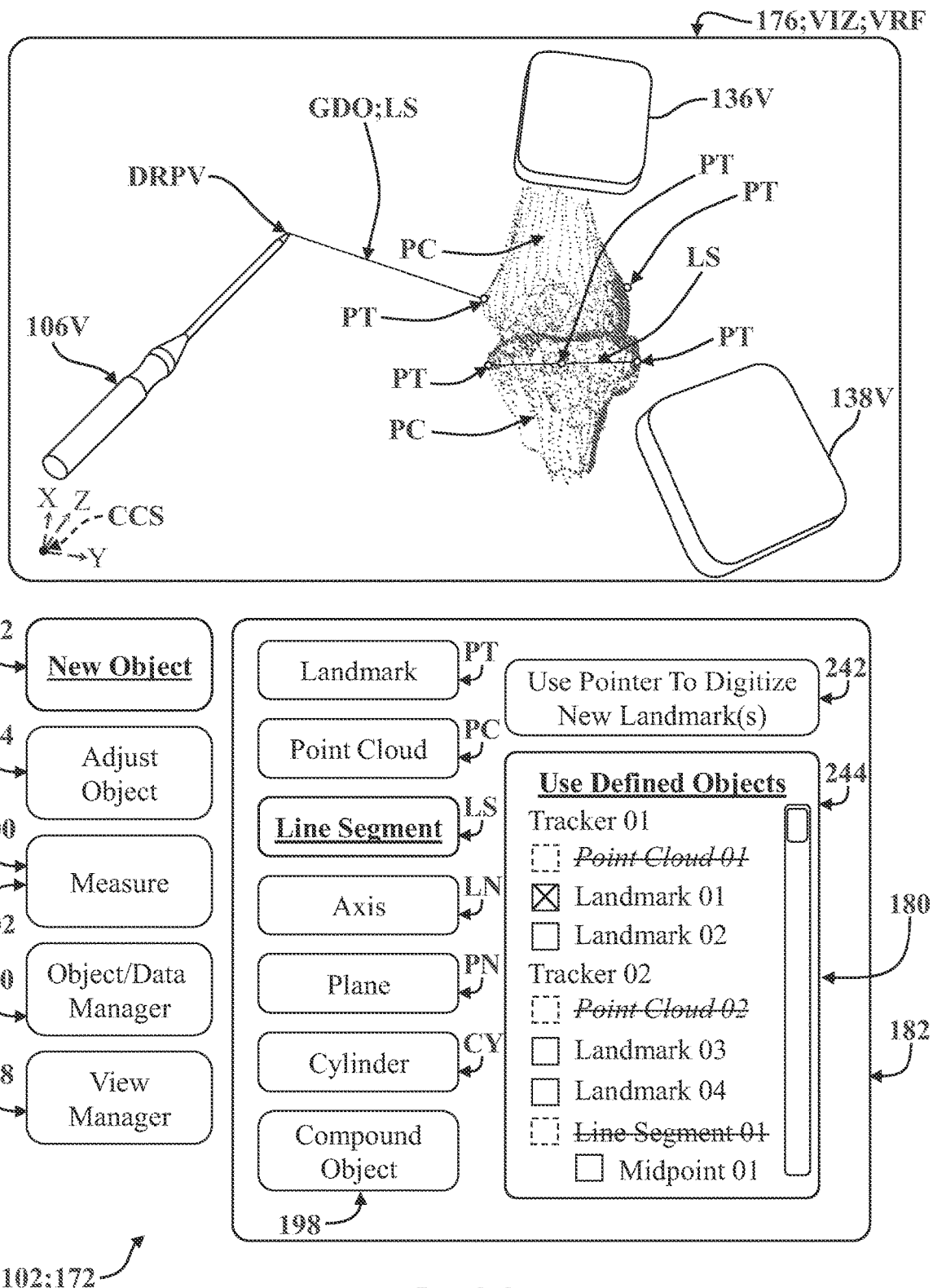
FIG. 23B is another representation of the GUI of FIG. 23A, shown with the new object function still selected to create the line segment using a point selected from the list, and shown with the line segment fixed to the point and to a pointer tip of a virtual representation of the digitization device rendered within the visualization.
Figure 23C:
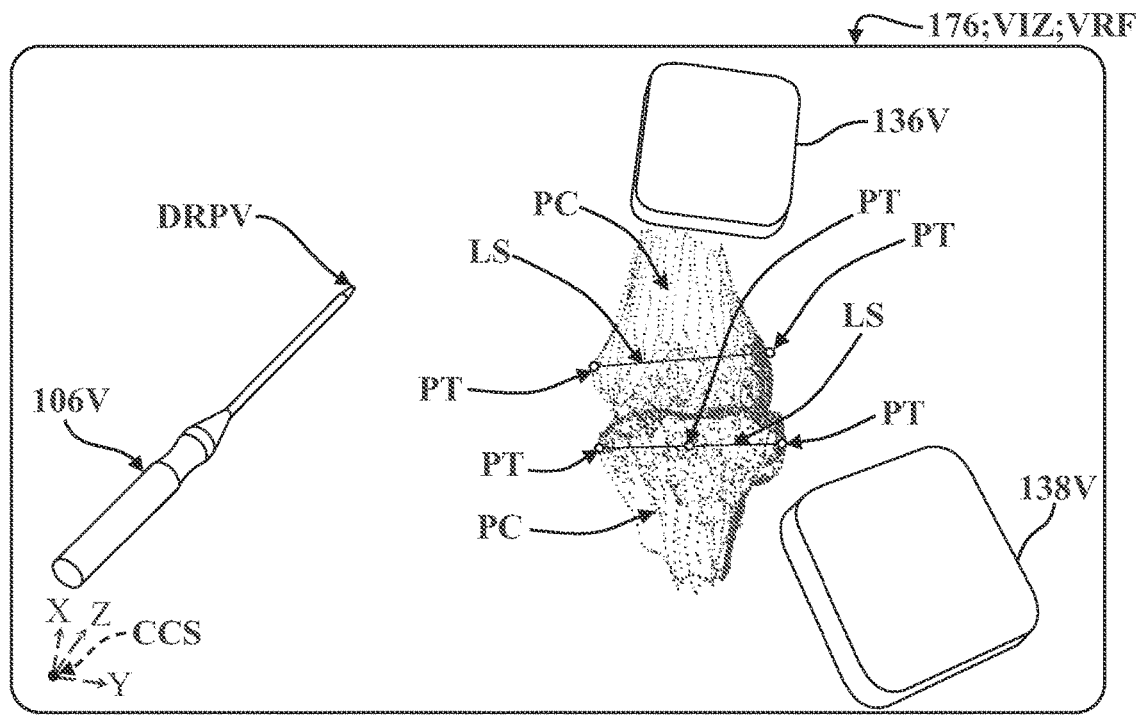
FIG. 23C is another representation of the GUI of FIG. 23B, shown with the new object function still selected to create the line segment using two points selected from the list, and shown with the line segment fixed to both points and unfixed from the pointer tip of the virtual representation of the digitization device rendered within the visualization.
Figure 23C:
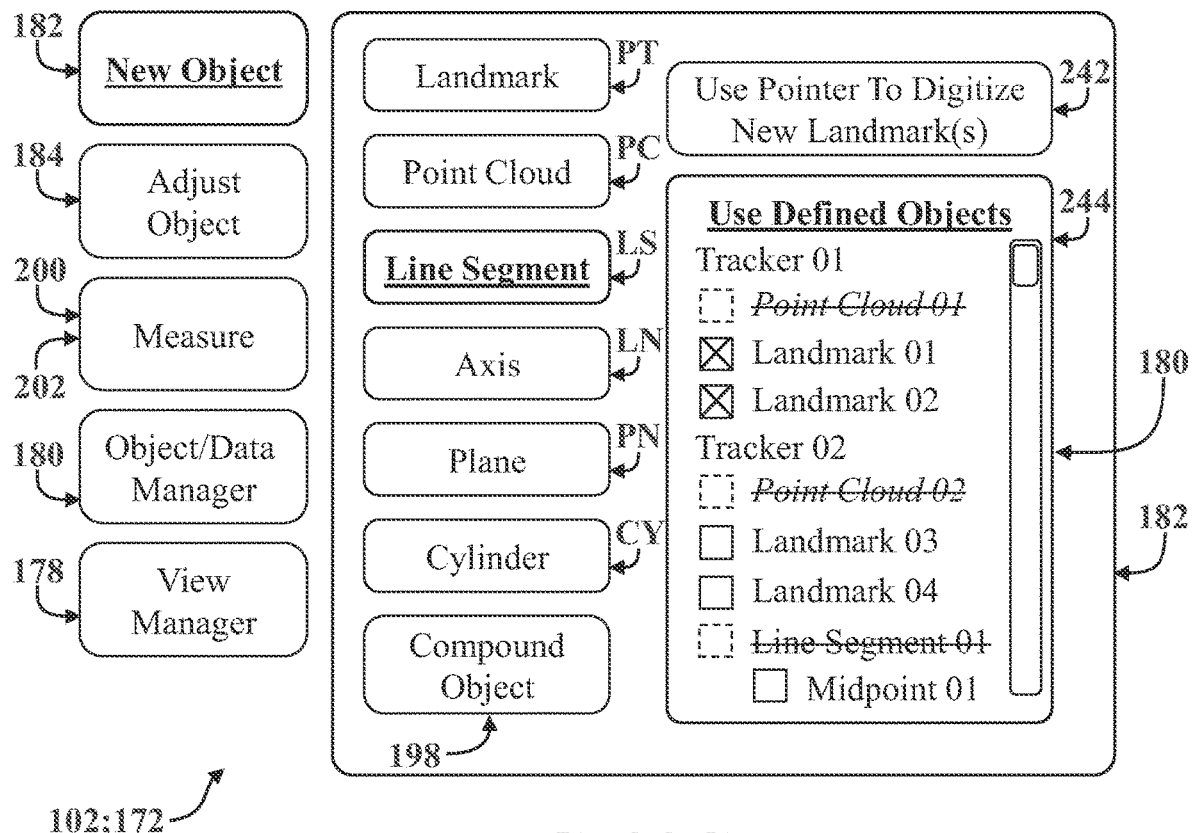

Following from FIG. 23A, in FIG. 23B the surgeon has selected the use defined objects option 244 to use an existing point PT ("Landmark 01") to construct the line segment LS (e.g., by using the registered local virtual reference LVR which defines "Landmark 01"). Here, the CAD program switches from the top-down approach 188 to the mixed approach 190, automatically, by rendering the line segment LS between the previously-selected point PT ("Landmark 01") and the virtual digitizer reference point DRPV. While not shown in FIG. 23B, the surgeon could continue with the mixed approach 190 by subsequently positioning the pointer tip 114 relative to the target site TS and establishing a new local virtual reference LVR which, when registered by the CAD program, would then fully define the line segment LS. Conversely, and as is shown in FIG. 23C, the surgeon has decided to continue with the top-down approach 188 by selecting another existing point PT ("Landmark 02") from the representation of the object/data manager 180 to construct and fully define the line segment LS (e.g., by using the registered local virtual reference LVR which defines "Landmark 02").

Figure 24A:
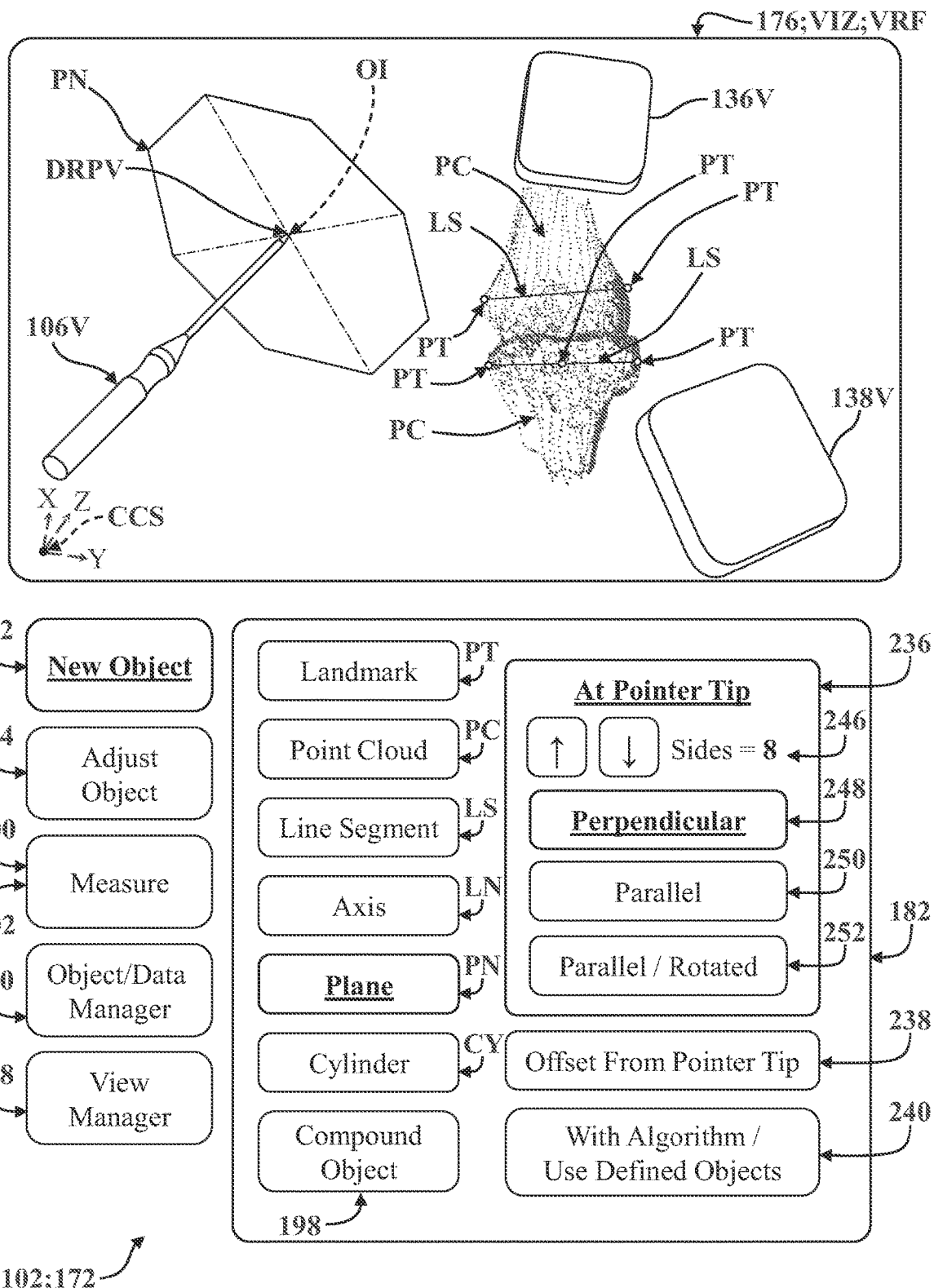
FIG. 24A is another representation of the GUI of FIG. 20A, shown with the new object function selected to create an octagonal plane fixed to a pointer tip of a virtual representation of the digitization device rendered within the visualization and arranged in a perpendicular fashion relative to the virtual representation of the digitization device.
Figure 24B:
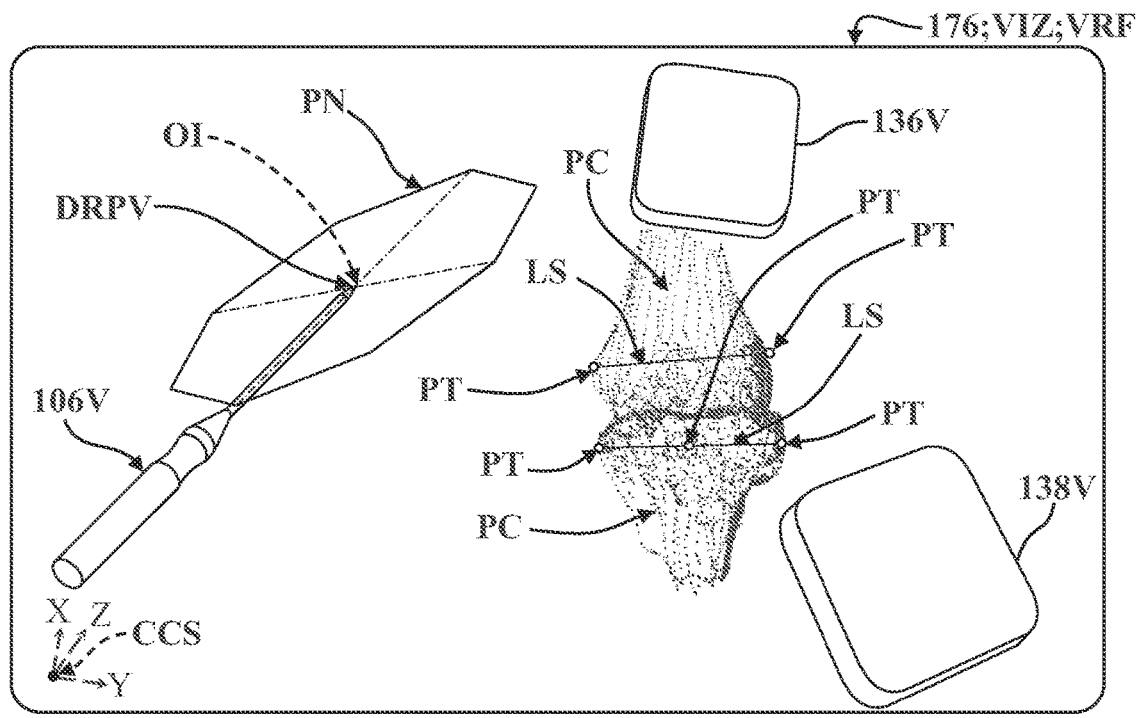
FIG. 24B is another representation of the GUI of FIG. 20A, shown with the new object function selected to create an octagonal plane fixed to a pointer tip of a virtual representation of the digitization device rendered within the visualization and arranged in a parallel fashion relative to the virtual representation of the digitization device.
Figure 24B:
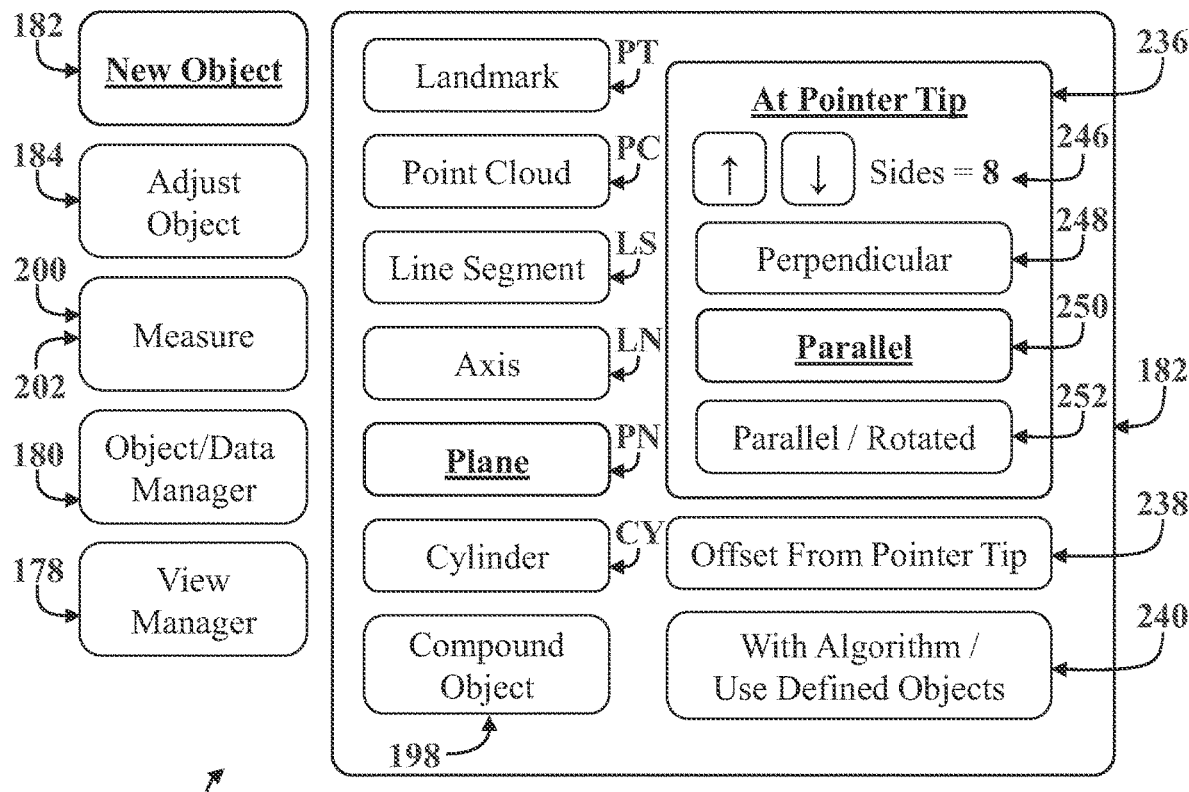
Figure 24C:
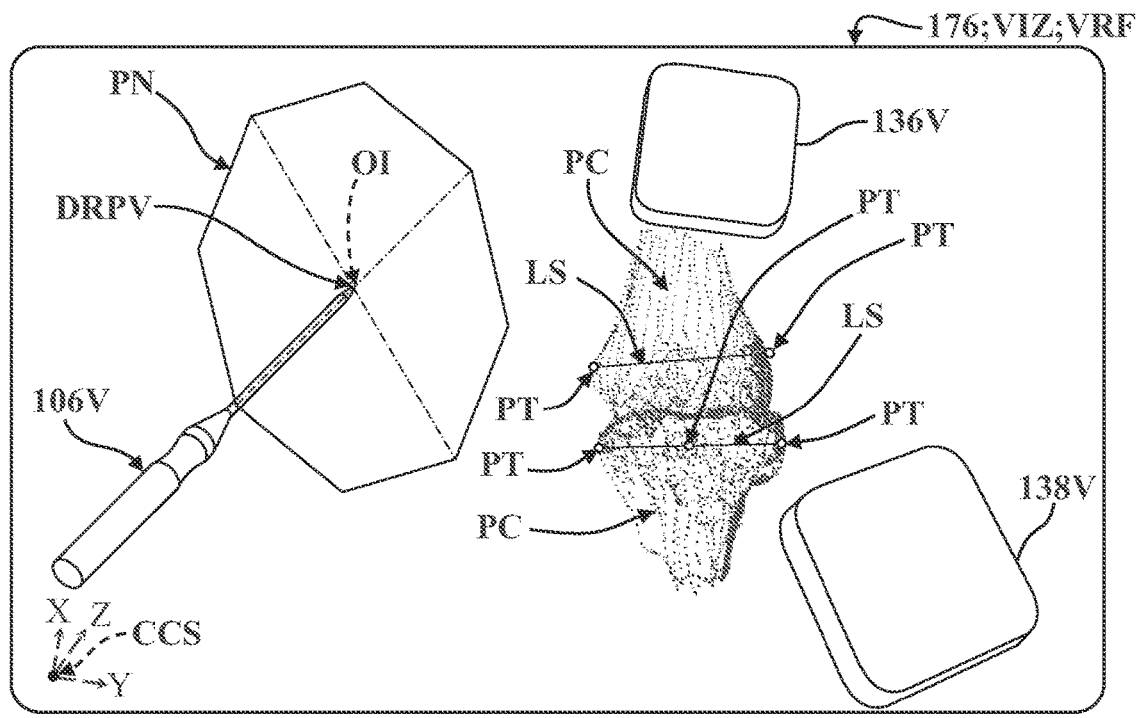
FIG. 24C is another representation of the GUI of FIG. 20A, shown with the new object function selected to create an octagonal plane fixed to a pointer tip of a virtual representation of the digitization device rendered within the visualization and arranged in a parallel and rotated fashion relative to the virtual representation of the digitization device.
Figure 24C:
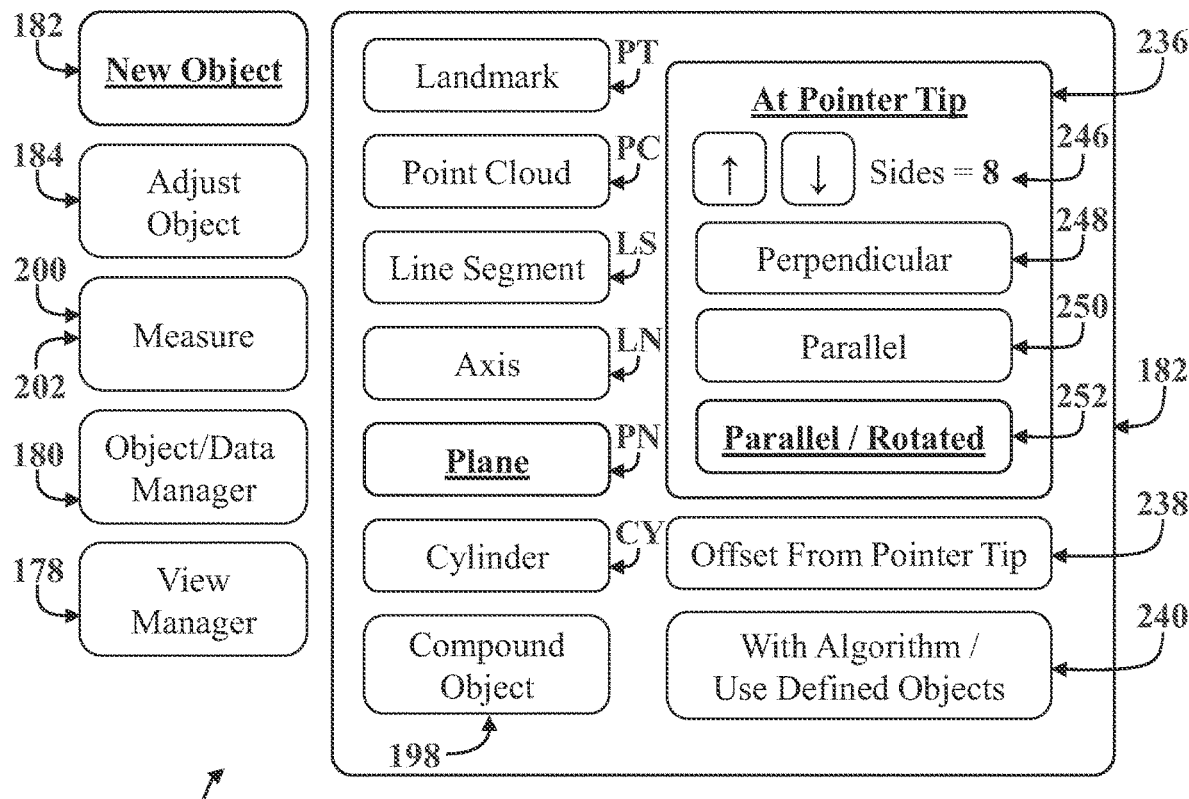

Referring now to FIGS. 24A-24C, as noted above, different types of geometrical design objects GDO may be fixed relative to the virtual the virtual digitizer reference point DRPV in different ways (e.g., with the at pointer tip option 236 or the offset from pointer tip option 238) to, among other things, help the surgeon initially orientate a new geometrical design object (e.g., when following the top-down approach 188).

In FIG. 24A the surgeon has selected the at pointer tip option 236 to arrange a new geometrical design object GDO realized as a plane PN using the top-down approach 188 and the surgeon is presented with example contextual options related to initially arranging and fixing a new plane PN to the virtual digitization device 106V with the top-down approach 188. Specifically, the surgeon is presented with an adjust sides option 246, a perpendicular option 248, a parallel option 250, and a parallel/rotated option 252 to orientate and partially define an octagonal plane PN. In some embodiments, additional options could be displayed (e.g., to initially set the span length SL). Other configurations are contemplated.

In the embodiment illustrated in FIG. 24A, the surgeon has fixed an octagonal plane PN perpendicular to the virtual digitization device 106V by using the adjust sides 246 option to use eight sides, and by using the perpendicular option 248 to orientate the object index OI of the plane (e.g., the normal vector) perpendicular to the virtual digitization device 106V.

In the embodiment illustrated in FIG. 24B, the surgeon has fixed an octagonal plane PN parallel to the virtual digitization device 106V by using the adjust sides 246 option to use eight sides, and by using the parallel option 250 to orientate the object index OI of the plane (e.g., the normal vector) parallel to the virtual digitization device 106V (compare FIG. 24B to FIG. 24A).

In the embodiment illustrated in FIG. 24C, the surgeon has fixed an octagonal plane PN parallel and rotated ninety-degrees (compare to FIG. 24B) to the virtual digitization device 106V by using the adjust sides 246 option to use eight sides, and by using the parallel/rotated option 252 to orientate the object index OI of the plane (e.g., the normal vector) parallel to and rotated relative to the virtual digitization device 106V (compare FIG. 24C to FIG. 24B).

While the illustrative examples described above in connection with FIGS. 24A-24C involve fixing octagonal planes PN to the virtual digitization device 106V, it will be appreciated that other types of different geometrical design objects GDO may be fixed to the virtual digitization device 106V in various ways without departing from the scope of the present disclosure.

Figure 25A:
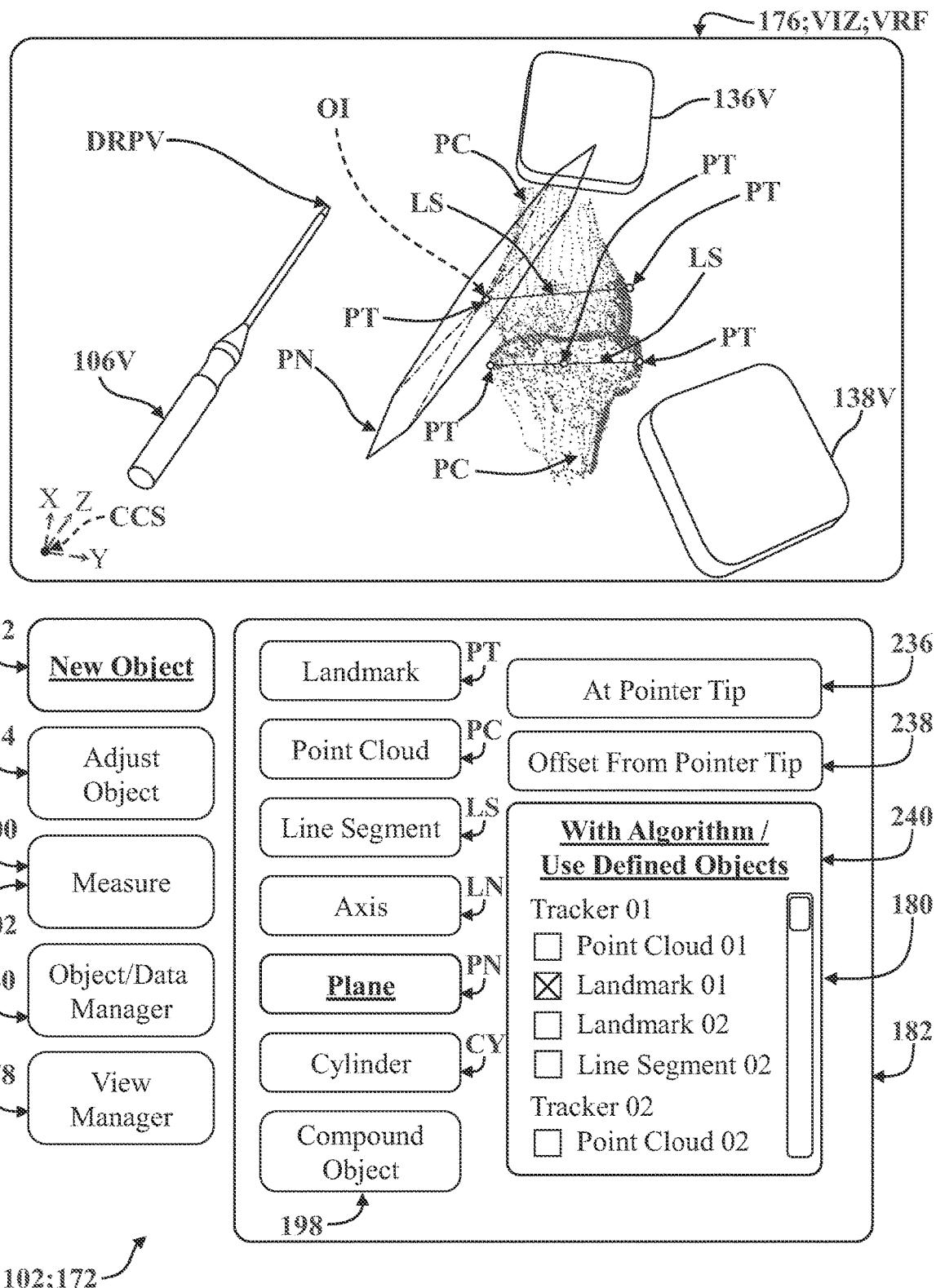
FIG. 25A is another representation of the GUI of FIG. 20A, shown with the new object function selected to create an octagonal plane shown fixed to a point selected from a list of objects arranged within the virtual reference frame.
Figure 25B:
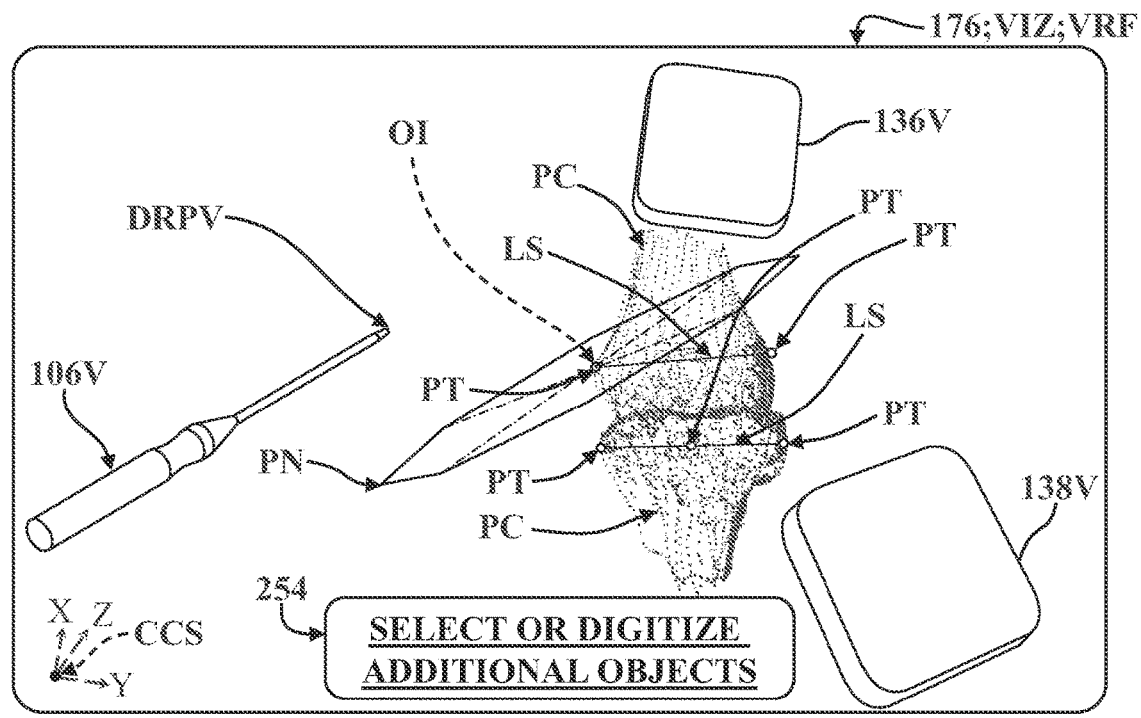
FIG. 25B is another representation of the GUI of FIG. 25A, shown with the octagonal plane fixed to the point and rotating about the point to follow movement of a virtual representation of the digitization device rendered within the visualization, and shown displaying a message prompting a user to select or digitize additional objects to fully define the octagonal plane.
Figure 25B:
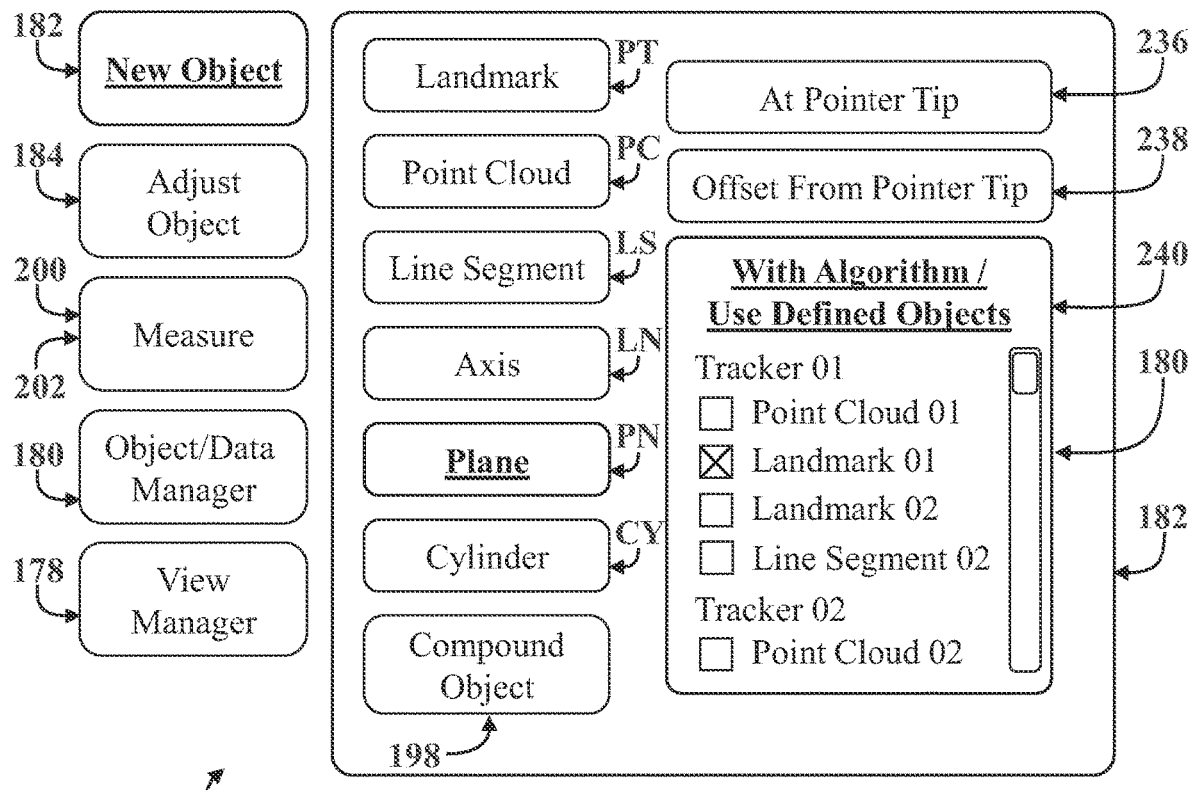

Referring now to FIG. 25A, continuing with the embodiment described above in connection with FIGS. 24A-24C, the surgeon has opted to arrange the octagonal plane using the with algorithm/from defined objects option 240, and has selected an existing point PT ("Landmark 01") to position the object index OI of the octagonal plane PN (e.g., by using the registered local virtual reference LVR which defines "Landmark 01"). Here, the CAD program switches to the mixed approach 190 such that the octagonal plane PN rotates about the existing point PT ("Landmark 01") to follow the orientation of the virtual digitization device 106V (compare FIGS. 25A-25B). While in the mixed approach 190, in addition to rotating the octagonal plane PN about its object index OI relative to the existing point PT to follow the virtual digitization device 106V, the CAD program 102 presents a prompt 254 to the surgeon to either select additional objects from a representation of the object/data manager 180 (e.g., local virtual references LVR and/or calculated virtual references CVR associated with existing geometrical design objects GDO), or to digitize additional objects (e.g., establish and register a new local virtual reference LVR).

Figure 25C:
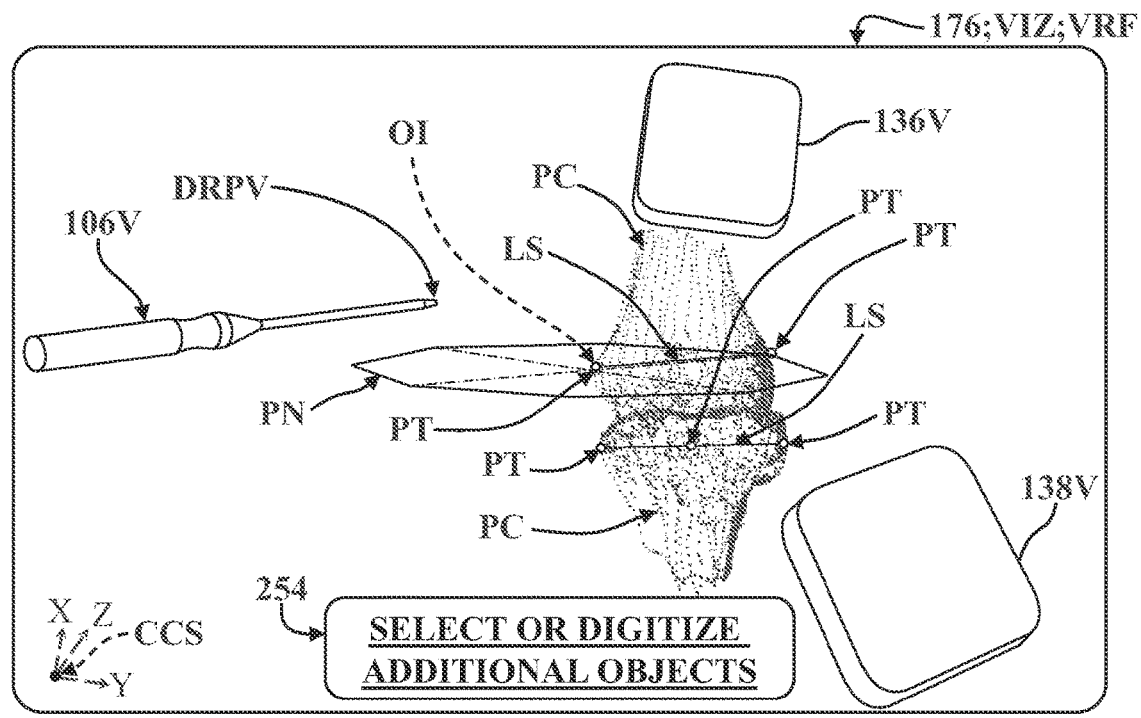
FIG. 25C is another representation of the GUI of FIG. 25B, shown with the octagonal plane fixed to the point and rotated about the point to fix to another point selected from the list of objects arranged within the virtual reference frame, and shown still displaying the message prompting the user to select or digitize additional objects to fully define the octagonal plane.
Figure 25C:
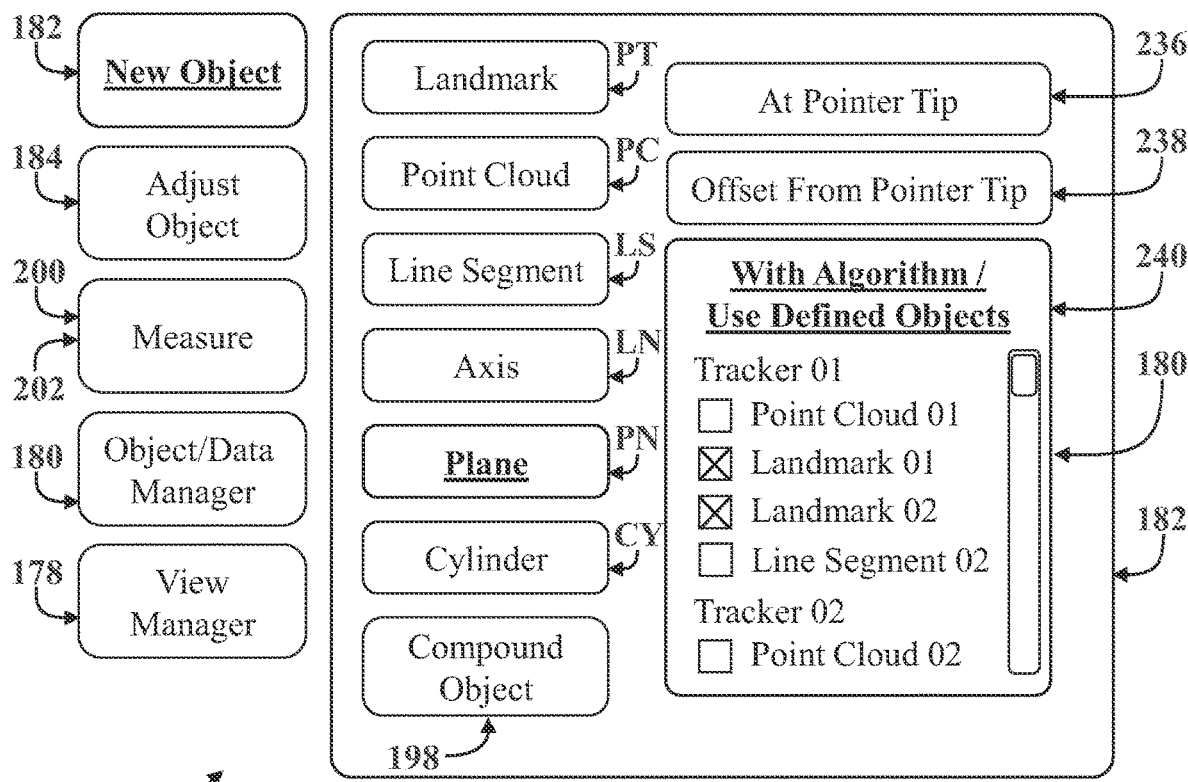

In FIG. 25C, following with the mixed approach 190, the surgeon has selected another existing point PT ("Landmark 02") using the representation of the object/data manager 180 to continue defining the octagonal plane PN (e.g., such as may be used to define the span length SL). Here in FIG. 25C, because the octagonal plane PN is not yet fully defined, it still remains partially fixed to the virtual digitization device 106V, and the prompt 254 continues to direct the surgeon to either select additional objects or to digitize additional objects.

Figure 25D:
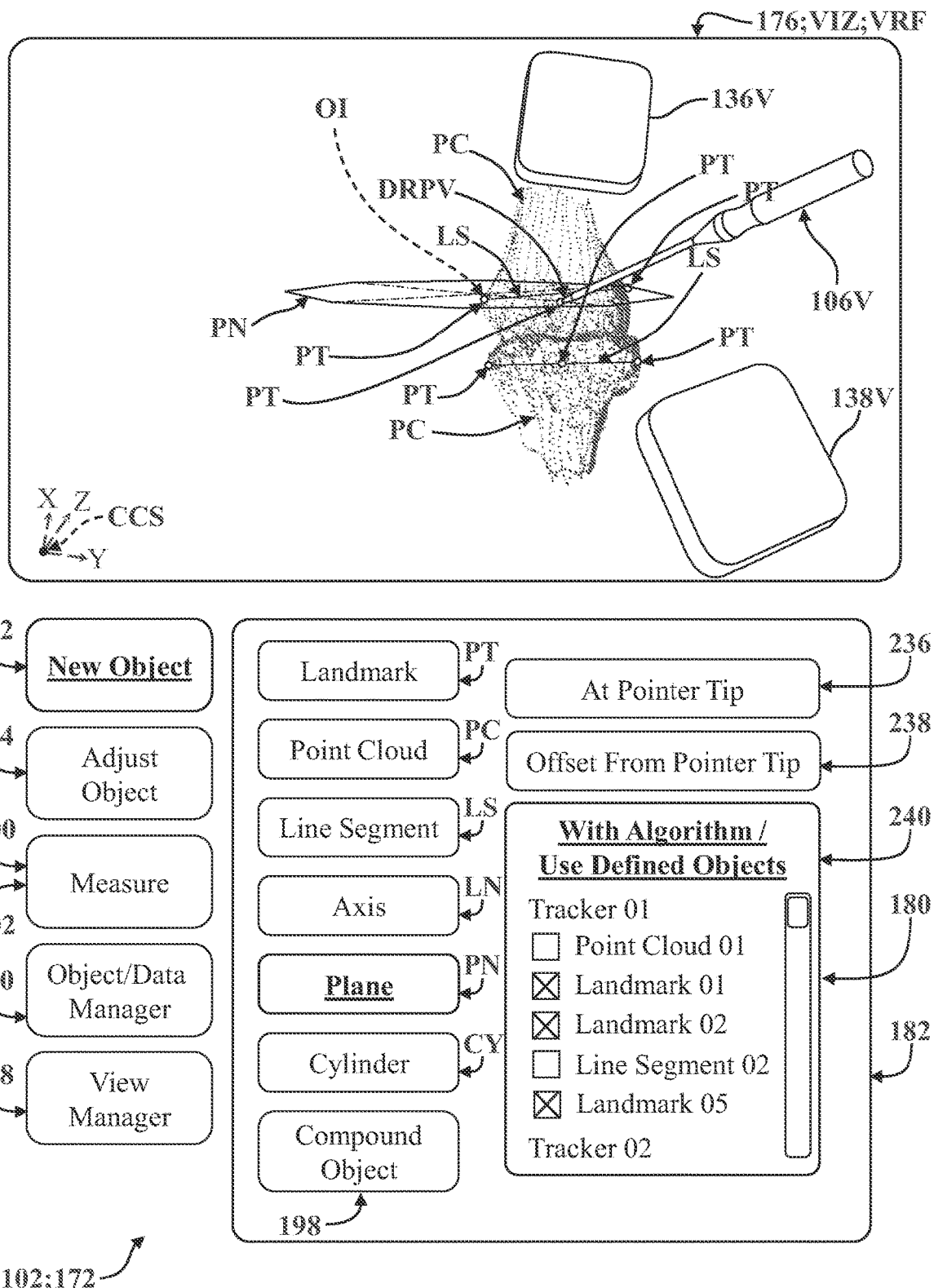
FIG. 25D is another representation of the GUI of FIG. 25C, shown with the octagonal plane fixed to a pointer tip of the virtual representation of the digitization device rendered within the visualization, with the octagonal plane having been fully-defined with a newly-registered local virtual reference established as another point.

In FIG. 25D, the surgeon has opted to digitize a new local virtual reference LVR represented as a point PT ("Landmark 05") arranged at one of the corners of the octagonal plane PN, established such as by positioning the pointer tip 114 at the target site TS and actuating the pointer control input 116 of the digitization device 106. The newly-created point PT ("Landmark 05") is registered in the object/data manager 180 and is shown as being associated with the first patient tracker 136 ("Tracker 01").

Figure 26A:
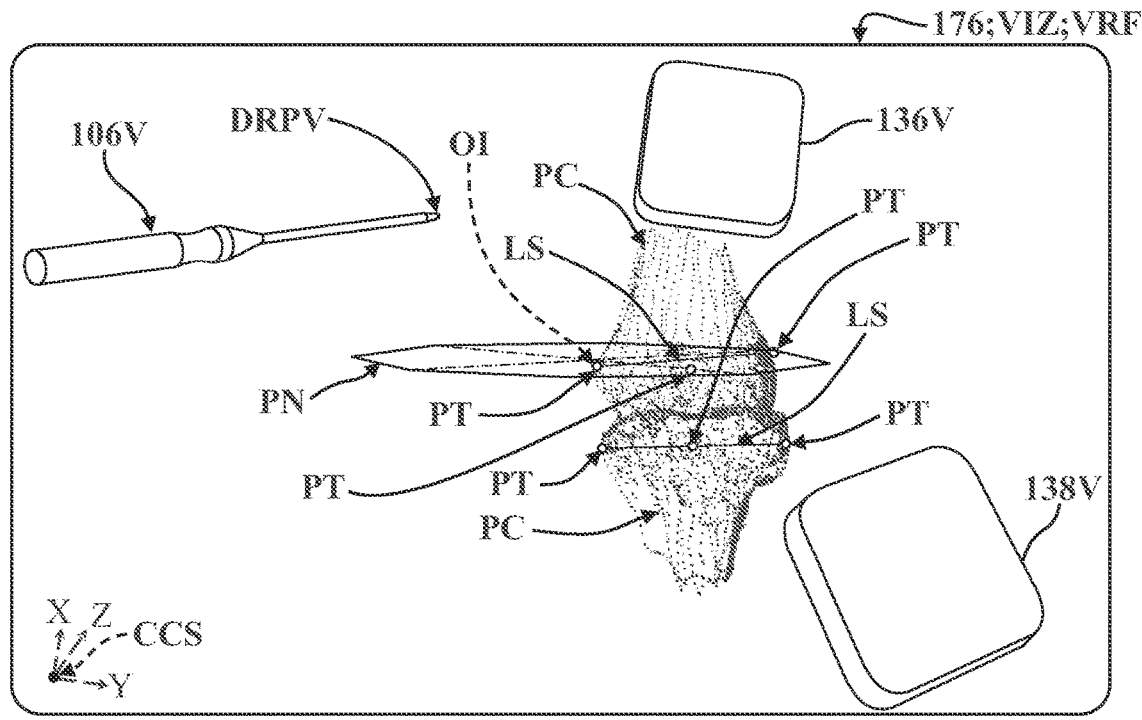
FIG. 26A is another representation of the GUI of FIG. 26A, shown with the adjust object function selected to construct a compound object from the selected octagonal plane arranged within the virtual reference frame.
Figure 26A:
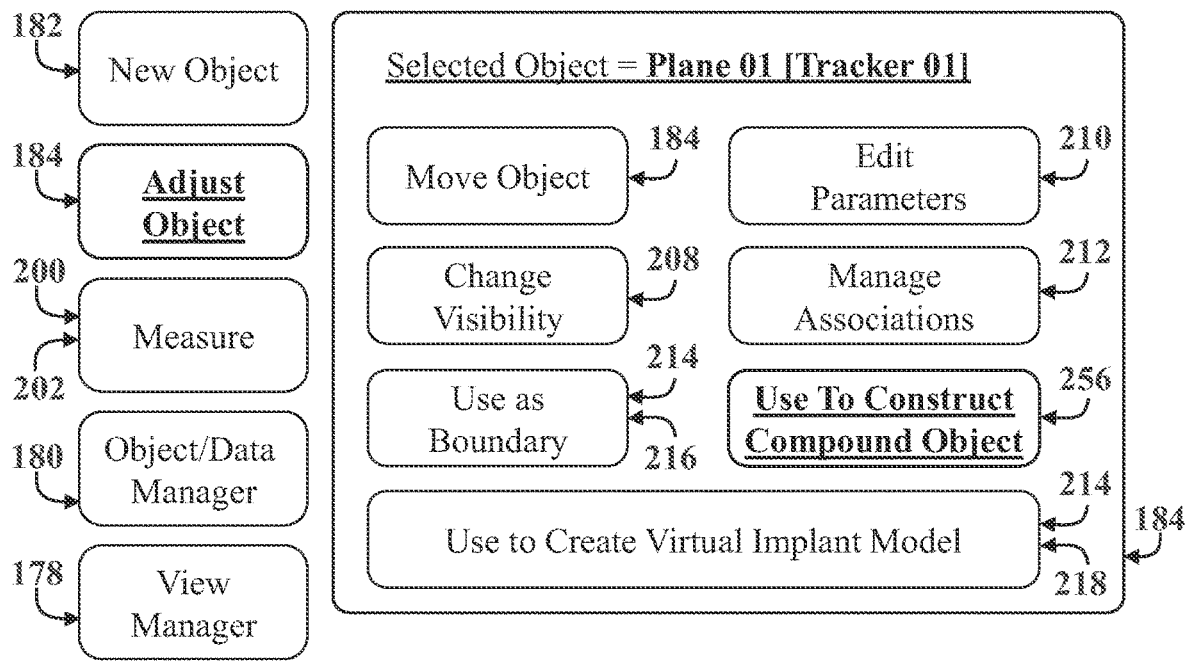
Figure 26B:
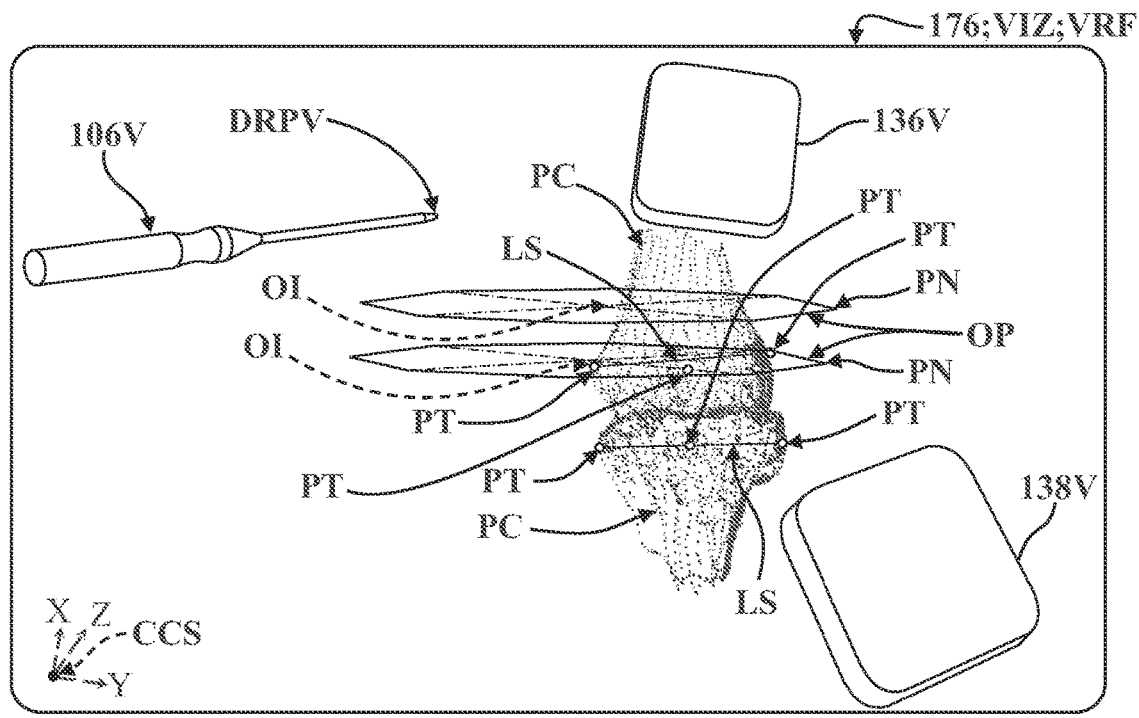
FIG. 26B is another representation of the GUI of FIG. 26A, shown depicting the new object function selected to construct the compound object from the selected octagonal plane, with the compound object selected as an osteotomy plane offset from the selected octagonal plane.
Figure 26B:
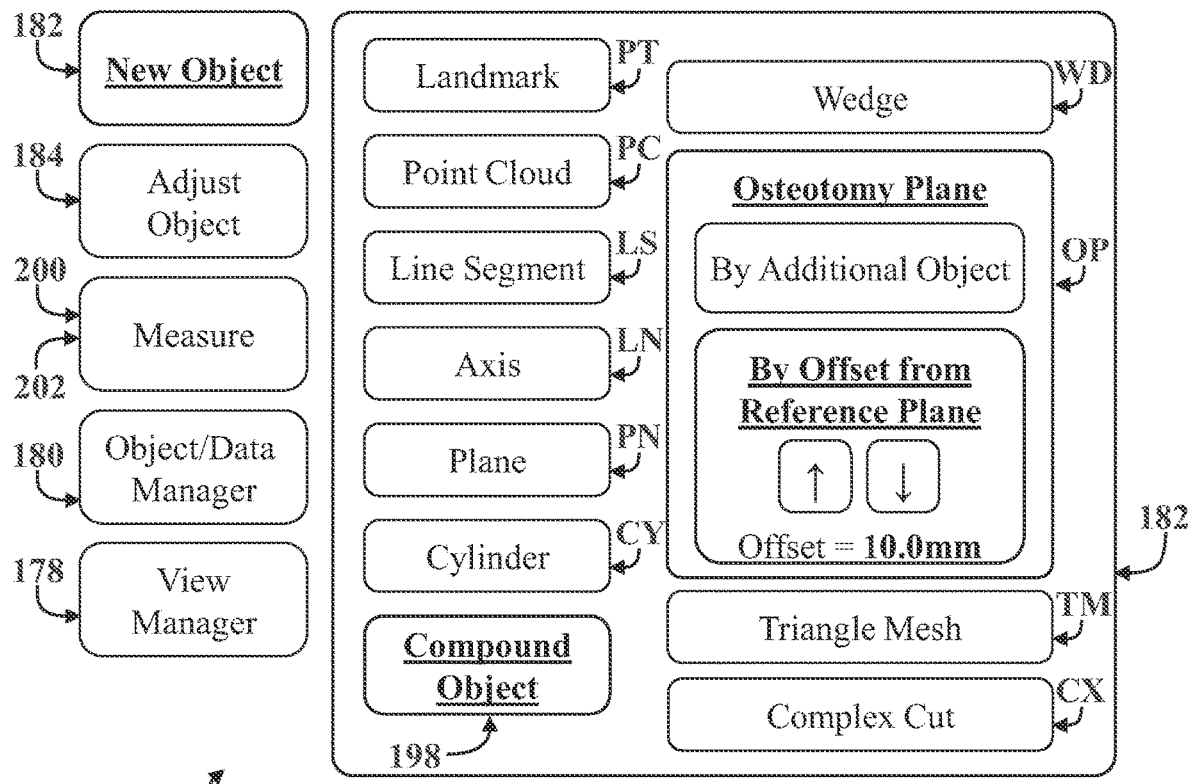

Referring now to FIG. 26A, the surgeon has selected, using the existing object arrangement section 184, a use to construct compound object option 254 selected using the octagonal plane PN ("Plane 1") created as described above in connection with FIGS. 20A-25D (specifically, see FIG. 25D). In FIG. 26B, continuing with the mixed approach 190, the GUI 172 of the CAD program 102 switches to the new object arrangement section 182 in order to allow the surgeon to create a compound type object 198 using the existing octagonal plane PN ("Plane 1"). Here, the surgeon has opted to create an osteotomy plane OP by creating another octagonal plane PN which is parallel to and spaced from from the existing octagonal plane PN ("Plane 01") at a cut distance. Here too, it will be appreciated that the various arrangement, configuration, and navigation of the GUI 172 of the CAD program 102 described above in connection with FIGS. 20A-26B is non-limiting. Other configurations are contemplated.

As noted above, the surgical system 100, the CAD program 102, and the various methods and computer-implemented techniques of the present disclosure enable the surgeon to arrange different types of geometrical design objects GDO within the virtual reference frame VRF based on one or more registered local virtual references LVR established using the digitization device 106 in order to facilitate ad-hoc, intraoperative planning of surgical steps utilized during execution of surgical procedures. It will be appreciated that different surgical steps may be utilized for different surgical procedures, and that the same type of surgical procedure may be carried out using different types of surgical steps, arranged in different orders and/or sequences to accommodate particular workflows, methodologies, and the like. In addition to facilitating intraoperative planning of surgical steps, as noted previously, the surgical system 100, the CAD program 102, and the various methods and computer-implemented techniques of the present disclosure can also generate tool control data CZ which may be utilized to control operation of the surgical tool 122 based on geometrical design objects GDO which were arranged intraoperatively within the virtual reference frame VRF.

While the present disclosure is not limited to any one particular surgical procedure, surgical step thereof, or workflow associated therewith, FIGS. 27-49 sequentially depict certain surgical steps which may be intraoperatively planned and executed, according to the embodiments of the surgical system 100 and the cad program 102 described herein, in connection with performing femoral neck osteotomy. Here, the target site TS comprises the femoral neck FN of the femur F which, in this example illustration, is to be resected such that the femoral head FH of the femur F can be removed and a prosthetic implant can be subsequently attached to the femur F (e.g., an artificial hip joint used in connection with total hip arthroplasty; not shown herein).

Figure 27:
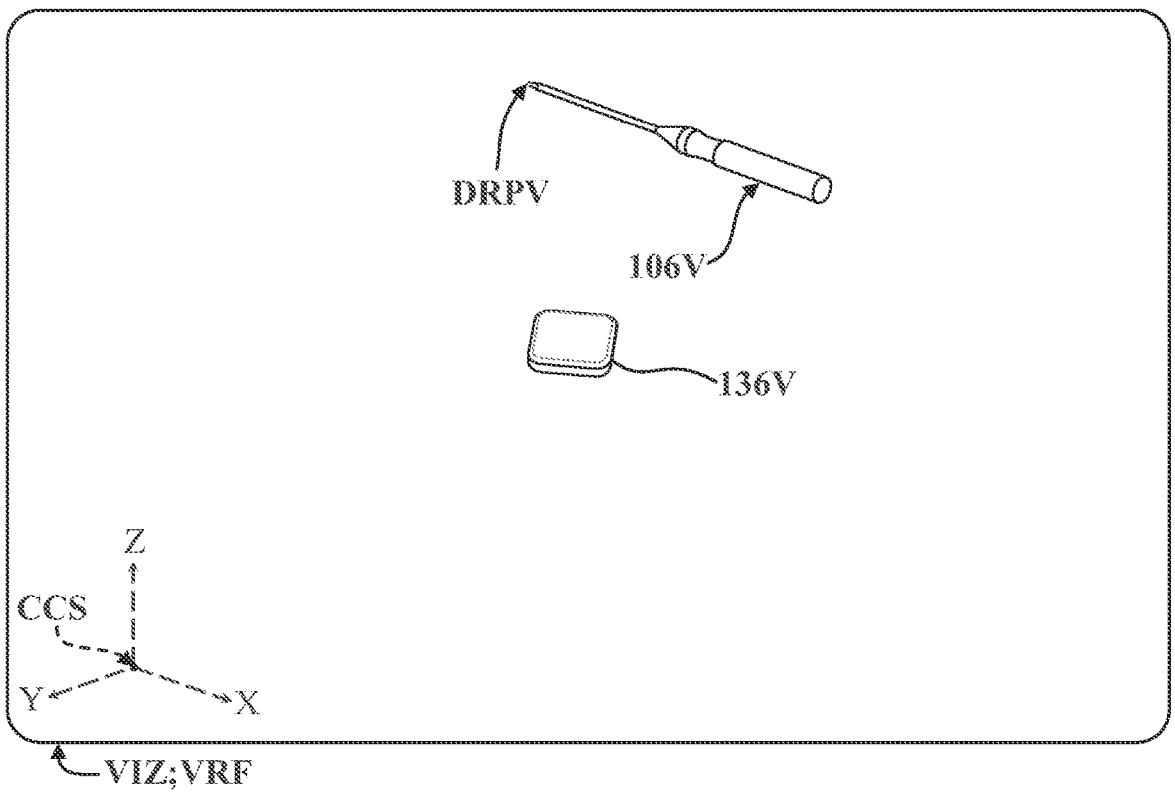
FIG. 27 is a partial perspective view of the digitization device, the patient tracker, and the femur of FIG. 18 shown adjacent to a visualization of a virtual reference frame rendered with the CAD program of FIG. 2, the visualization depicting virtual representations of the patient tracker and the digitization device rendered within the visualization based on tracked states of the digitization device and the patient tracker.
Figure 27:
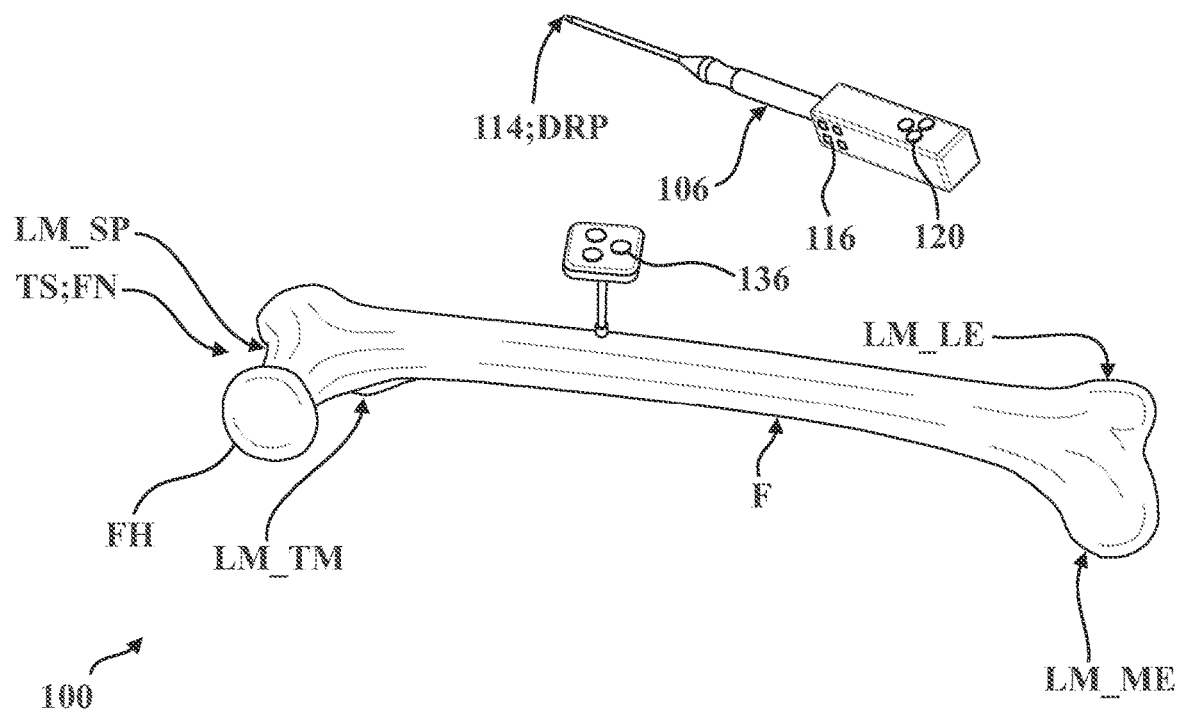

Referring now to FIG. 27, the first patient tracker 136 is shown attached to the femur F at a location spaced from the target site TS and spaced from the digitization device 106 such that the pointer tip 114 is out of contact with the patient's anatomy (e.g., positioned in air). FIG. 27 also shows the visualization VIZ of the virtual reference frame VRF rendered by the CAD program 102, displayed such as by one of the display units 148 of the navigation system 104. Also rendered in the visualization VIZ is the virtual digitization device 106V, the virtual first patient tracker 136V (hereinafter "virtual patient tracker"), and the CAD coordinate system CCS.

Figure 28:
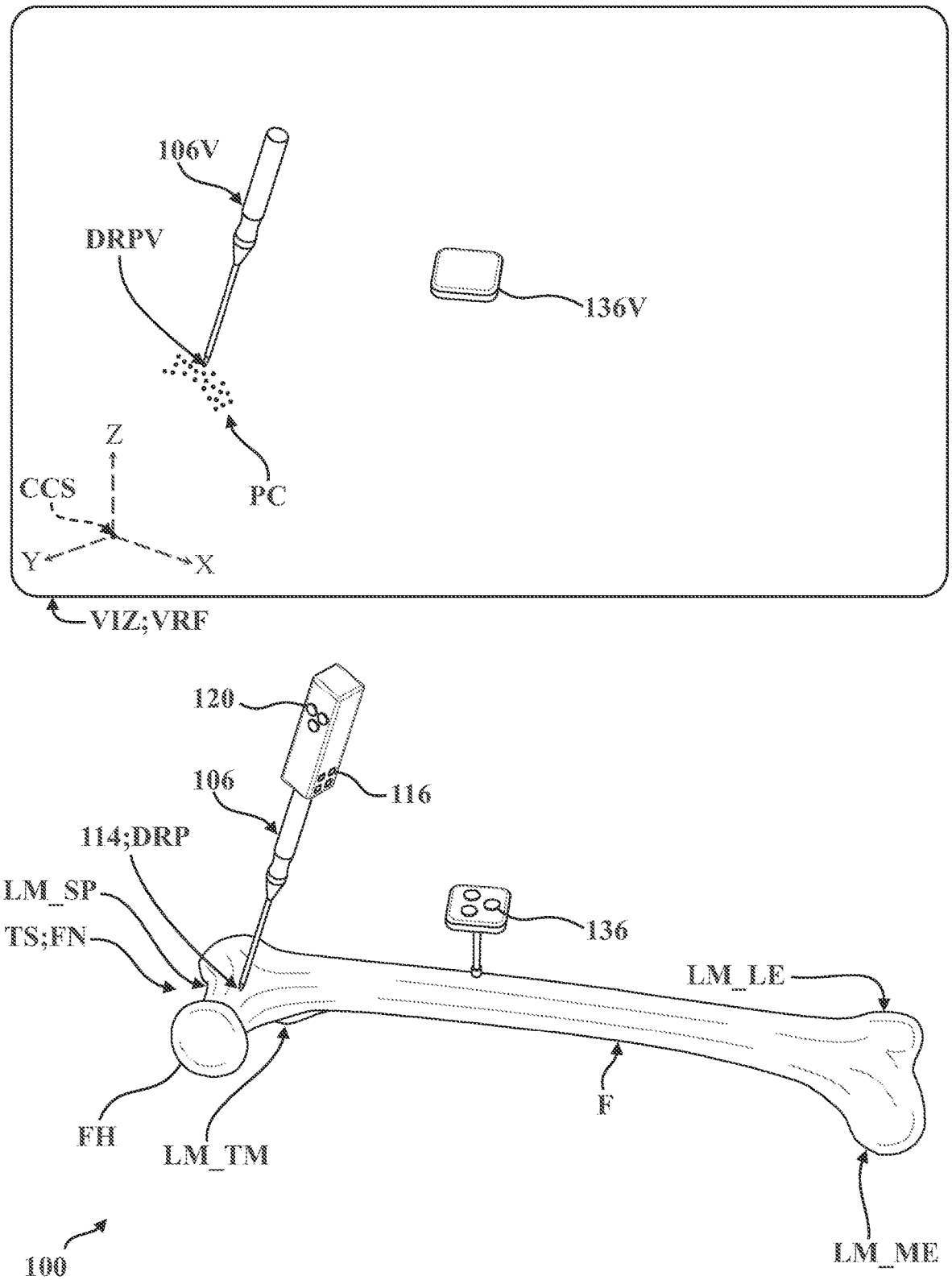
FIG. 28 is another partial perspective view of the digitization device, the patient tracker, the femur, and the visualization of the virtual reference frame of FIG. 27, shown with a pointer tip of the digitization device positioned along the femoral neck of the femur to digitize and establish a point cloud about the femoral neck, and shown with the corresponding point cloud rendered in the visualization.

Continuing from FIG. 27 to FIG. 28, the pointer tip 114 of the digitization device 106 is shown positioned about the femoral neck FN to demonstrate arranging a point cloud PC within the virtual reference frame VRF. The resulting point cloud PC is shown rendered in the visualization VIZ. In the illustrated embodiment, establishing and registering the point cloud PC about the femoral neck FN is used to help the surgeon initially orientate the visualization VIZ, and is later used to arrange an osteotomy plane OP.

Figure 29:
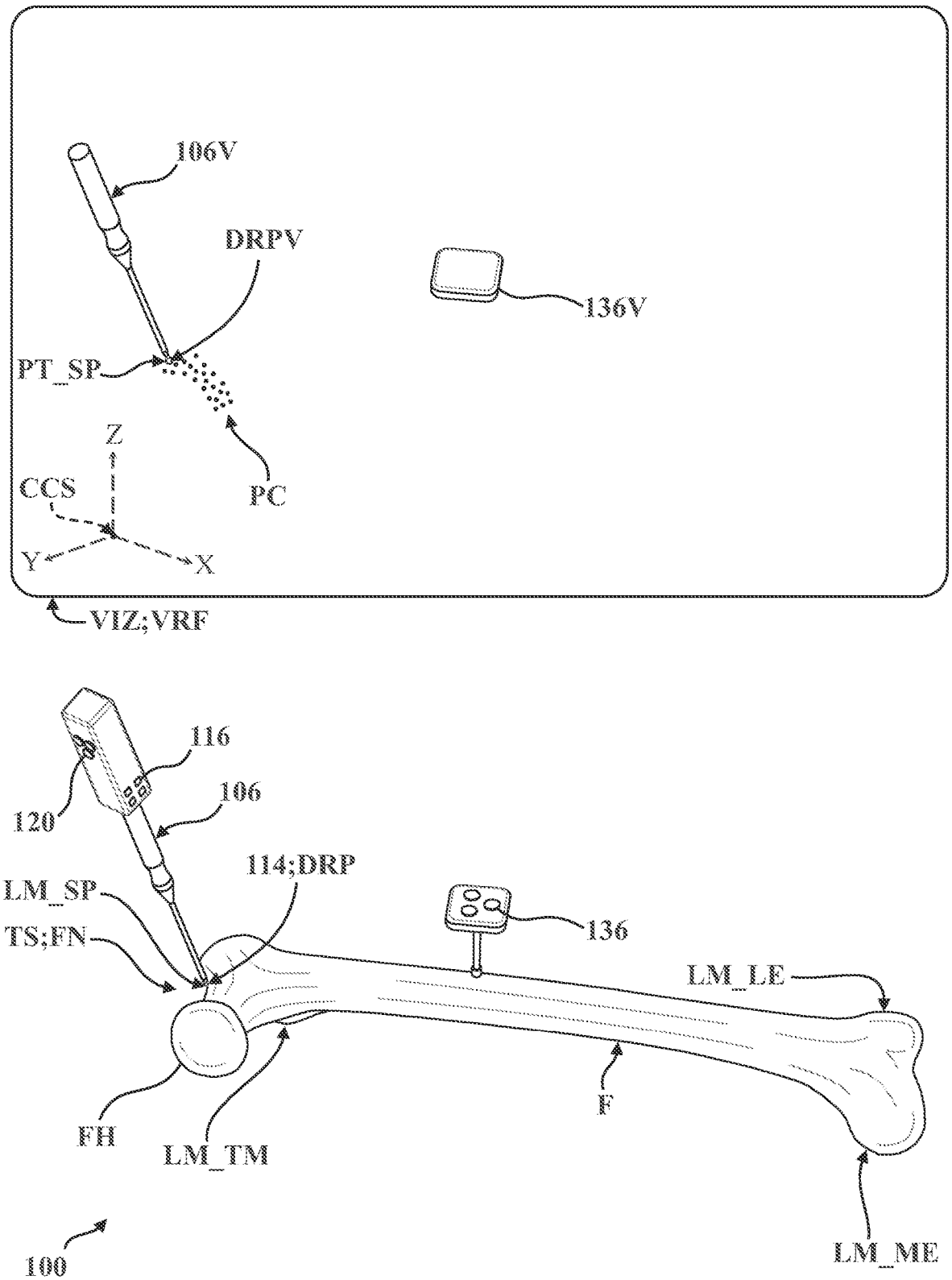
FIG. 29 is another partial perspective view of the digitization device, the patient tracker, the femur, and the visualization of the virtual reference frame of FIG. 28, shown with the pointer tip positioned at the saddle point landmark of the femur to digitize and establish a point at the saddle point, and shown with the corresponding point rendered in the visualization.

Continuing from FIG. 28 to FIG. 29, the pointer tip 114 of the digitization device 106 is shown positioned at the saddle point landmark LM_SP of the femur F to demonstrate arranging a point (hereinafter, "saddle point PT_SP") within the virtual reference frame VRF. The resulting saddle point PT_SP is shown rendered in the visualization VIZ.

Figure 30:
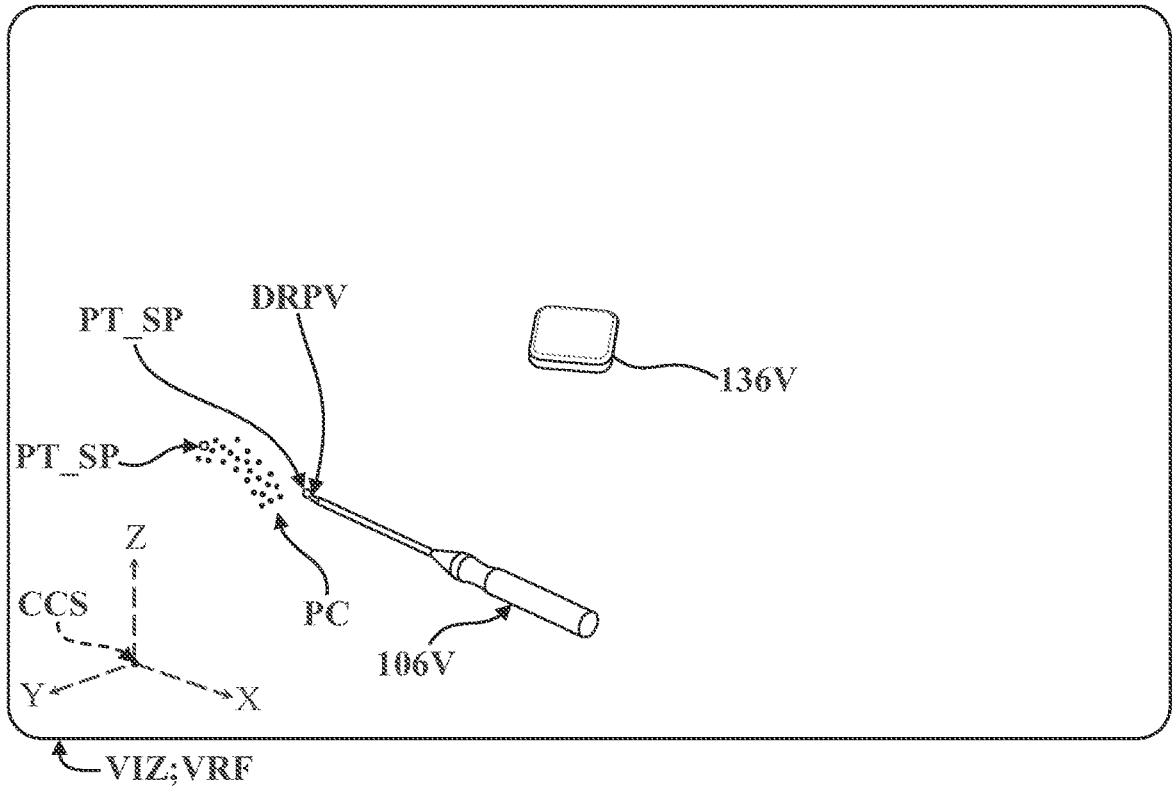
FIG. 30 is another partial perspective view of the digitization device, the patient tracker, the femur, and the visualization of the virtual reference frame of FIG. 29, shown with the pointer tip positioned at the trochanter minor landmark of the femur to digitize and establish a point at the trochanter minor landmark, and shown with the corresponding point rendered in the visualization.
Figure 30:
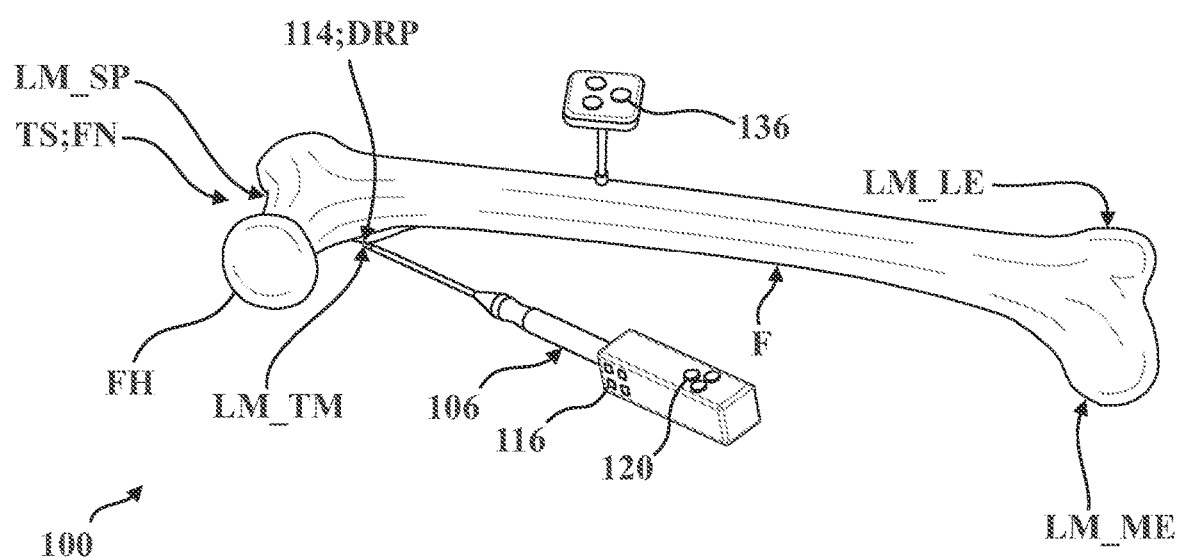

Continuing from FIG. 29 to FIG. 30, the pointer tip 114 of the digitization device 106 is shown positioned at the trochanter minor landmark LM_TM of the femur F to demonstrate arranging a point (hereinafter, "trochanter minor point PT_TM") within the virtual reference frame VRF. The resulting trochanter minor point PT_TM is shown rendered in the visualization VIZ.

Figure 31:
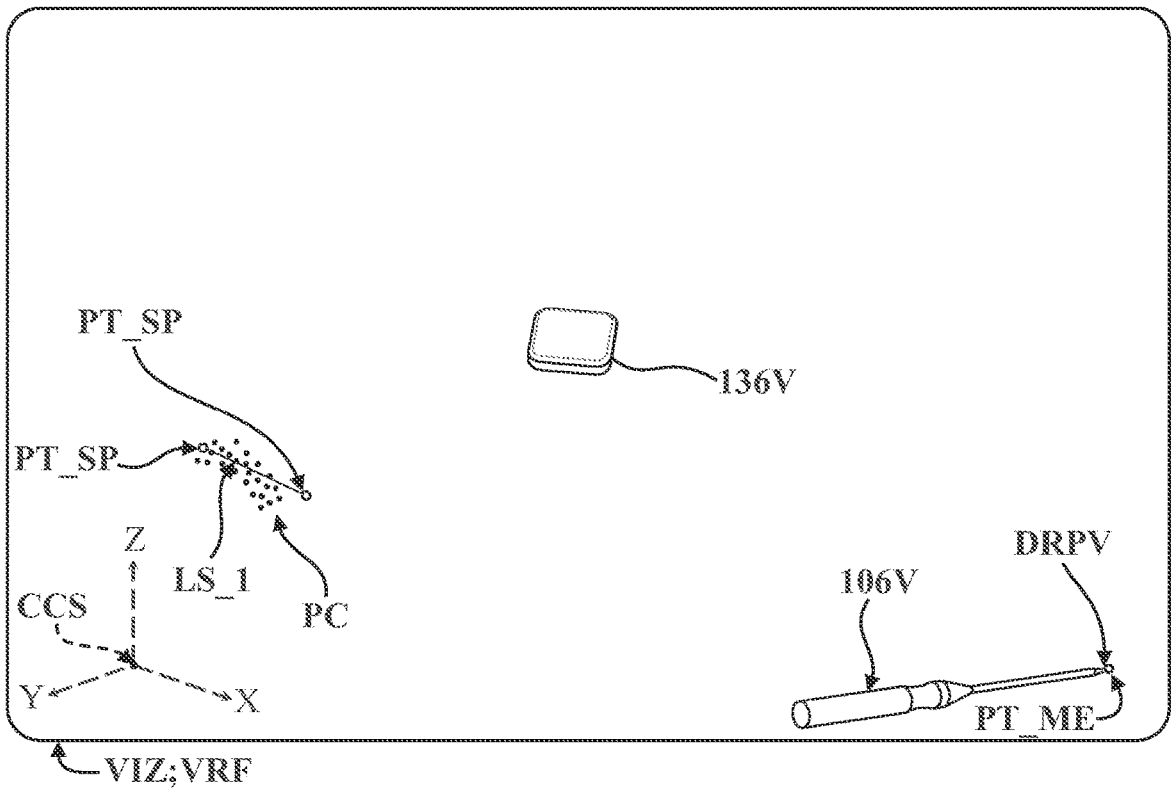
FIG. 31 is another partial perspective view of the digitization device, the patient tracker, the femur, and the visualization of the virtual reference frame of FIG. 30, shown with a line segment rendered within the visualization extending between the points established at the saddle point landmark and the trochanter minor landmark, shown with the pointer tip positioned at the medial epicondyle landmark of the femur to digitize and establish a point at the medial epicondyle landmark, and shown with the corresponding point rendered in the visualization.
Figure 31:
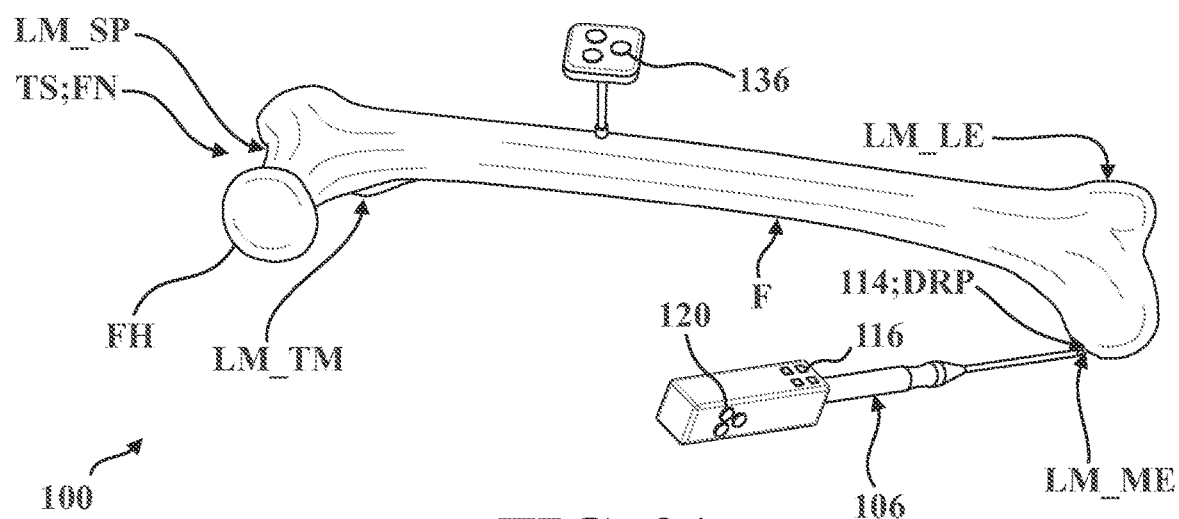

Continuing from FIG. 30 to FIG. 31, the pointer tip 114 of the digitization device 106 is shown positioned at the medial epicondyle landmark LM_ME of the femur F to demonstrate arranging a point (hereinafter, "medial epicondyle point PT_ME") within the virtual reference frame VRF. The resulting medial epicondyle point PT_ME" is shown rendered in the visualization VIZ. Further, in FIG. 31, the visualization VIZ depicts a line segment (hereinafter, "first line segment LS_1") arranged extending between the saddle point PT_SP and the trochanter minor point PT_TM.

Continuing from FIG. 31 to FIG. 32, the pointer tip 114 of the digitization device 106 is shown positioned at the lateral epicondyle landmark LM_LE of the femur F to demonstrate arranging a point (hereinafter, "lateral epicondyle point PT_LE") within the virtual reference frame VRF. The resulting lateral epicondyle point PT_LE is shown rendered in the visualization VIZ. Further, in FIG. 32, the visualization VIZ depicts a line segment (hereinafter, "second line segment LS_2") arranged extending between the medial epicondyle point PT_ME and the lateral epicondyle point PT_LE. Contextually, the second line segment LS_2 is the transepicondylar axis of the femur F.

Figure 32:
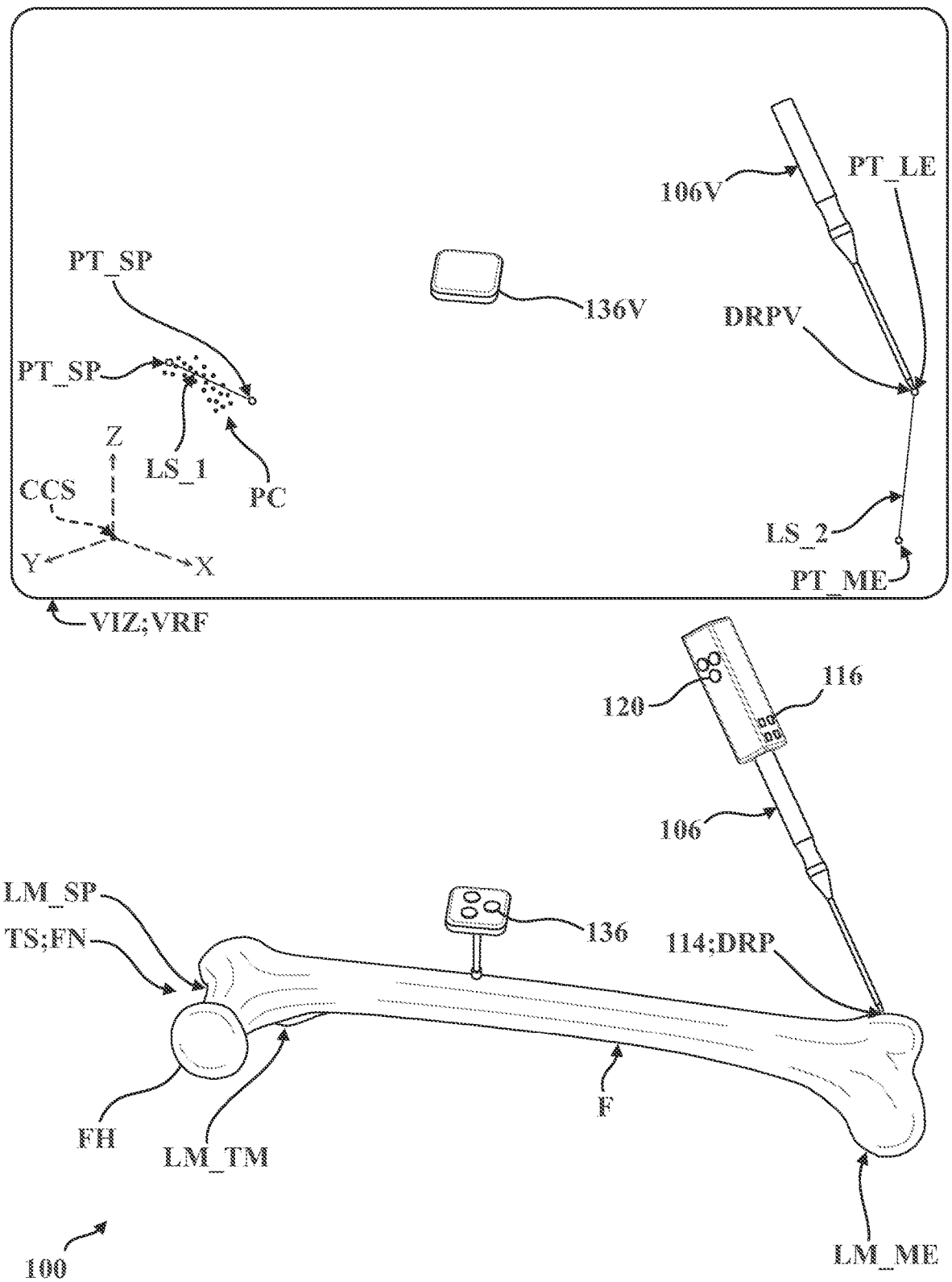
FIG. 32 is another partial perspective view of the digitization device, the patient tracker, the femur, and the visualization of the virtual reference frame of FIG. 31, shown with the pointer tip positioned at the lateral epicondyle landmark of the femur to digitize and establish a point at the lateral epicondyle landmark, shown with the corresponding point rendered in the visualization, and further shown with a line segment rendered within the visualization extending between the points established at the medial epicondyle landmark and at the lateral epicondyle landmark.
Figure 33:
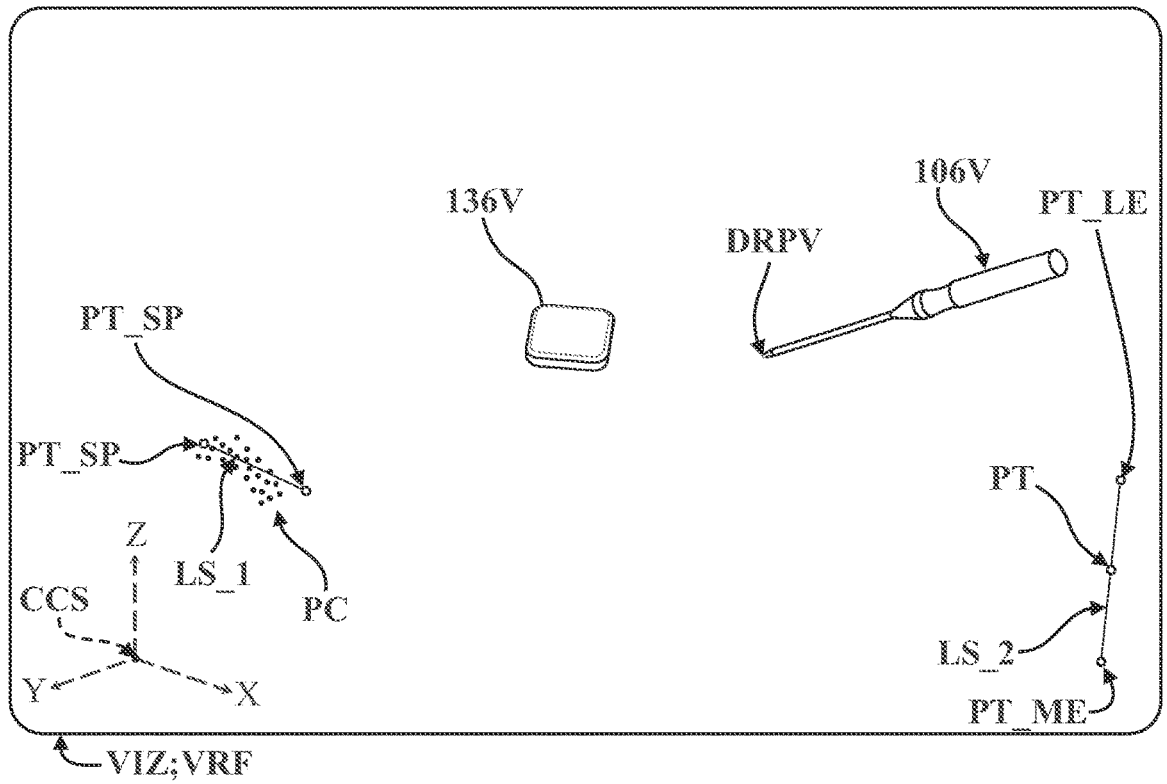
FIG. 33 is another partial perspective view of the digitization device, the patient tracker, the femur, and the visualization of the virtual reference frame of FIG. 32, shown with a calculated point rendered within the visualization arranged along the line segment equidistantly between the points established at the medial epicondyle landmark and at the lateral epicondyle landmark.
Figure 33:
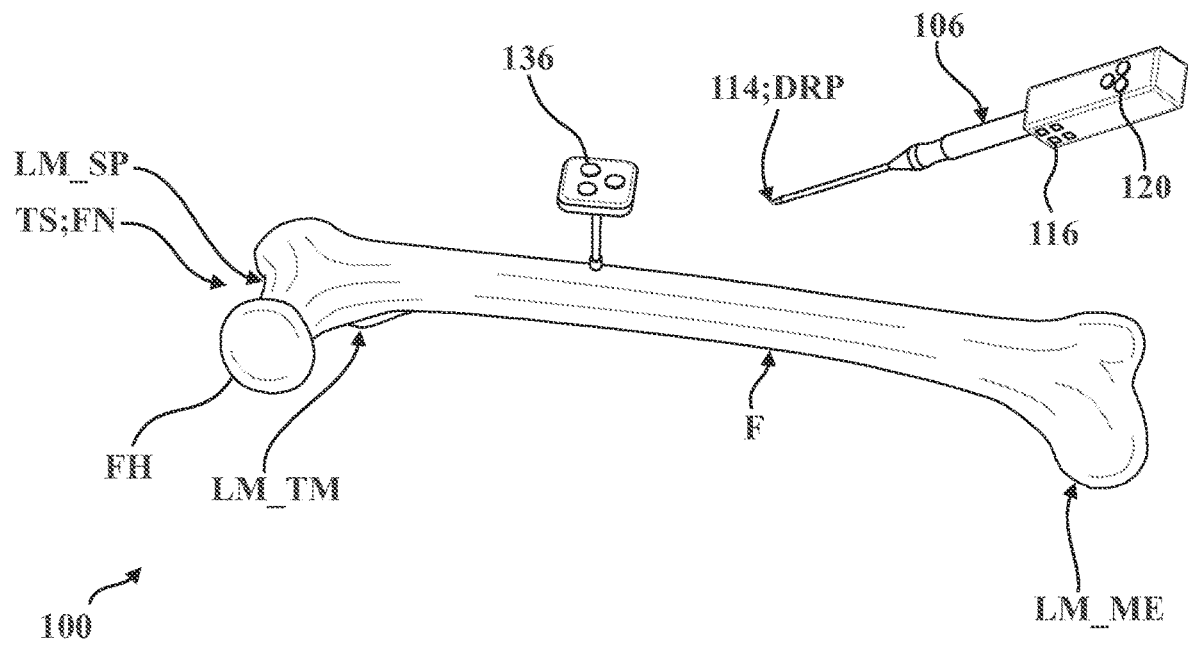

Continuing from FIG. 32 to FIG. 33, the visualization VIZ depicts a point PT arranged along the second line segment LS_2 midway between the medial epicondyle point PT_ME and the lateral epicondyle point PT_LE.

Figure 34:
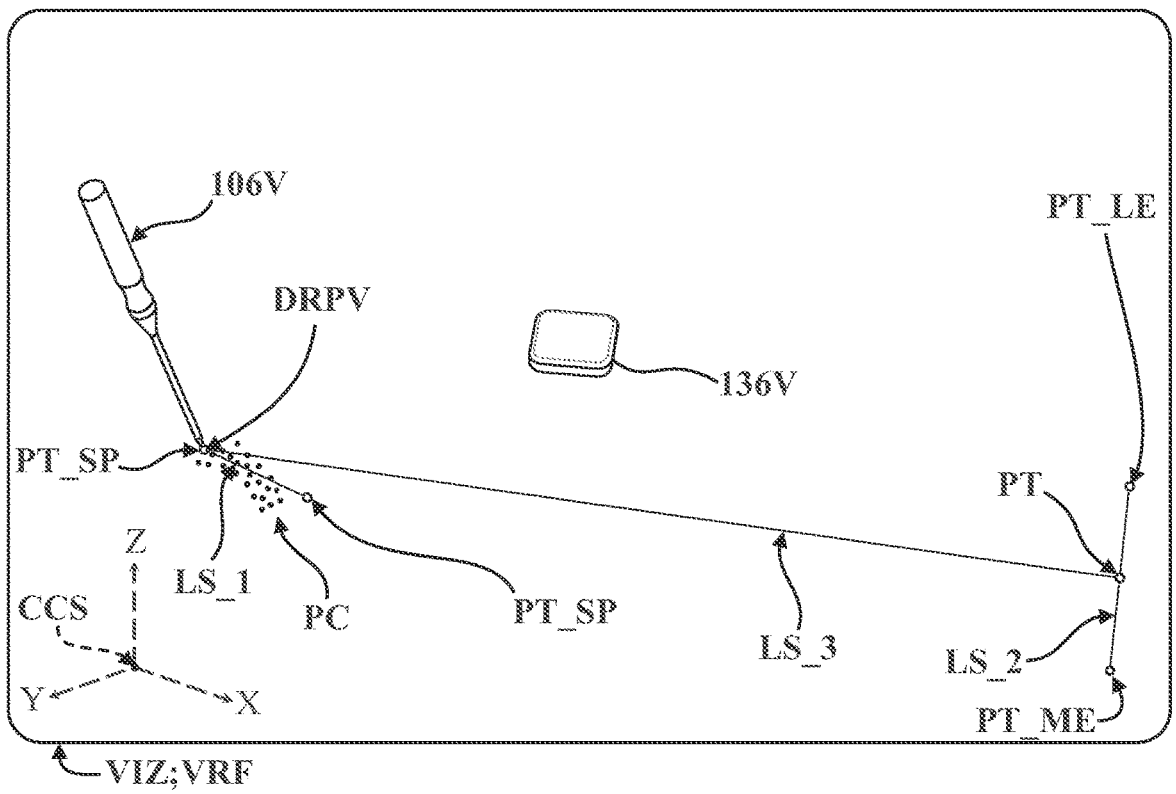
FIG. 34 is another partial perspective view of the digitization device, the patient tracker, the femur, and the visualization of the virtual reference frame of FIG. 33, shown with another line segment rendered within the visualization extending between the calculated point and the point established at the saddle point landmark.
Figure 34:
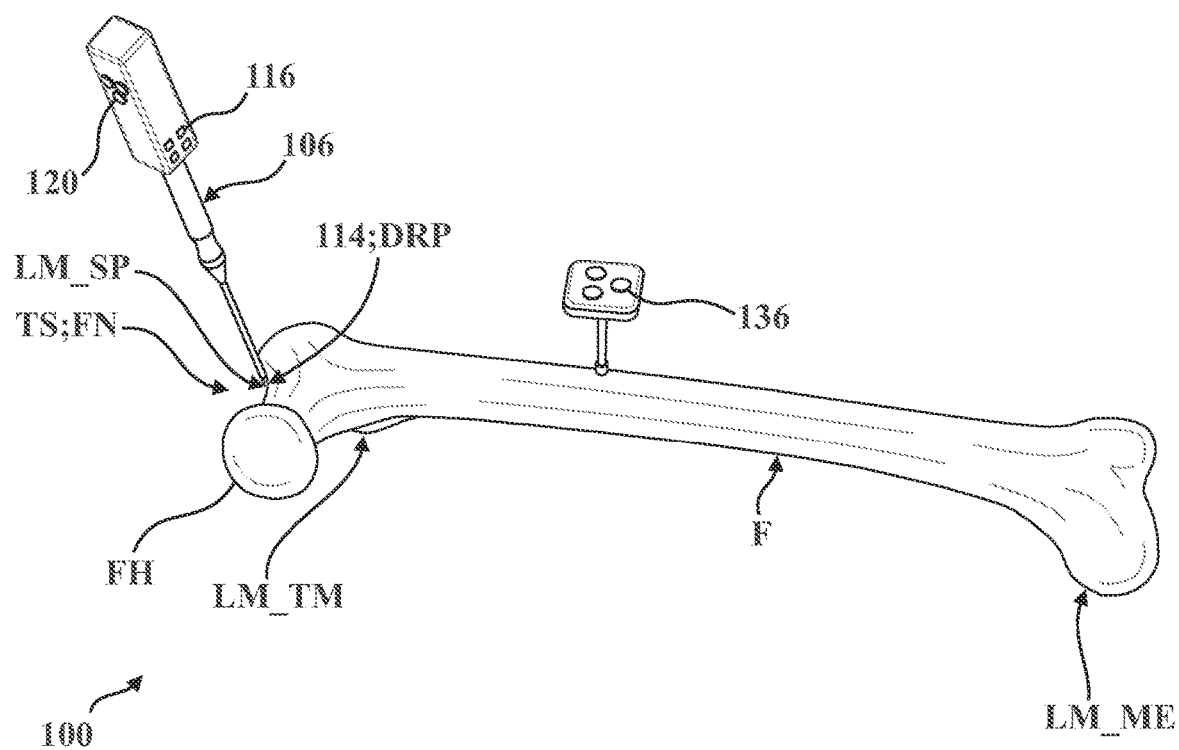

Continuing from FIG. 33 to FIG. 34, the visualization VIZ depicts a line segment (hereinafter, "third line segment LS_3") arranged extending between the point PT and the saddle point PT_SP. Contextually, the third line segment LS_3 is the anatomical axis of the femur F.

Continuing from FIG. 34 to FIG. 35, the visualization VIZ depicts an octagonal plane (hereinafter, "first plane PN_1") fixed to the virtual digitization device 106V in the parallel option 250 (as described above in connection with FIG. 24C) so as to enable the surgeon to arrange the first plane PN_1 within the virtual reference frame VRF by moving the digitization device 106 relative to the target site TS. In FIG. 34 (and also in FIGS. 35-40A and 41-42), the object index OI of the first plane PN_1 is not illustrated as a coordinate system with a normal vector as previously described and illustrated; rather, the object index OI is represented by the intersection of two dash-dot-dash lines arranged perpendicular to each other and extending between corners of the octagonal first plane PN_1 for clarity and to help illustrate movement and adjustment of the first plane PN_1 (e.g., as may be demonstrated by successively viewing FIGS. 35-40A).

Figure 35:
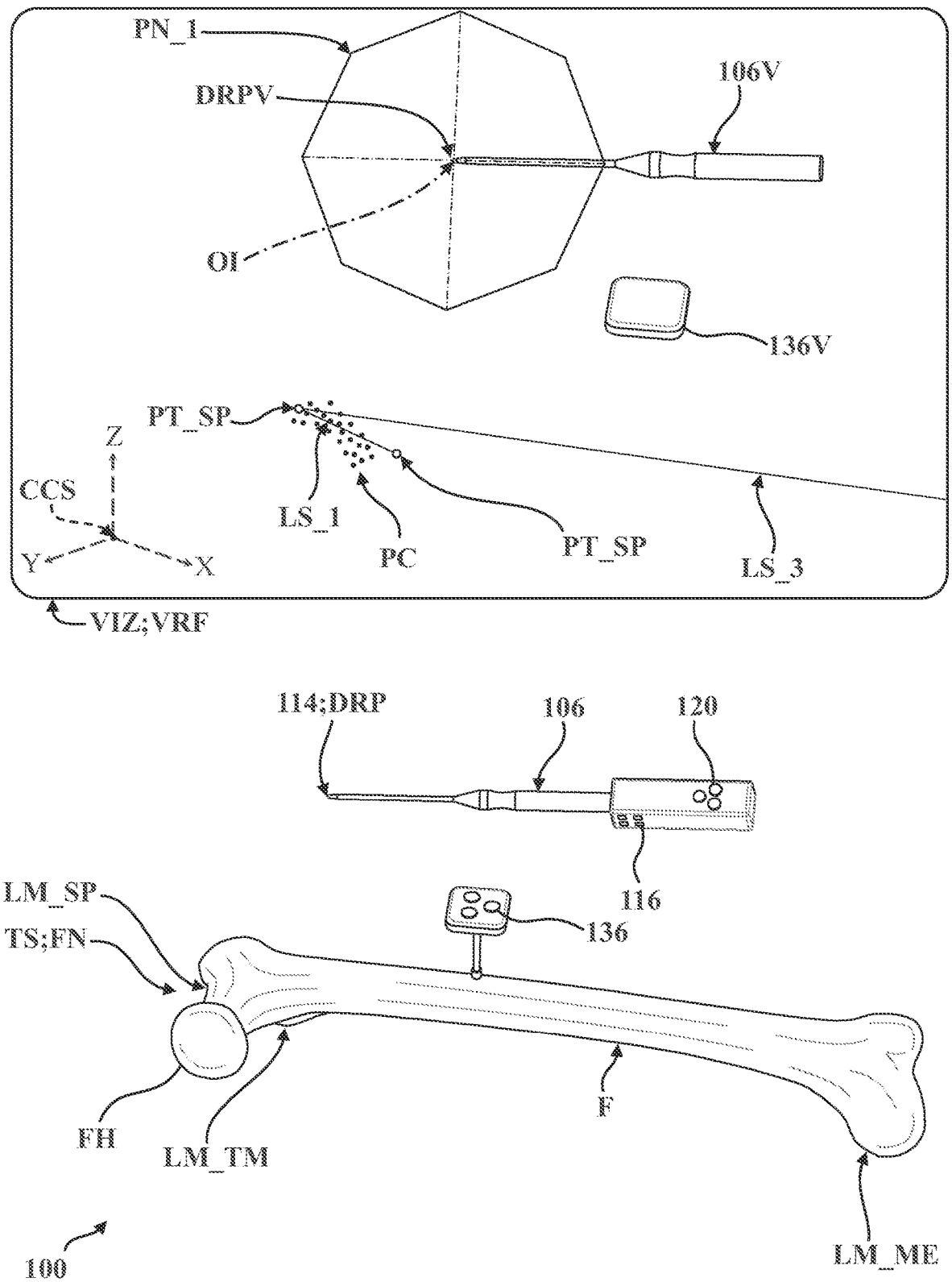
FIG. 35 is another partial perspective view of the digitization device, the patient tracker, the femur, and an enlarged view of the visualization of the virtual reference frame of FIG. 34, shown with an octagonal plane fixed to the pointer tip of the virtual representation of the digitization device rendered within the visualization and arranged in a parallel fashion relative to the virtual representation of the digitization device.
Figure 36:
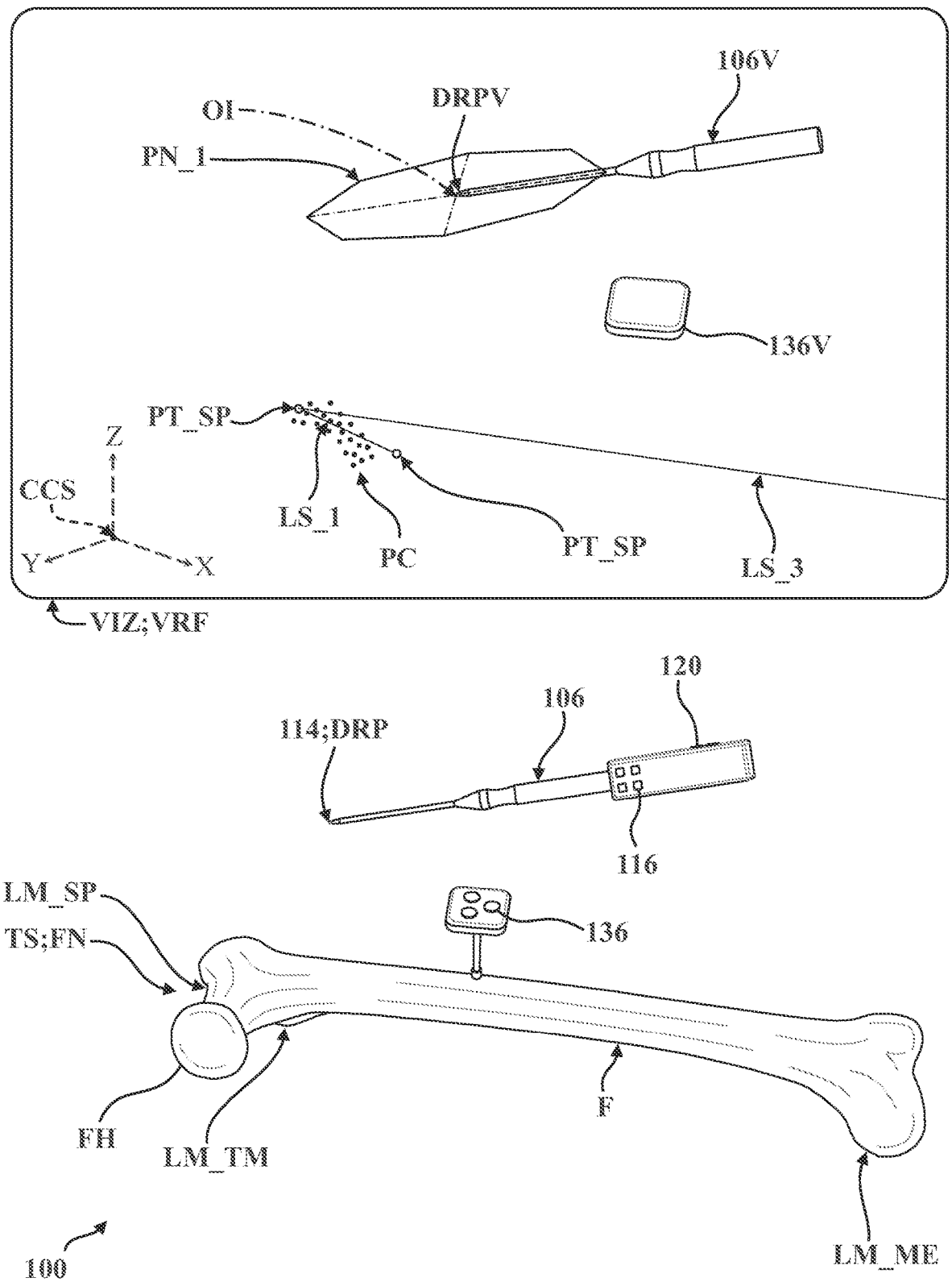
FIG. 36 is another partial perspective view of the digitization device, the patient tracker, the femur, and the visualization of the virtual reference frame of FIG. 35, shown with digitization device having been moved relative to the femur and with the visualization depicting corresponding movement of the octagonal plane fixed to the pointer tip of the virtual representation of the digitization device.

Continuing from FIG. 35 to FIG. 36, the visualization VIZ has been enlarged (e.g., by using the adjust view option 234 described above to zoom and pan), and depicts the first plane PN_1 still fixed to the virtual digitization device 106V but moved to a different pose based on corresponding movement of the digitization device 106 relative to the target site TS (compare FIG. 36 with FIG. 35).

Figure 37:
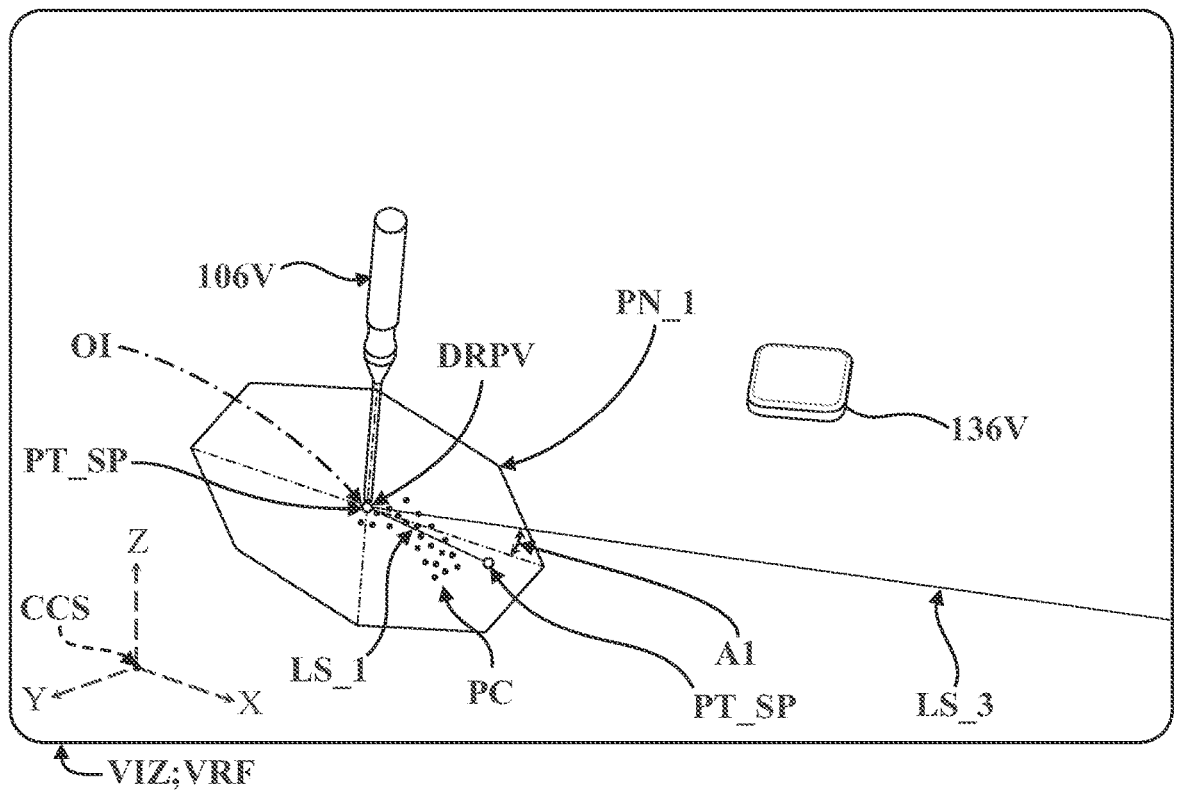
FIG. 37 is another partial perspective view of the digitization device, the patient tracker, the femur, and the visualization of the virtual reference frame of FIG. 36, shown with the visualization depicting the octagonal plane orientated concurrently with the virtual representation of the digitization device and positioned fixed to the point established at the saddle point landmark of the femur, the octagonal plane shown orientated at an angle relative to the line segment rendered within the visualization extending between the calculated point and the point established at the saddle point landmark.
Figure 37:
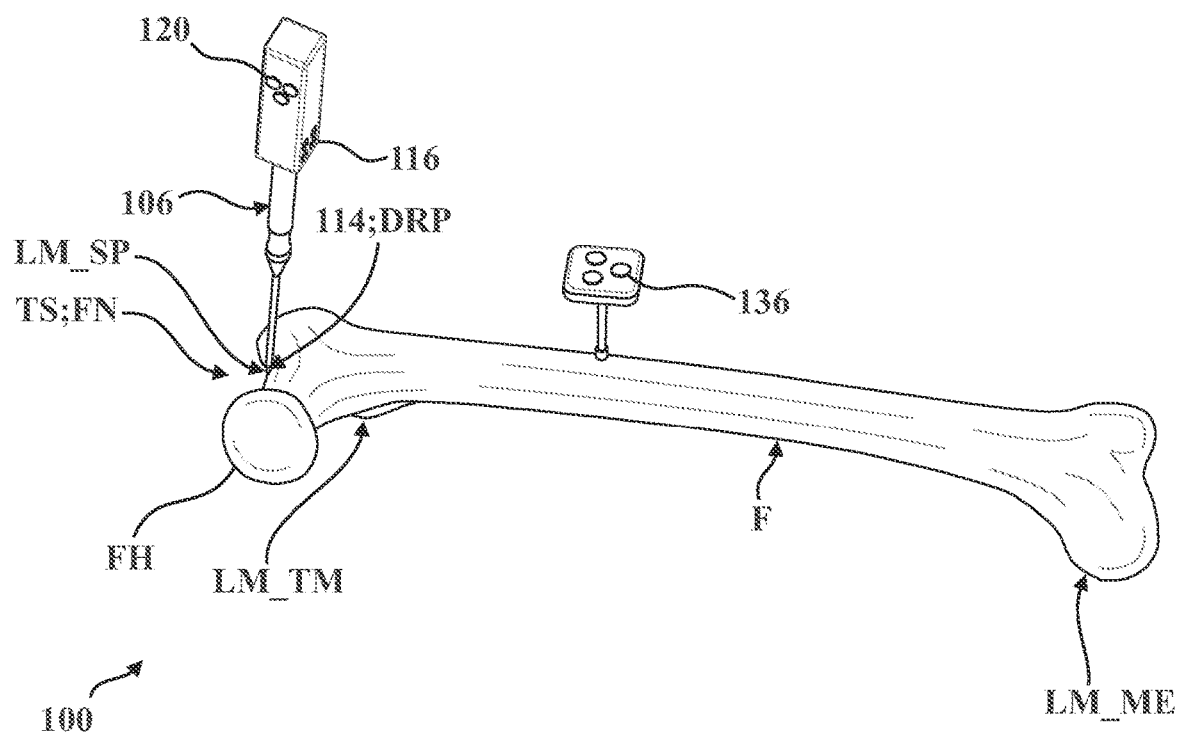

Continuing from FIG. 36 to FIG. 37, the visualization VIZ depicts the first plane PN_1 still (partially) fixed to the virtual digitization device 106V but is moved to yet another different pose based on corresponding movement of the digitization device 106 relative to the target site TS (compare FIG. 37 with FIG. 36). Here in FIG. 37, the object index OI of the first plane PN_1 is also fixed to and can rotate about the saddle point PT_SP based on movement of the digitization device 106 (as described above in connection with FIGS. 25A-25B). This allows the surgeon to visualize and thereby orientate the first plane PN_1 relative to the target site TS using the digitization device 106, and the surgeon can unfix the first plane PN_1 from the virtual digitization device 106V (e.g., by actuating the pointer control input 116) and subsequently the GUI 172 of the CAD program 102 to fully-define the first plane PN_1. As shown in FIG. 37, the first plane PN1 is shown orientated at a first angle A1 with respect to the third line segment LS_3 (the anatomical axis of the femur F), such as may be determined with the angle measurements 200 functionality of the CAD program 102 described previously.

Continuing from FIG. 37 to FIG. 38, the visualization VIZ depicts the first plane PN_1 with its object index OI still fixed to the saddle point PT_SP, but having been subsequently orientated to a second angle A2 (e.g., a larger angle; compare FIG. 38 with FIG. 37) with respect to the third line segment LS_3 (the anatomical axis of the femur F). This change in arrangement may likewise have been carried out using the angle measurements 200 functionality of the CAD program 102 described previously.

Figure 38:
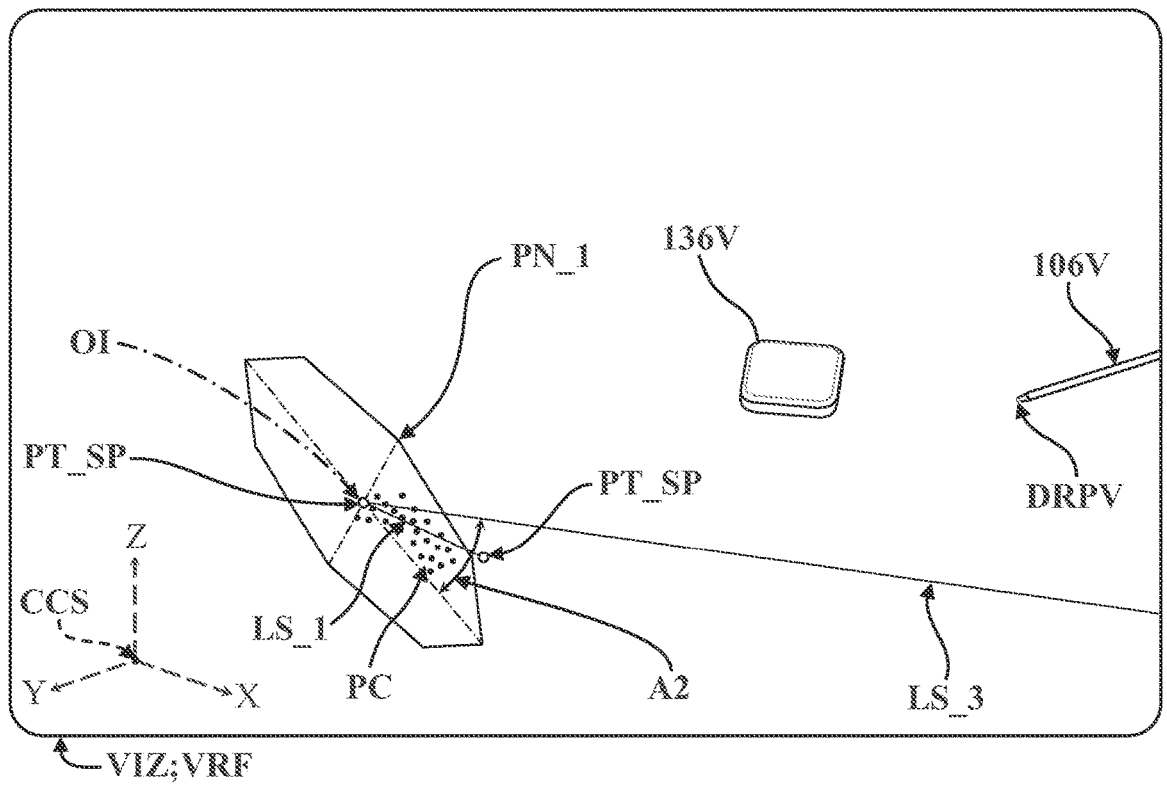
FIG. 38 is another partial perspective view of the digitization device, the patient tracker, the femur, and the visualization of the virtual reference frame of FIG. 37, shown with the visualization depicting the octagonal plane having been arranged at a larger angle relative to the line segment while remaining fixed to the point established at the saddle point landmark of the femur.
Figure 38:
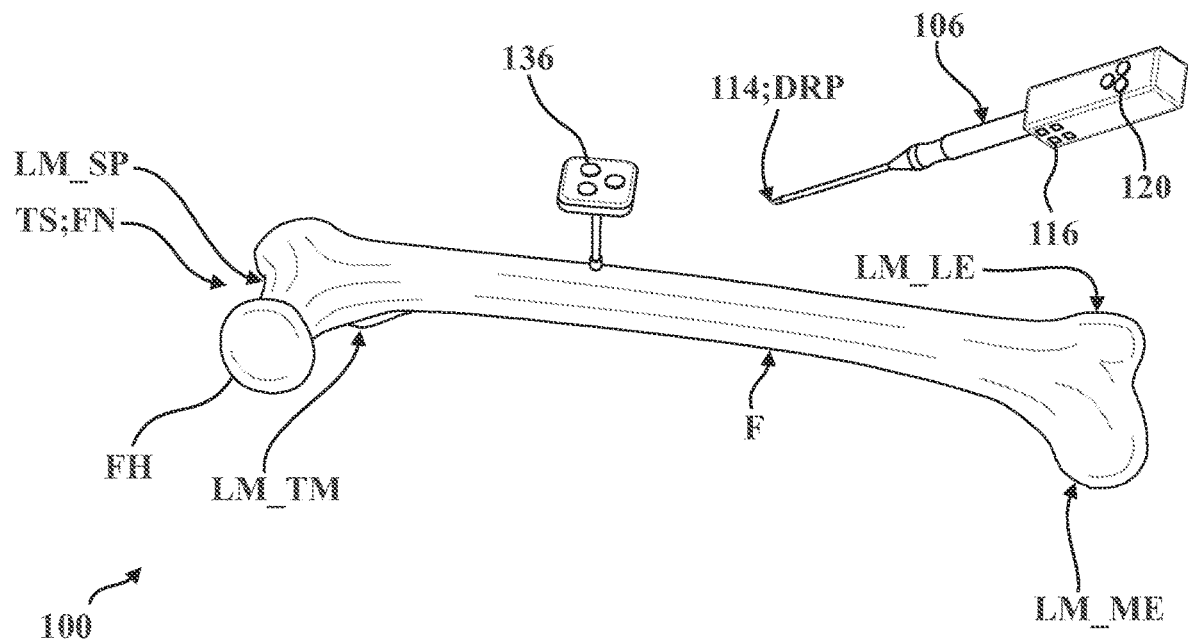
Figure 39:
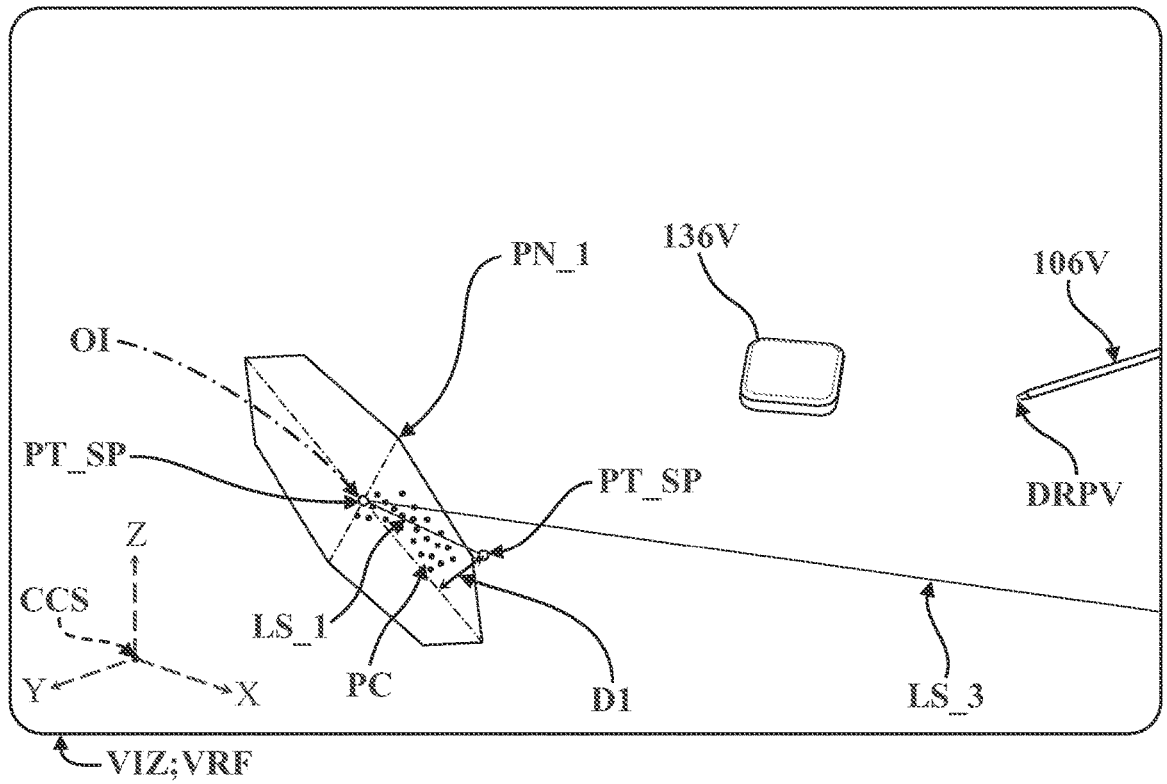
FIG. 39 is another partial perspective view of the digitization device, the patient tracker, the femur, and the visualization of the virtual reference frame of FIG. 38, shown with the visualization depicting the octagonal plane in the same arrangement at the larger angle, and further showing a measured distance between the octagonal plane and the point established at the trochanter minor landmark of the femur.
Figure 39:
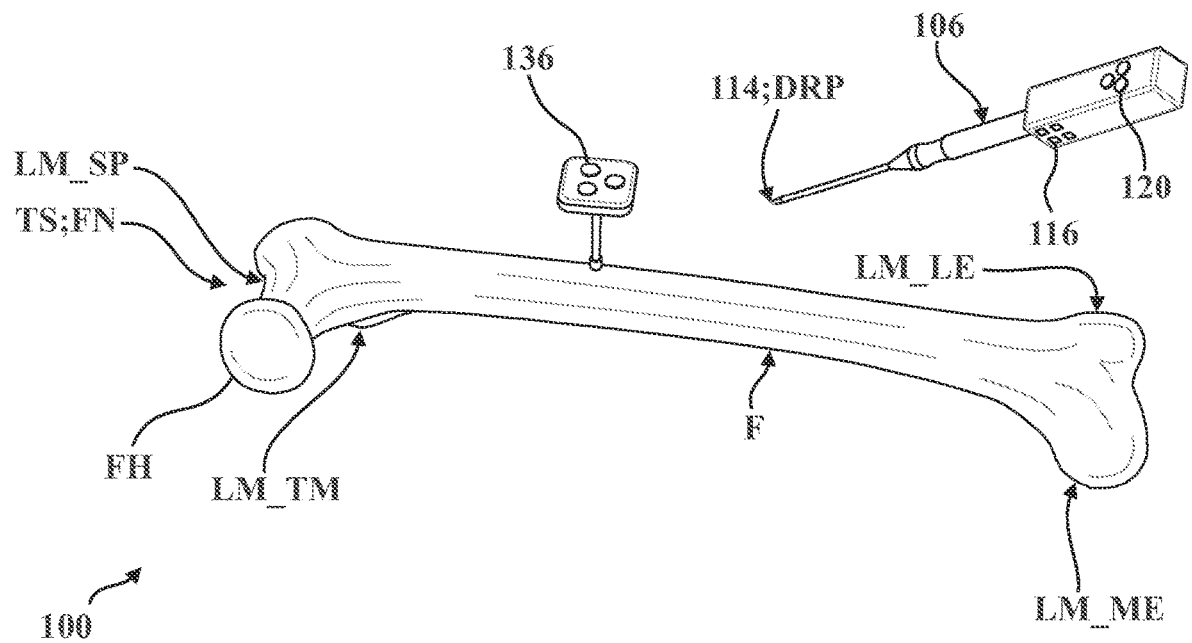

Continuing from FIG. 38 to FIG. 39, the visualization VIZ depicts the first plane PN_1 in the same pose, but is shown at at a first distance D1 measured with respect to the trochanter minor point PT_TM. Here, the first distance D1 may have been determined with the distance measurements 202 functionality of the CAD program 102 described previously.

Figure 40A:
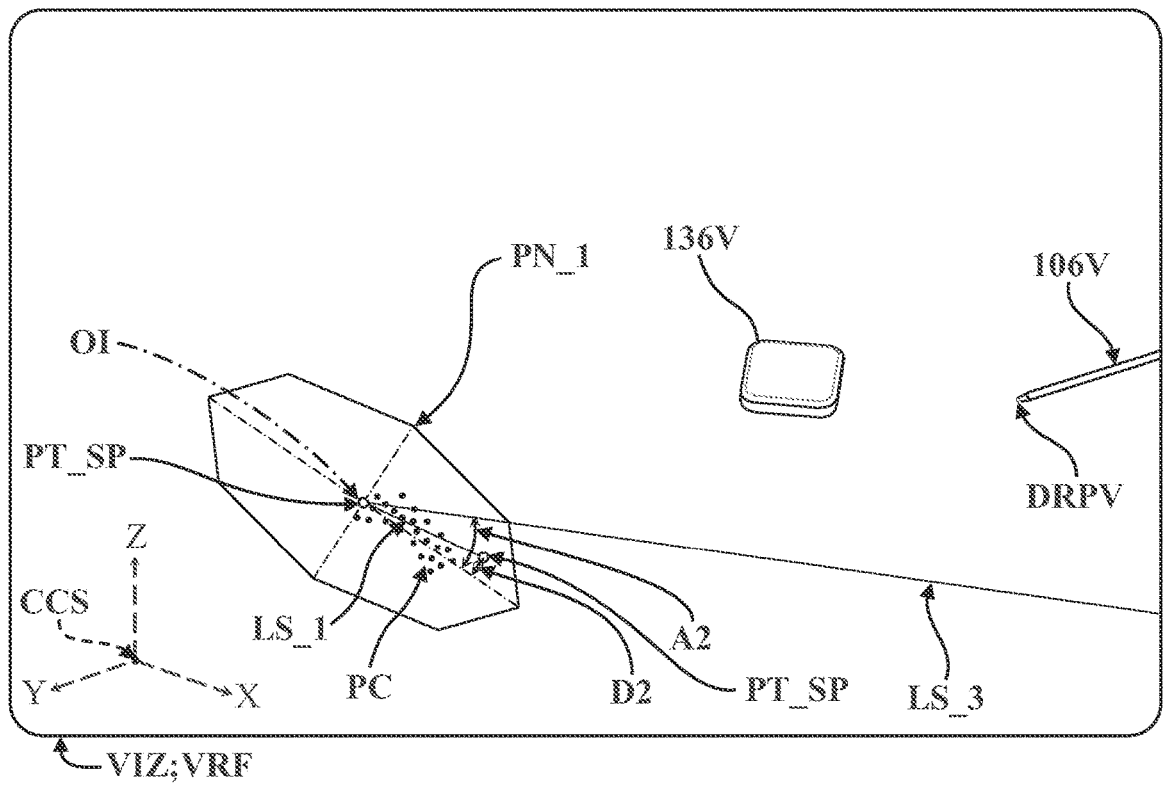
FIG. 40A is another partial perspective view of the digitization device, the patient tracker, the femur, and the visualization of the virtual reference frame of FIG. 39, shown with the visualization depicting the octagonal plane arranged so at to be at a smaller distance relative to the point established at the trochanter minor landmark of the femur while still at the larger angle relative to the line segment.
Figure 40A:
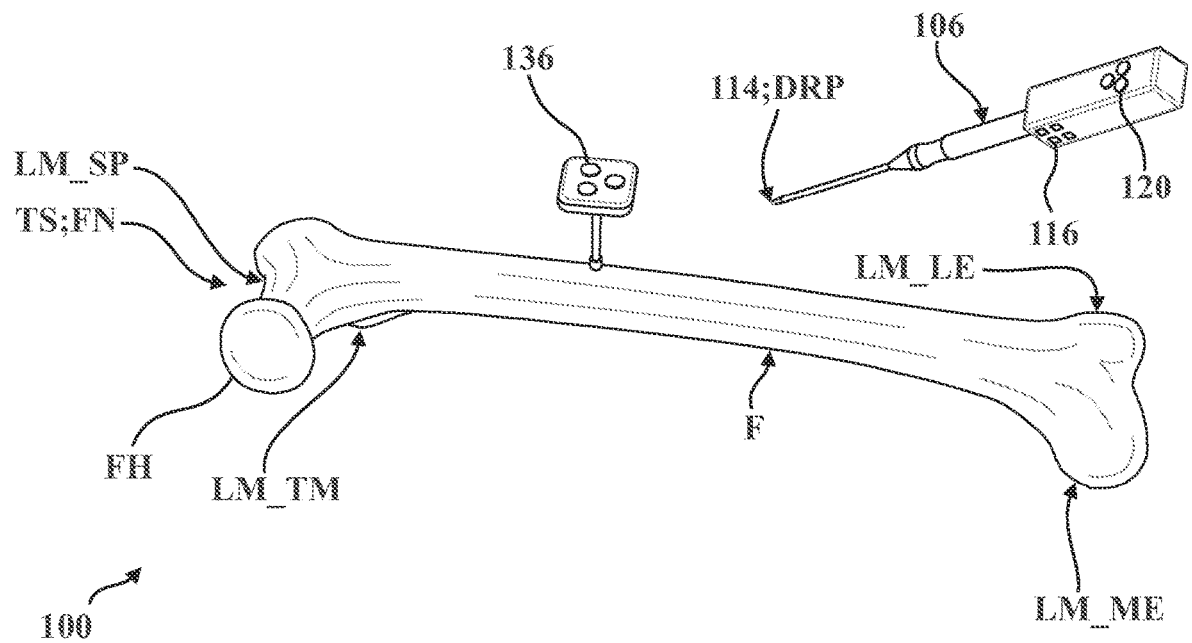

Continuing from FIG. 39 to FIG. 40A, the visualization depicts the first plane PN_1 in a different pose after having been moved to a second distance D2 (e.g., a smaller distance; compare FIG. 40A with FIG. 39) with respect to the trochanter minor point PT_TM. This change in arrangement may likewise have been carried out using the distance measurements 202 functionality of the CAD program 102 described previously. Furthermore, as is demonstrated in FIG. 40A, the second angle A2 is maintained with respect to the third line segment LS_3 (the anatomical axis of the femur F). Thus, FIG. 40A depicts the first plane PN_1 as fully-defined and arranged within the virtual reference frame VRF.

Figure 40B:
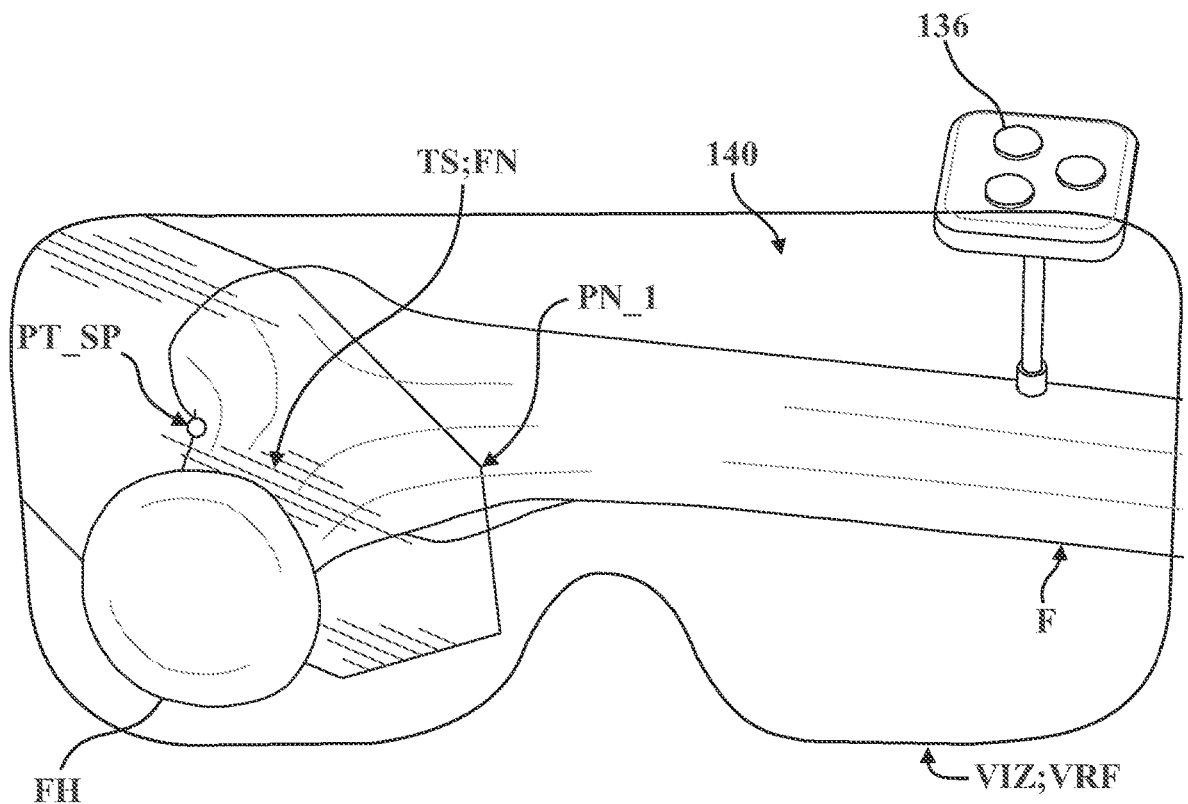
FIG. 40B is an enlarged partial perspective view of the patient tracker and the femur of Figure of FIG. 40A shown depicted as being viewed through the HMD unit of FIG. 18 to illustrate the octagonal plane and the point established at the saddle point landmark rendered overlaid onto the femur with augmented reality.

Continuing from FIG. 40A to FIG. 40B, a portion of the femur F is shown with the first patient tracker 136 attached thereto as viewed by the surgeon through the HMD unit 140 (as described above in connection with FIG. 19F). Here in FIG. 40B, because the HMD unit 140 is able to render the visualization VIZ based on the visualization data VZ generated using the tracked states SZ monitored with the navigation system 104, the surgeon is able to view the fully-defined first plane PN_1 rendered overlaid onto the femur F with augmented reality (or "mixed reality"). Further, the saddle point PT_SP of the visualization VIZ is also rendered overlaid onto the saddle point landmark LM_SP of the femur F.

Continuing now from FIG. 40A to FIG. 41, the visualization VIZ depicts the first plane PN_1 in the same pose, and also depicts a second octagonal plane (hereinafter, "second plane PN_2") arranged parallel to and spaced from the first plane PN_1 at a first cut distance C1. The first plane PN_1 and the second plane PN_2 here are configured as a compound type object 198 realized as an osteotomy plane OP (as described above in connection with FIG. 14). Here, the first cut distance C1 may have been determined with the distance measurements 202 functionality of the CAD program 102 described previously.

Figure 41:
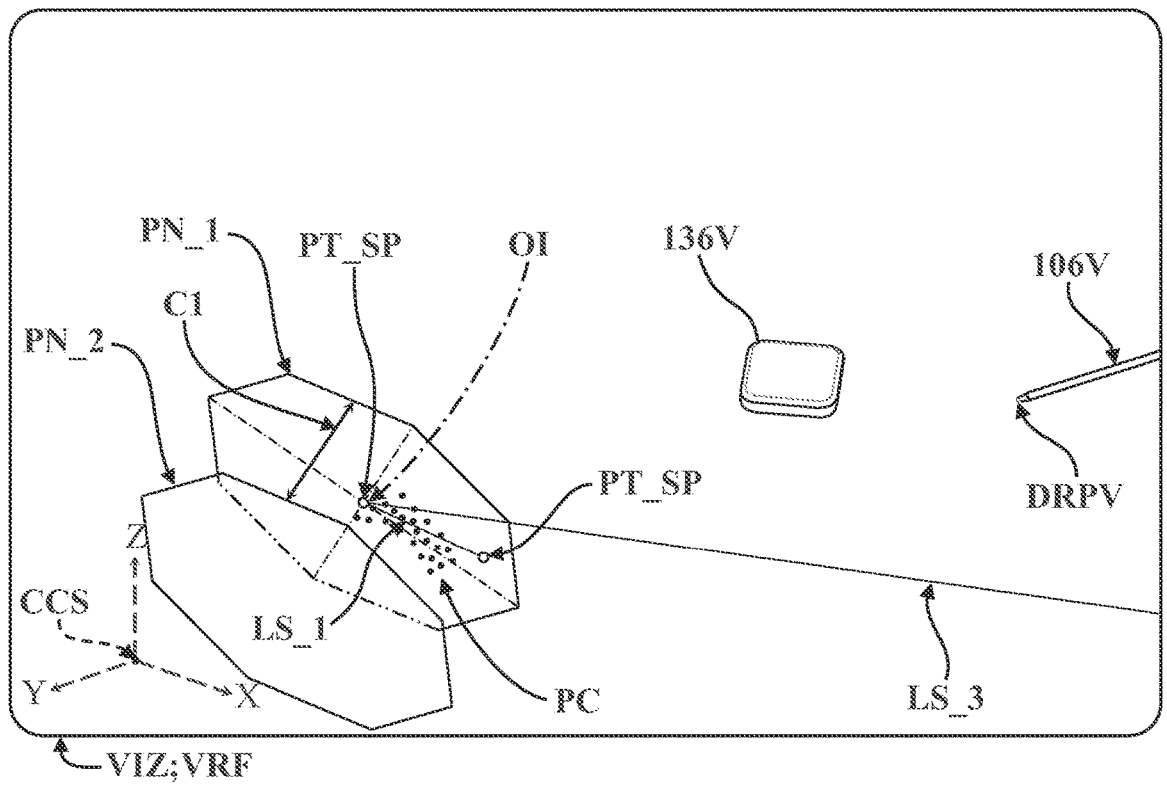
FIG. 41 is another partial perspective view of the digitization device, the patient tracker, the femur, and the visualization of the virtual reference frame of FIG. 40A, shown with the visualization depicting an osteotomy plane constructed with another, parallel octagonal plane spaced at a cut distance.
Figure 41:
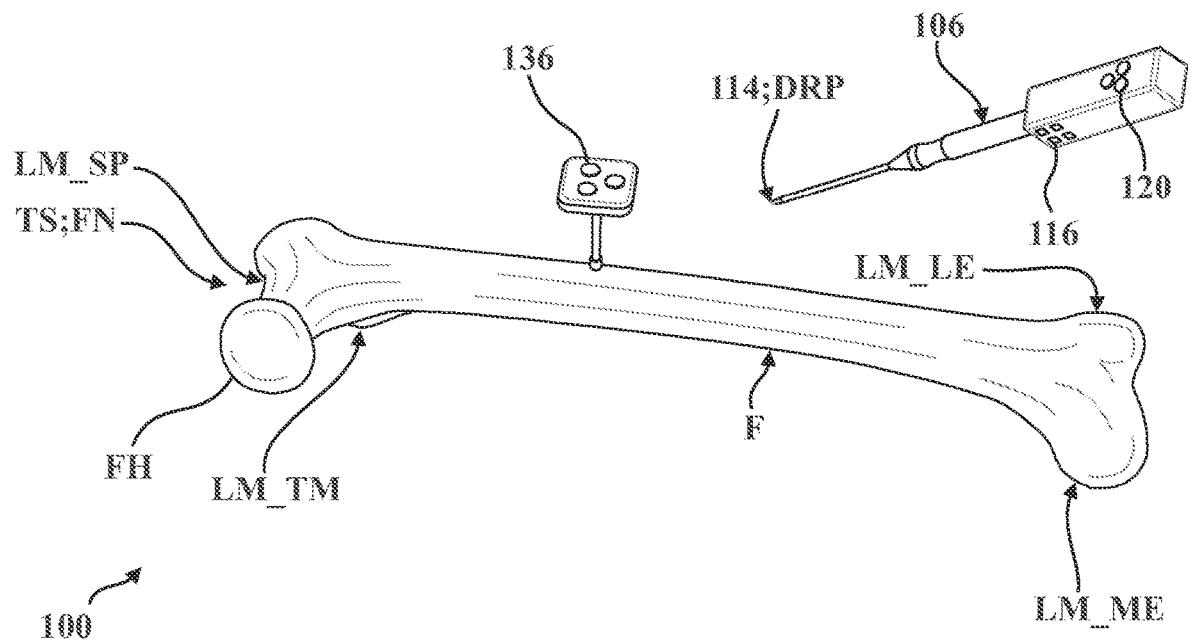
Figure 42:
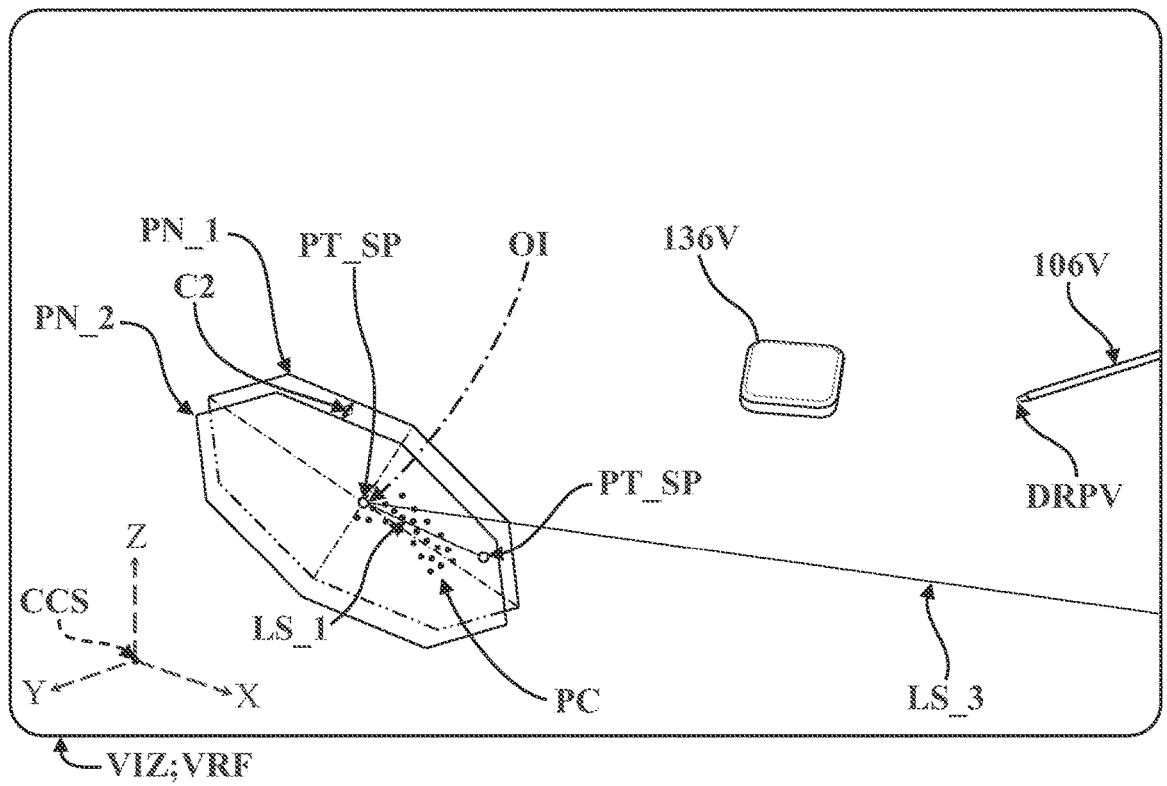
FIG. 42 is another partial perspective view of the digitization device, the patient tracker, the femur, and the visualization of the virtual reference frame of FIG. 41, shown with the visualization depicting the osteotomy plane adjusted to a smaller cut distance.
Figure 42:
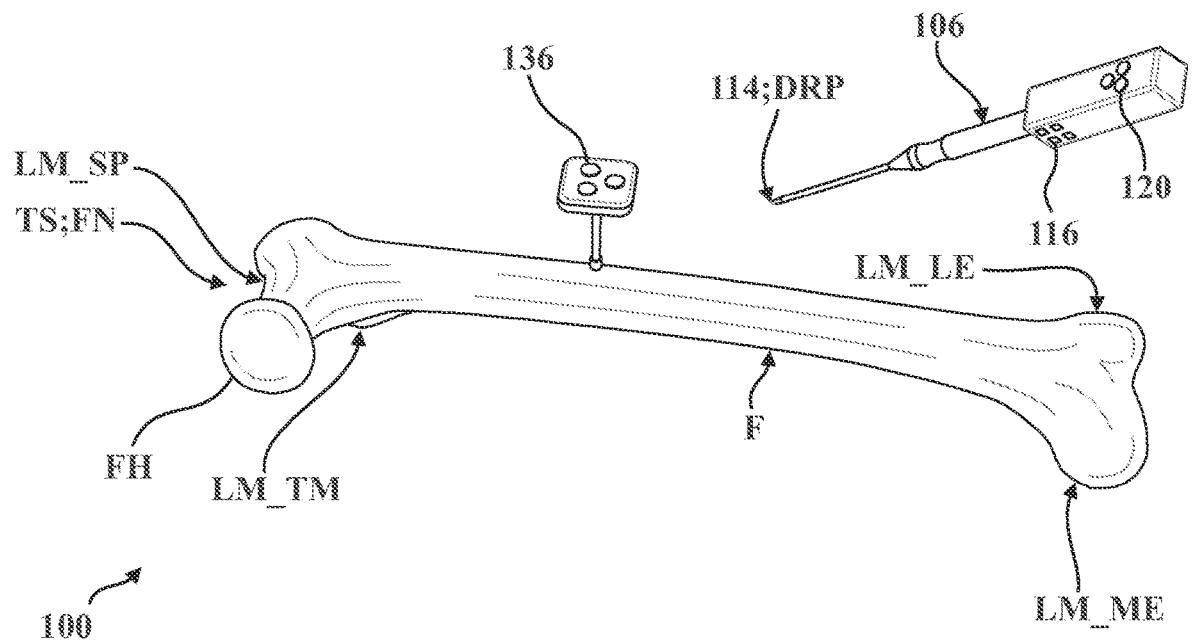

Continuing from FIG. 41 to FIG. 42, the visualization VIZ depicts the first plane PN_1 in the same pose, but depicts the second plane PN_2 in a different pose. Here, while still parallel to and generally aligned with the first plane PN_1, the second plane PN_2 has been moved relative to the first plane PN_1 to a second cut distance C2 (e.g. a smaller cut distance; compare FIG. 42 with FIG. 41). Here too, the second cut distance C2 may have been carried out using the distance measurements 202 functionality of the CAD program 102 described previously.

Figure 43:
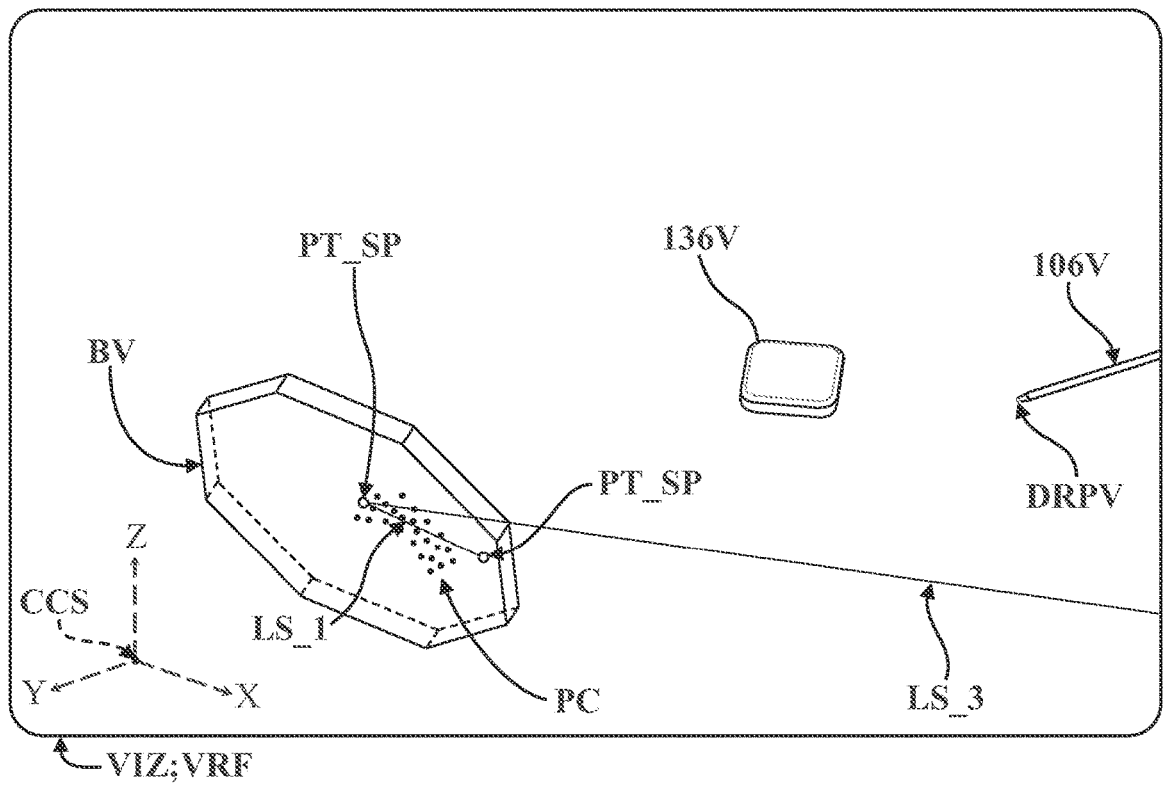
FIG. 43 is another partial perspective view of the digitization device, the patient tracker, the femur, and the visualization of the virtual reference frame of FIG. 42, shown with the visualization depicting a volume defined by the osteotomy plane.
Figure 43:
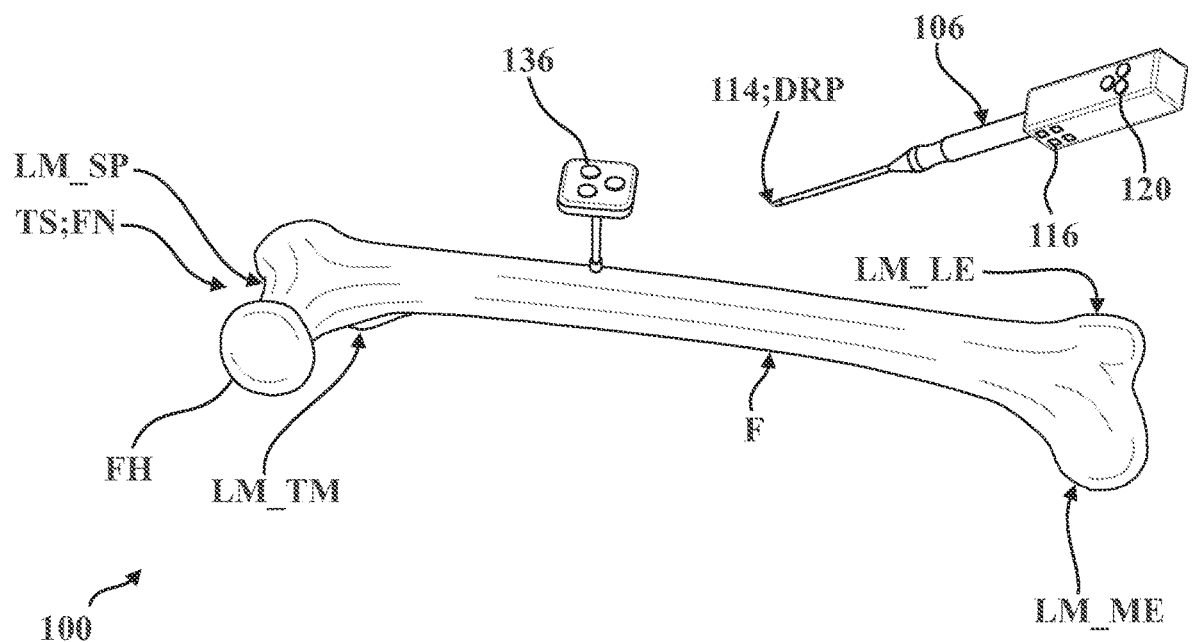

Continuing from FIG. 42 to FIG. 43, the visualization VIZ depicts a bounding volume BV generated, such as via the algorithms module 174 described above, between the first and second planes PN_1, PN_2. Here, this bounding volume BV may be used to help clip a surface generated from the point cloud PC (e.g., a triangle mesh TM), and/or may be used to calculate a milling volume MV, define one or more virtual boundaries 216, and/or generate tool control data CZ in some embodiments.

Figure 44:
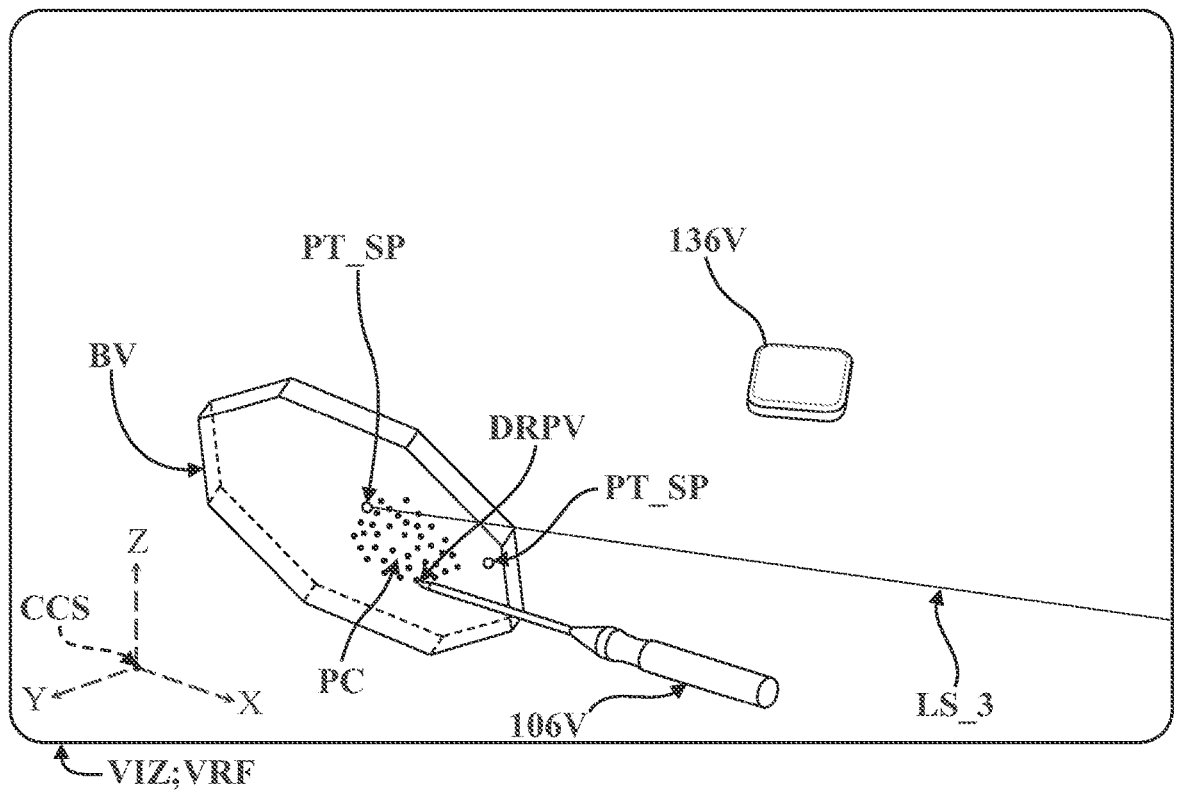
FIG. 44 is another partial perspective view of the digitization device, the patient tracker, the femur, and the visualization of the virtual reference frame of FIG. 43, shown with the pointer tip of the digitization device positioned along the femoral neck of the femur to digitize and establish additional points for in the point cloud about the femoral neck, and shown with the corresponding additional points of the point cloud rendered in the visualization.
Figure 44:
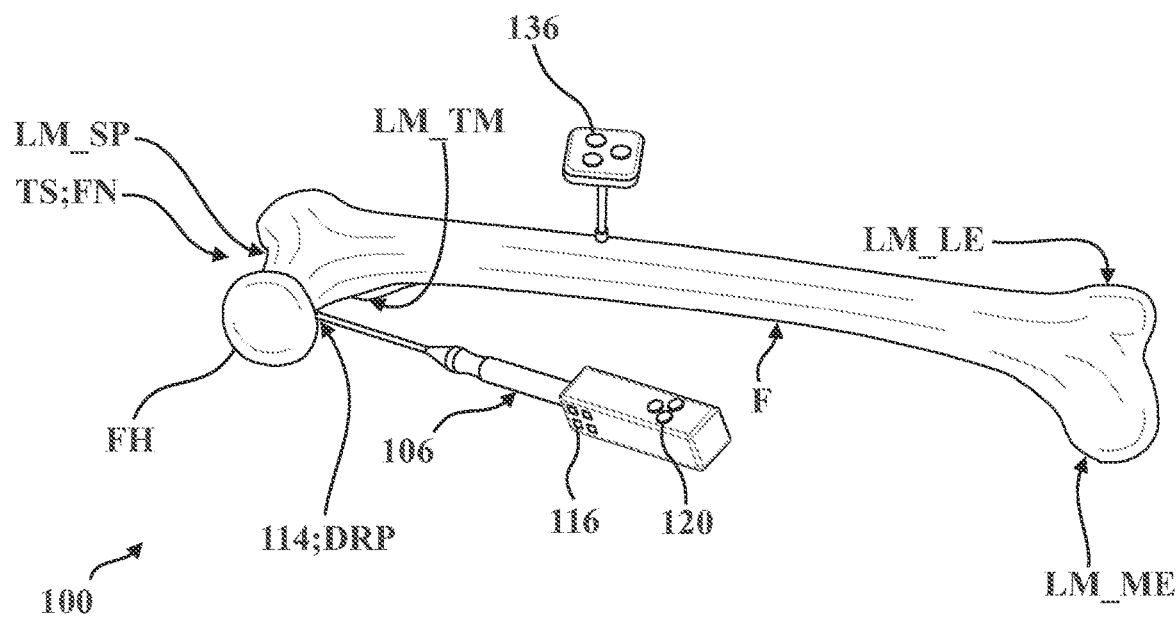

Continuing from FIG. 43 to FIG. 44, the pointer tip 114 of the digitization device 106 is shown positioned differently about the femoral neck FN (compare FIG. 44 with FIG. 28) to demonstrate arranging additional points PT which are to be merged with the point cloud PC within the virtual reference frame VRF. The resulting merged point cloud PC is shown rendered in the visualization VIZ. Here, arranging additional points PT may be bounded by the bounding volume BV defined by the first and second planes PN_1, PN_2 in order to form a more accurate triangle mesh TM used to generate a milling volume MV. Put differently, points PT established where the pointer tip 114 is positioned outside of the bounding volume BV may be ignored or otherwise not registered by the CAD program 102.

Figure 45:
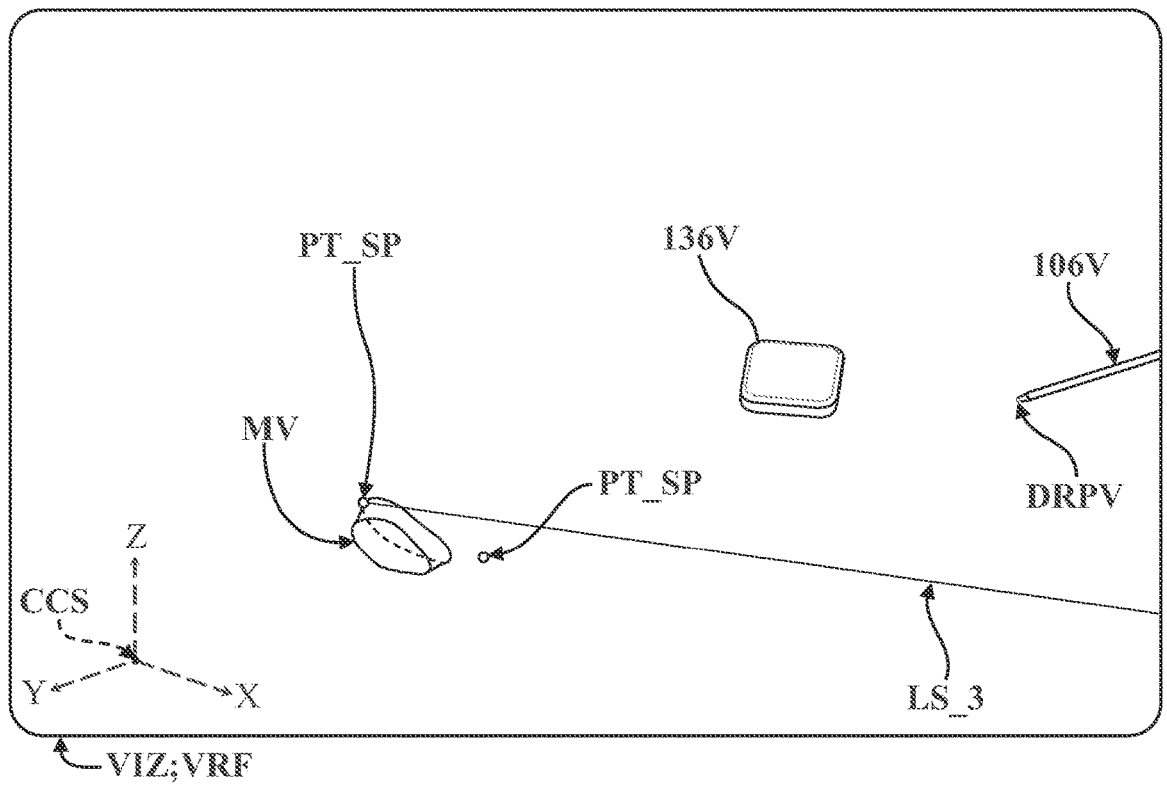
FIG. 45 is another partial perspective view of the digitization device, the patient tracker, the femur, and the visualization of the virtual reference frame of FIG. 44, shown with the visualization depicting a milling volume calculated by the CAD program from the point cloud and the constructed osteotomy plane.
Figure 45:
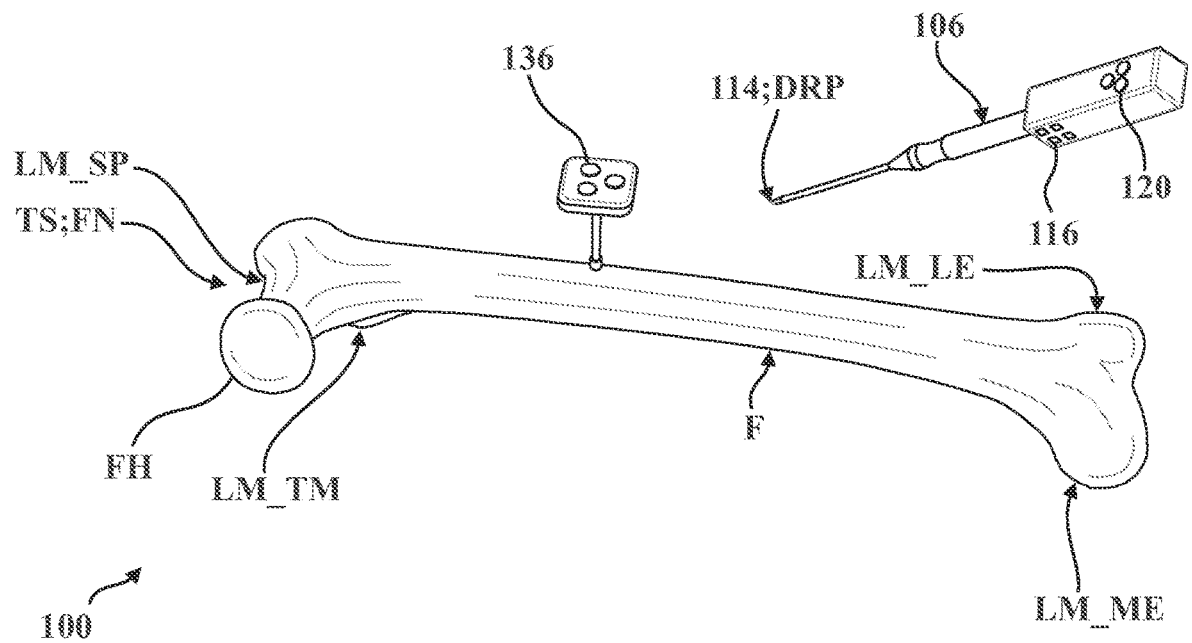

Continuing from FIG. 44 to FIG. 45, the visualization VIZ shows a rendered milling volume MV generated using the point cloud PC and the bounding volume BV illustrated in FIG. 44. Here, the milling volume MV may be generated by the CAD program 102 using various aspects of the algorithm module 174 described above (e.g., calculating a triangle mesh TM with the point cloud PC and clipping the triangle mesh TM with the first and second planes PN_1. PN_2).

Figure 46A:
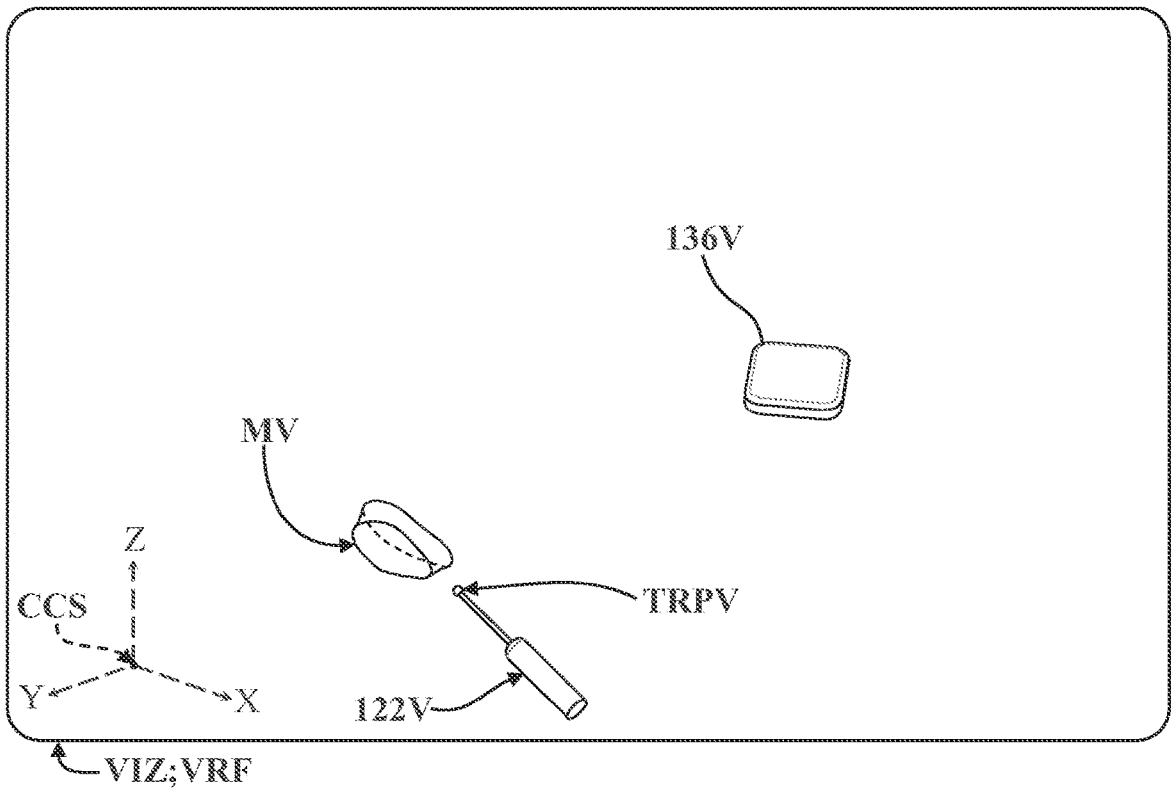
FIG. 46A is another partial perspective view of the patient tracker, the femur, and the visualization of the virtual reference frame of FIG. 45 depicted with the surgical tool of FIG. 18 positioned adjacent to the femoral neck, and shown with a virtual representation of the surgical tool rendered within the visualization based on tracked states of the surgical tool, and further shown with the milling volume depicted in the visualization established as a virtual boundary for the surgical tool.
Figure 46A:
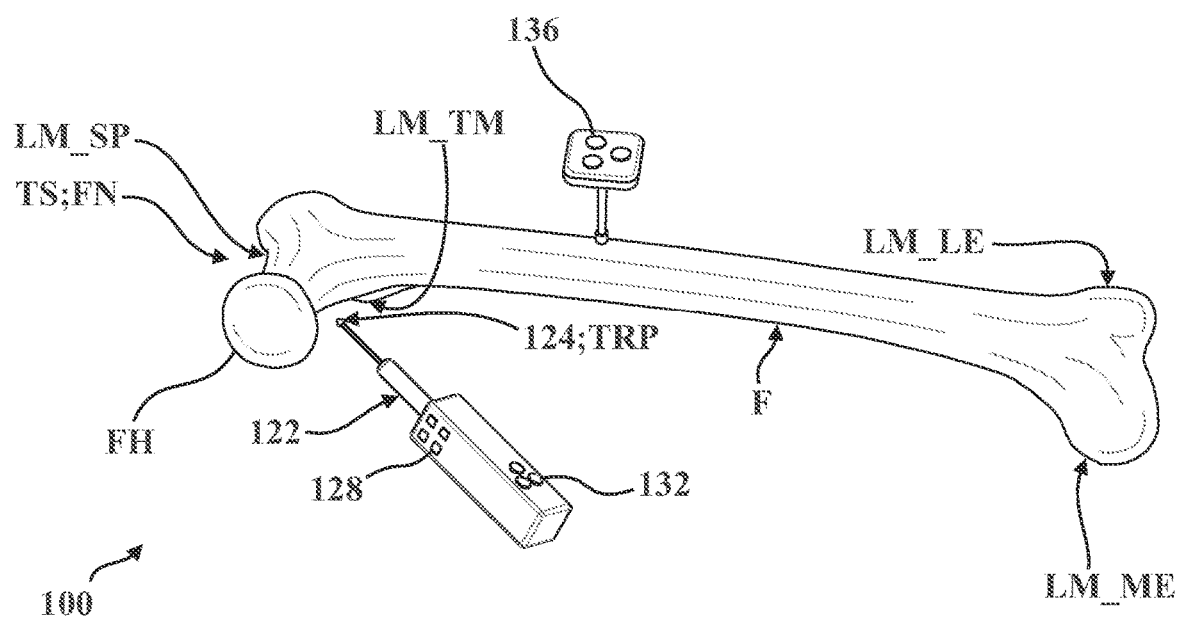

Continuing from FIG. 45 to FIG. 46A, the surgical tool 122 is shown spaced from the target site TS such that the energy applicator 124 is out of contact with the patient's anatomy (e.g., positioned in air). The virtual surgical tool 122V is rendered in the visualization VIZ adjacent to the milling volume MV. FIG. 46A generally depicts the target site TS just before the femoral neck FN is to be resected during execution of the femoral neck osteotomy.

Figure 46B:
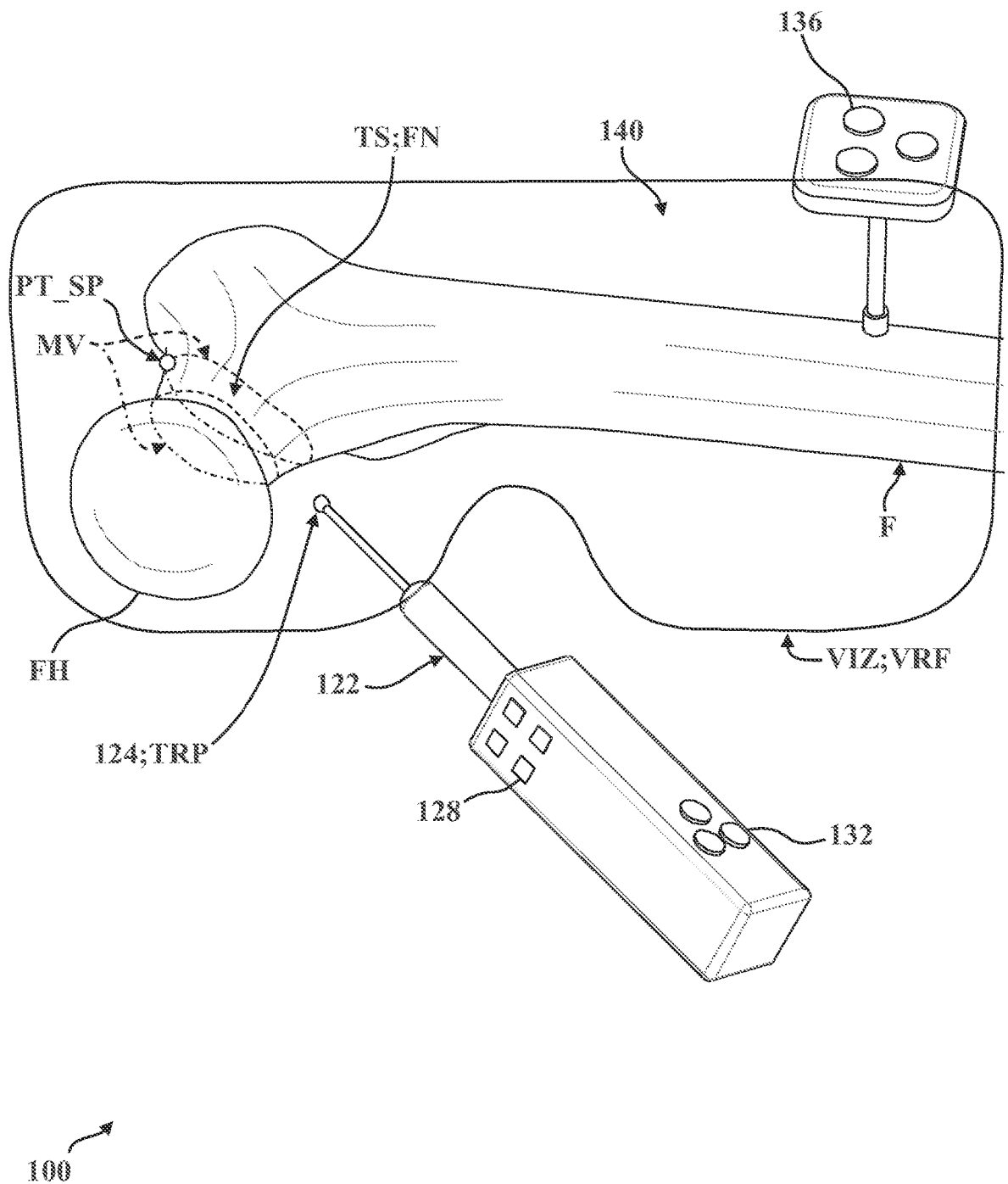
FIG. 46B is an enlarged partial perspective view of the surgical tool, the patient tracker, and the femur of Figure of FIG. 46A shown depicted as being viewed through the HMD unit of FIG. 18 to illustrate the milling volume and the point established at the saddle point landmark rendered overlaid onto the femur with augmented reality.

Continuing from FIG. 46A to FIG. 46B, similar to FIG. 40B described above, a portion of the femur F is shown with the first patient tracker 136 attached thereto as viewed by the surgeon through the HMD unit 140. Here in FIG. 46B, because the HMD unit 140 is able to render the visualization VIZ based on the visualization data VZ generated using the tracked states SZ monitored with the navigation system 104, the surgeon is able to view the milling volume MV rendered overlaid onto the femur F with augmented reality (or "mixed reality"). Further, the saddle point PT_SP of the visualization VIZ is also rendered overlaid onto the saddle point landmark LM_SP of the femur F.

Figure 47:
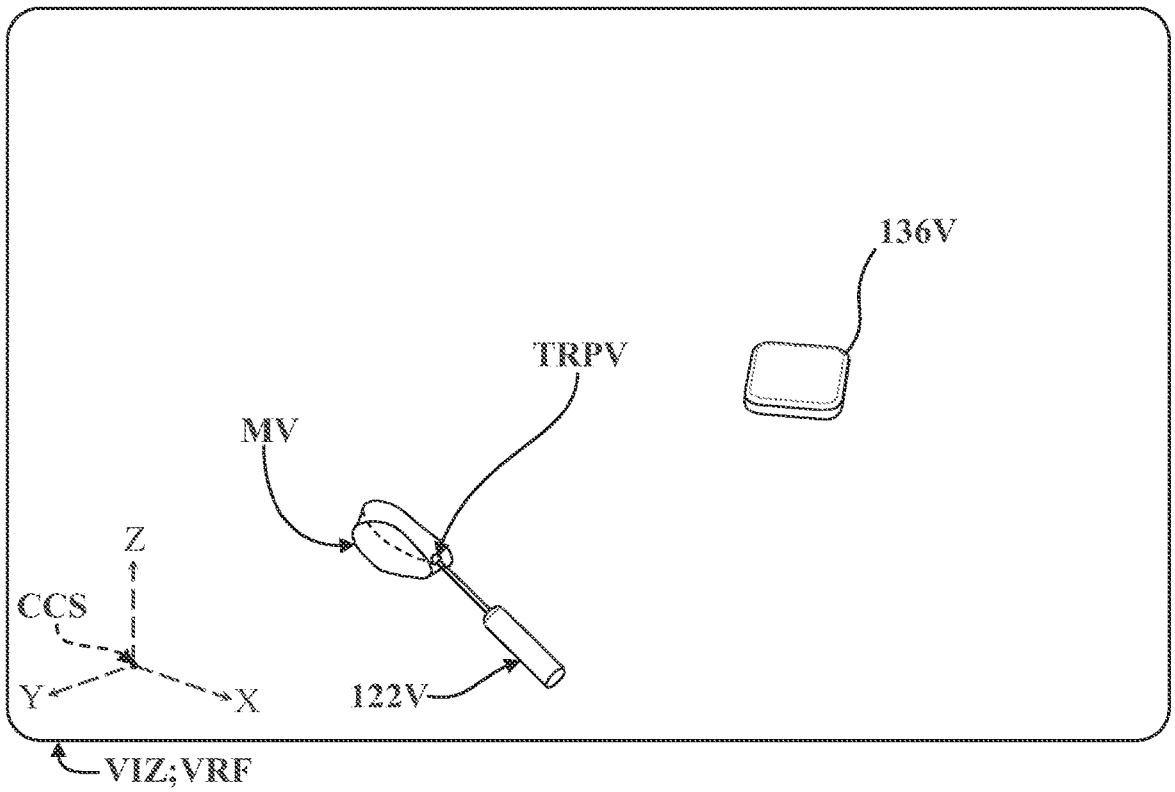
FIG. 47 is another partial perspective view of the surgical tool, the patient tracker, the femur, and the visualization of the virtual reference frame of FIG. 46A, shown with the surgical tool resecting the milling volume along the femoral neck, and shown with the visualization depicting the virtual representation of the surgical tool positioned within the virtual boundary.
Figure 47:
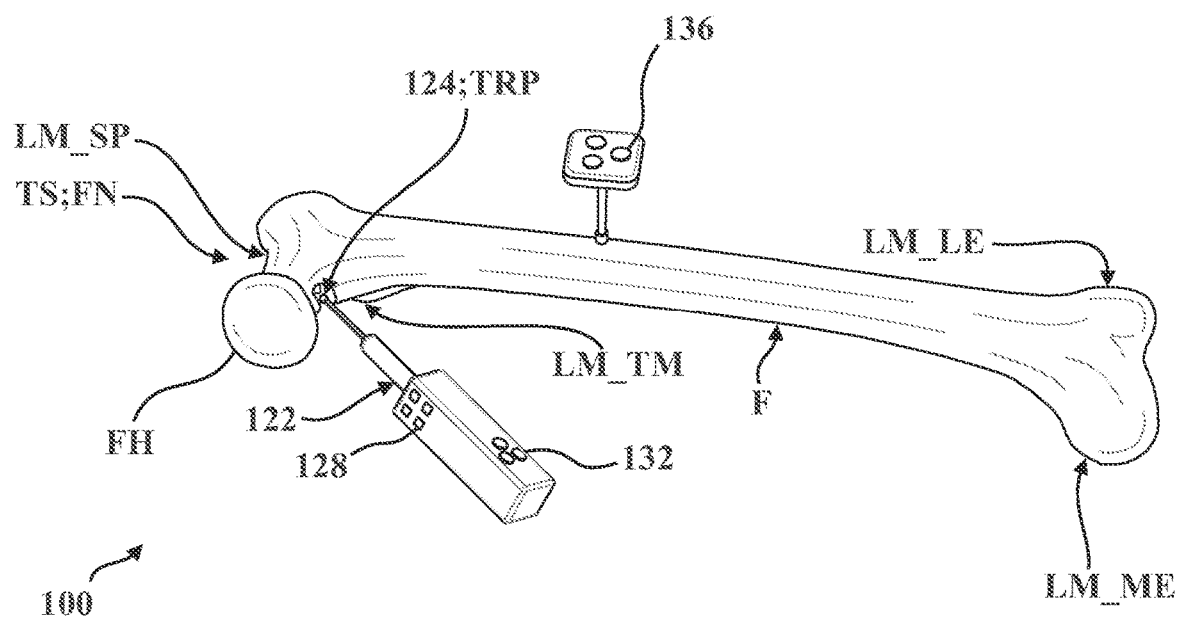

Continuing now from FIG. 46A to FIG. 47, the surgical tool 122 is shown with the energy applicator 124 beginning resection of the femoral head FH along the femoral neck FN at the target site TS, and the visualization VIZ depicts the relative pose of the virtual surgical tool 122V which is shown positioned within the milling volume MV.

Figure 48:
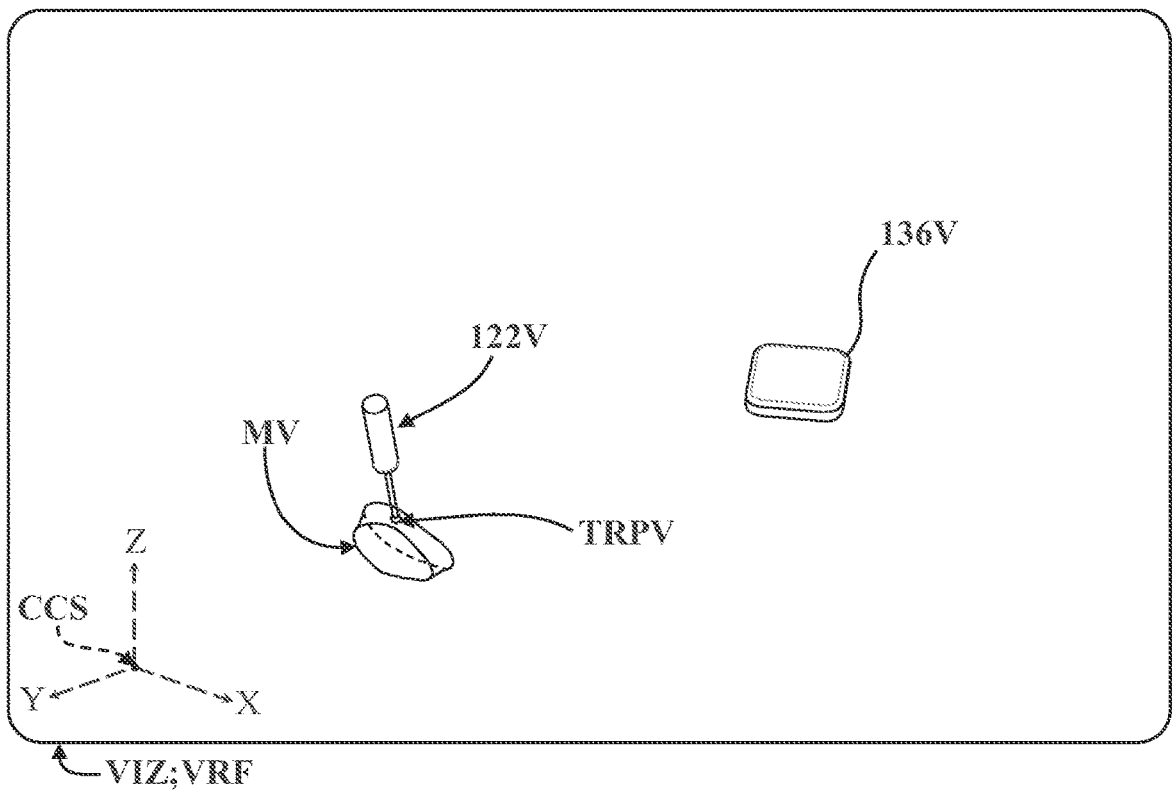
FIG. 48 is another partial perspective view of the surgical tool, the patient tracker, the femur, and the visualization of the virtual reference frame of FIG. 47, shown with the surgical tool further resecting the milling volume along the femoral neck, and shown with the visualization depicting the virtual representation of the surgical tool still position within the virtual boundary.
Figure 48:
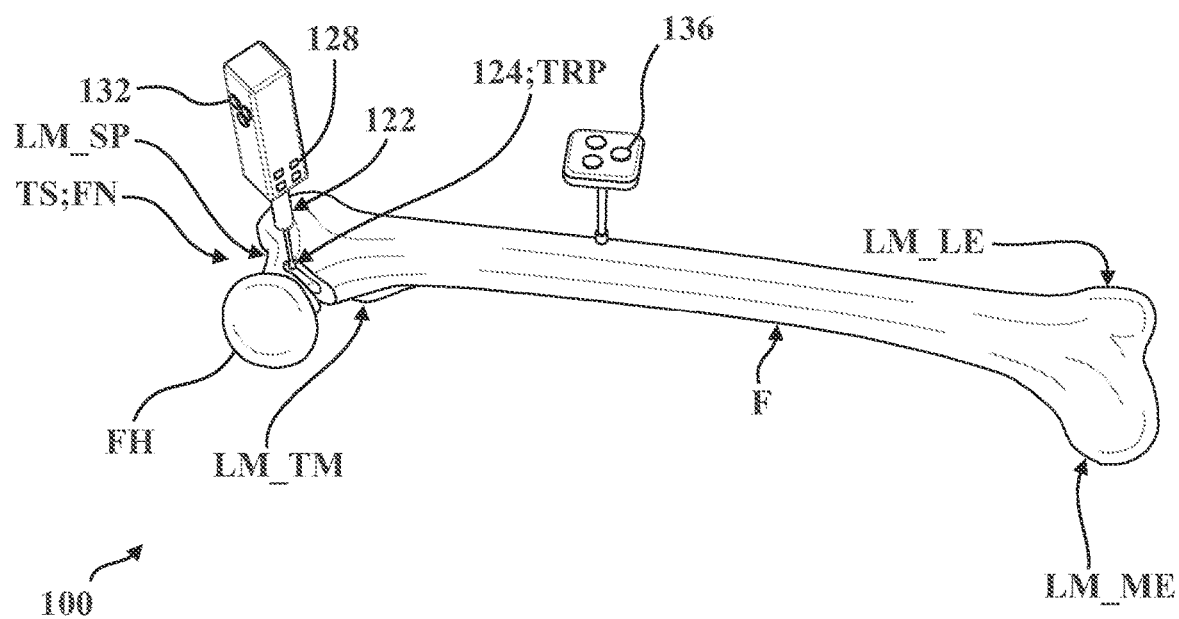

Continuing from FIG. 47 to FIG. 48, the surgical tool 122 is shown with the energy applicator 124 continuing resection of the femoral head FH along the femoral neck FN at the target site TS, and the visualization VIZ depicts the relative pose of the virtual surgical tool 122V which is shown positioned further within the milling volume MV (compare FIG. 48 with FIG. 47).

Figure 49:
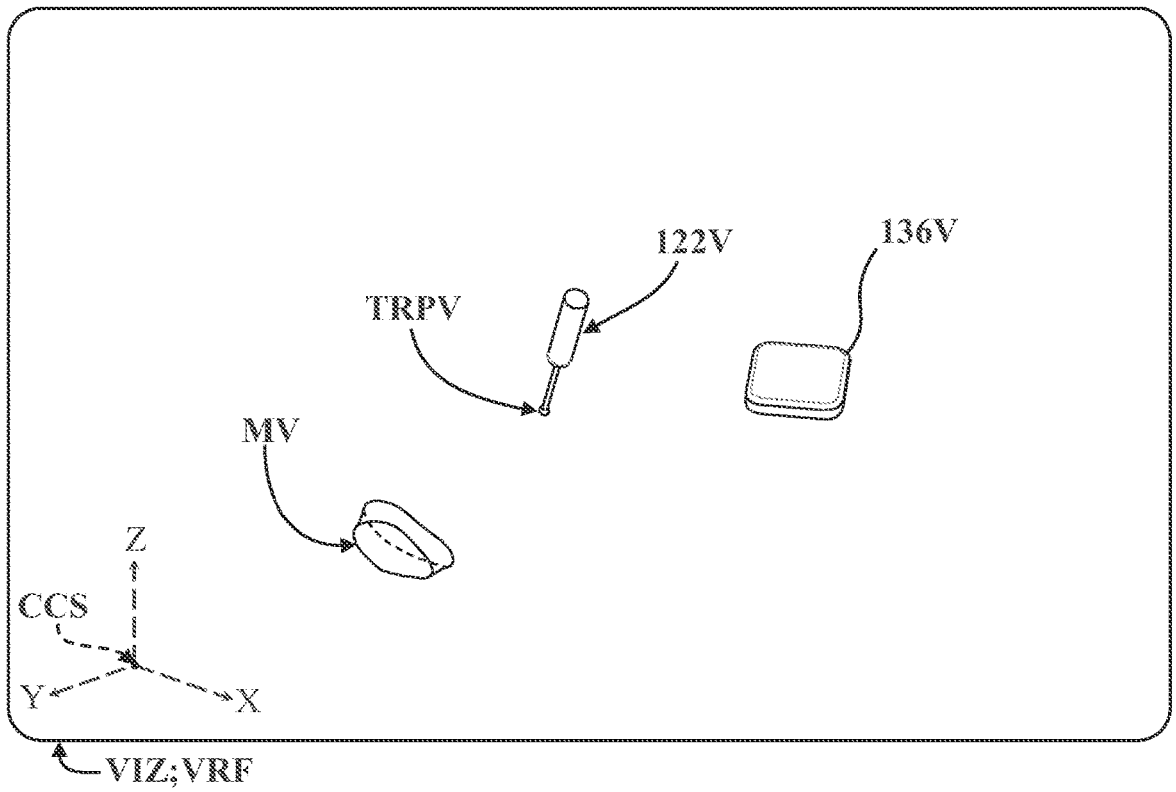
FIG. 49 is another partial perspective view of the surgical tool, the patient tracker, the femur, and the visualization of the virtual reference frame of FIG. 48, shown with the surgical tool moved away from the femur after resecting the milling volume along the femoral neck to remove the femoral head, and shown with the visualization depicting the milling volume.
Figure 49:
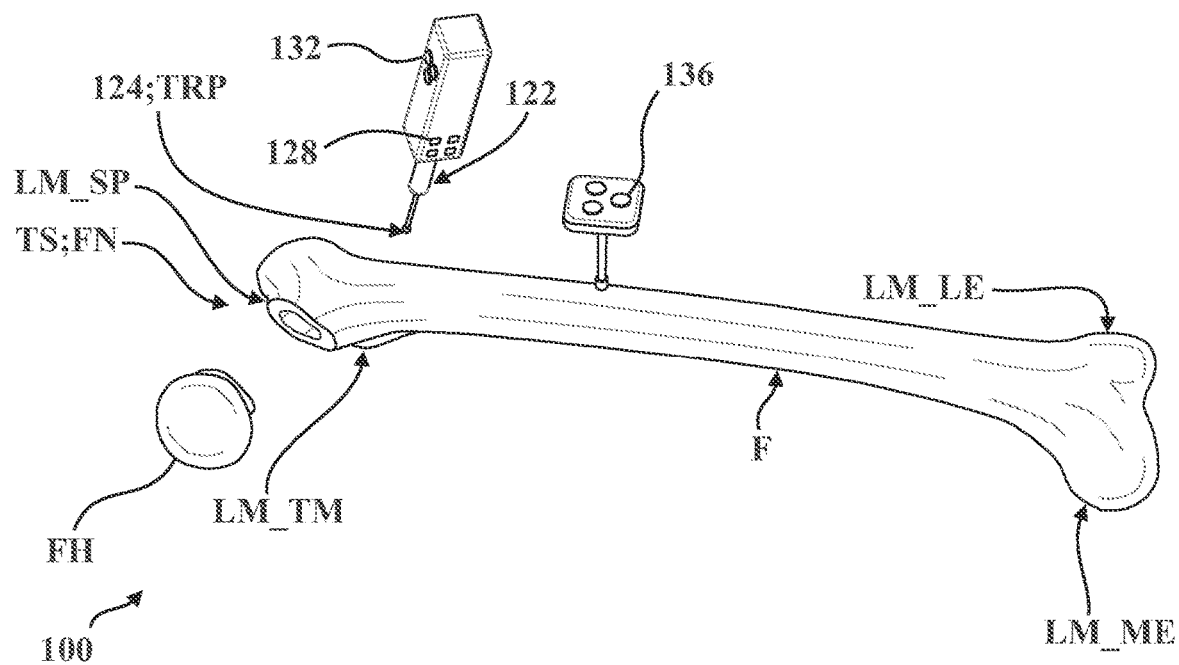

Continuing from FIG. 48 to FIG. 49, the surgical tool 122 is shown spaced from the target site TS after having completed resection of the femoral head FH, which is shown spaced from the femur F.

In this way, the surgical system 100, the CAD program 102, and the various methods and computer-implemented techniques of the present disclosure enable the surgeon to arrange different types of geometrical design objects GDO within the virtual reference frame VRF based on one or more registered local virtual references LVR established using the digitization device 106 in order to facilitate ad-hoc, intraoperative planning of a variety of different surgical steps which may be utilized during the execution of a broad array of different surgical procedures. Specifically, it will be appreciated that various different geometrical design objects GDO can be arranged within the virtual reference frame VRF based on registered local virtual references LVR and/or calculated virtual references CVR to intraoperatively plan surgical steps in a number of different ways, and/or for a number of different purposes.

Thus, the surgeon can intraoperatively identify anatomical features with or without reliance on preoperatively-acquired imaging of the target site TS. In addition, the surgeon can intraoperatively arrange geometrical design objects GDO relative to those identified anatomical features and, based on the arrangement, intraoperatively visualize and/or orientate geometrical design objects GDO in ways which represent cuts to be made during execution, holes to be drilled during execution, and/or milling volumes to be removed during execution.

Furthermore, the surgeon can use the intraoperatively-arranged geometrical design objects GDO to generate cool control data CZ used during execution, such as may be used to control the position and/or operation of the surgical tool 122 relative to the target site TS using intraoperatively-defined milling volumes MV, virtual boundaries 216, and the like. Further, the surgeon can manipulate, position, and/or visualize geometrical design objects GDO, the virtual digitization device 106V, the virtual surgical tool 122V, the virtual patient trackers 136V, 138V, and the like within the visualization VIZ of the virtual reference frame VRF in near-real time using the display unit 148. Moreover, using the HMD unit 140, the surgeon can visualize geometrical design objects GDO rendered overlaid onto the patient's anatomy relative to the target site TS in near-real time using augmented or mixed reality.

It will be further appreciated that the terms "include." "includes," and "including" have the same meaning as the terms "comprise." "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention is intended to be defined in the independent claims, with specific features laid out in the dependent claims, wherein the subject-matter of a claim dependent from one independent claim can also be implemented in connection with another independent claim.

What is claimed is:

1. A surgical system comprising:
    a digitization device comprising a pointer tip configured to contact a target site and one or more control inputs that are configured to be actuated;
    a surgical tool configured to manipulate the target site;
    a navigation system configured to track a state of the digitization device; and
    one or more controllers configured to:
        receive the tracked state of the digitization device from the navigation system;
        display, within a virtual reference frame, a virtual representation of the pointer tip having a pose of the pointer tip derived from the tracked state of the digitization device;
        in response to actuation of the one or more control inputs of the digitization device, register virtual reference points within the virtual reference frame at locations based on the pose of the virtual representation of the pointer tip; and in response to actuation of the one or more control inputs of the digitization device, enable arrangement of one or more geometrical design objects within the virtual reference frame relative to the registered virtual reference points to generate a virtual boundary that defines a region of the target site to be avoided by the surgical tool.

2. The surgical system of claim 1, wherein the one or more controllers are configured to enable arrangement of the one or more geometrical design objects within the virtual reference frame by being configured to:

enable construction of a new geometrical design object from the virtual reference points being sequentially registered with the digitization device;

enable construction of a new geometrical design object from a previously-constructed geometrical design object arranged within the virtual reference frame; and/or enable adjustment to a previously-constructed geometrical design object arranged within the virtual reference frame.

3. The surgical system of claim 1, wherein:

the navigation system includes a patient tracker adapted to be coupled to the target site;

the navigation system is configured to track a state of the patient tracker;

the one or more controllers are configured to display, within the virtual reference frame, a virtual representation of the patient tracker having a pose derived from the tracked state of the patient tracker; and the one or more controllers are configured to fix one or more registered virtual reference points relative to the virtual representation of the patient tracker within the virtual reference frame.

4. The surgical system of claim 1, wherein the one or more controllers are further configured to enable construction of a virtual implant model in response to arrangement of the one or more geometrical design objects within the virtual reference frame relative to one or more registered virtual reference points.

5. The surgical system of claim 1, wherein the one or more controllers are further configured to enable selection of a type of the one or more of the geometrical design objects from a list, in response to actuation of the one or more control inputs of the digitization device.

6. The surgical system of claim 1, wherein the one or more controllers are further configured to temporarily fix the one or more of the geometrical design objects to the virtual representation of the pointer tip such that the one or more geometrical design objects that are temporarily fixed correspondingly follow changes in pose of the virtual representation of the pointer tip within the virtual reference frame.

7. The surgical system of claim 1, wherein:

the surgical tool is coupled to a robotic manipulator;

the navigation system is configured to track a state of the surgical tool; and the one or more controllers are coupled to the robotic manipulator and are configured to control the robotic manipulator to constrain movement and/or operation of the surgical tool in response to the tracked state of the surgical tool meeting, exceeding, or potentially exceeding the virtual boundary.

8. A method of operating a surgical system, the surgical system including a digitization device comprising a pointer tip configured to contact a target site and one or more control inputs, a surgical tool configured to manipulate the target site; a navigation system configured to track a state of the digitization device, and a one or more controllers, the method comprising the one or more controllers performing the following:

receiving the tracked state of the digitization device from the navigation system;

displaying, within a virtual reference frame, a virtual representation of the pointer tip having a pose of the pointer tip derived from the tracked state of the digitization device;

in response to actuation of the one or more control inputs of the digitization device, registering virtual reference points within the virtual reference frame at locations based on the pose of the virtual representation of the pointer tip; and in response to actuation of the one or more control inputs of the digitization device, enabling arrangement of one or more geometrical design objects within the virtual reference frame relative to the registered virtual reference points for generating a virtual boundary that defines a region of the target site to be avoided by the surgical tool.

9. The method of claim 8, comprising the one or more controllers enabling arrangement of the one or more geometrical design objects within the virtual reference frame by:

enabling construction of a new geometrical design object from the virtual reference points being sequentially registered with the digitization device;

enabling construction of a new geometrical design object from a previously-constructed geometrical design object arranged within the virtual reference frame; and/or enabling adjustment to a previously-constructed geometrical design object arranged within the virtual reference frame.

10. The method of claim 8, wherein the navigation system includes a patient tracker adapted to be coupled to the target site and the navigation system is configured to track a state of the patient tracker, the method comprising the one or more controllers:

displaying, within the virtual reference frame, a virtual representation of the patient tracker having a pose derived from the tracked state of the patient tracker; and fixing one or more registered virtual reference points relative to the virtual representation of the patient tracker within the virtual reference frame.

11. The method of claim 8, comprising the one or more controllers further enabling construction of a virtual implant model in response to arrangement of the one or more geometrical design objects within the virtual reference frame relative to one or more registered virtual reference points.

12. The method of claim 8, comprising the one or more controllers further enabling selection of a type of the one or more of the geometrical design objects from a list, in response to actuation of the one or more control inputs of the digitization device.

13. The method of claim 8, comprising the one or more controllers temporarily fixing the one or more of the geometrical design objects to the virtual representation of the pointer tip such that the one or more geometrical design objects that are temporarily fixed correspondingly follow changes in pose of the virtual representation of the pointer tip within the virtual reference frame.

14. The method of claim 8, wherein the surgical tool is coupled to a robotic manipulator, the navigation system is configured to track a state of the surgical tool, and the one or more controllers are coupled to the robotic manipulator, the method comprising the one or more controllers:

controlling the robotic manipulator to constrain movement and/or operation of the surgical tool in response to the tracked state of the surgical tool meeting, exceeding, or potentially exceeding the virtual boundary.

15. A non-transitory computer-readable medium having stored thereon instructions, which when executed by one or more processors, are configured to execute a computer-aided design (CAD) program configured to be utilized with a surgical system, the surgical system including a digitization device comprising a pointer tip configured to contact a target site and one or more control inputs that are configured to be actuated, and a navigation system configured to track a state of the digitization device, the CAD program, when executed, is configured to:

receive the tracked state of the digitization device from the navigation system;

display, within a virtual reference frame, a virtual representation of the pointer tip having a pose of the pointer tip derived from the tracked state of the digitization device;

in response to actuation of the one or more control inputs of the digitization device, register virtual reference points within the virtual reference frame at locations based on the pose of the virtual representation of the pointer tip; and in response to actuation of the one or more control inputs of the digitization device, enable arrangement of one or more geometrical design objects within the virtual reference frame relative to the registered virtual reference points to generate a virtual boundary that defines a region of the target site to be avoided by a surgical tool.

16. The non-transitory computer-readable medium of claim 15, wherein the CAD program, when executed, enables arrangement of the one or more geometrical design objects within the virtual reference frame by being configured to:

enable construction of a new geometrical design object from the virtual reference points being sequentially registered with the digitization device;

enable construction of a new geometrical design object from a previously-constructed geometrical design object arranged within the virtual reference frame; and/or enable adjustment to a previously-constructed geometrical design object arranged within the virtual reference frame.

17. The non-transitory computer-readable medium of claim 15, wherein the CAD program, when executed, is further configured to:

display, within the virtual reference frame, a virtual representation of a patient tracker having a pose derived from the tracked state of the patient tracker; and fix one or more registered virtual reference points relative to the virtual representation of the patient tracker within the virtual reference frame.

18. The non-transitory computer-readable medium of claim 15, wherein the CAD program, when executed, is further configured to enable construction of a virtual implant model in response to arrangement of the one or more geometrical design objects within the virtual reference frame relative to one or more registered virtual reference points.

19. The non-transitory computer-readable medium of claim 15, wherein the CAD program, when executed, is further configured to enable selection of a type of the one or more of the geometrical design objects from a list, in response to actuation of the one or more control inputs of the digitization device.

20. The non-transitory computer-readable medium of claim 15, wherein the CAD program, when executed, is further configured to temporarily fix the one or more of the geometrical design objects to the virtual representation of the pointer tip such that the one or more geometrical design objects that are temporarily fixed correspondingly follow changes in pose of the virtual representation of the pointer tip within the virtual reference frame.

* * * * *